(12) United States Patent
Rau et al.

(10) Patent No.: US 9,855,340 B2
(45) Date of Patent: Jan. 2, 2018

(54) HYDROGEL PRODRUGS

(71) Applicant: Ascendis Pharma A/S, Hellerup (DK)

(72) Inventors: Harald Rau, Dossenheim (DE); Tobias Voigt, Heidelberg (DE); Burkhardt Laufer, Dossenheim (DE); Nicola Bisek, Heidelberg (DE); Franziska Hahn, Stuttgart (DE); Thomas Knappe, Heidelberg (DE)

(73) Assignee: Ascendis Pharma A/S, Hellerup (DK)

( * ) Notice: Subject to any disclaimer, the term of this patent is extended or adjusted under 35 U.S.C. 154(b) by 0 days.

(21) Appl. No.: 14/434,585

(22) PCT Filed: Oct. 8, 2013

(86) PCT No.: PCT/EP2013/070962
§ 371 (c)(1),
(2) Date: Apr. 9, 2015

(87) PCT Pub. No.: WO2014/056926
PCT Pub. Date: Apr. 17, 2014

(65) Prior Publication Data
US 2015/0258205 A1  Sep. 17, 2015

(30) Foreign Application Priority Data
Oct. 11, 2012  (EP) ..................................... 12188228

(51) Int. Cl.
| | | |
|---|---|---|
| *A61K 47/48* | (2006.01) | |
| *C08G 83/00* | (2006.01) | |
| *C08J 3/075* | (2006.01) | |
| *C08G 65/332* | (2006.01) | |
| *A61K 31/4188* | (2006.01) | |
| *C08G 69/44* | (2006.01) | |
| *C08G 69/48* | (2006.01) | |
| *C08G 65/333* | (2006.01) | |
| *C08F 2/22* | (2006.01) | |

(52) U.S. Cl.
CPC .... *A61K 47/48215* (2013.01); *A61K 31/4188* (2013.01); *A61K 47/48146* (2013.01); *A61K 47/48192* (2013.01); *A61K 47/48315* (2013.01); *A61K 47/48546* (2013.01); *A61K 47/48784* (2013.01); *C08G 65/332* (2013.01); *C08G 65/3322* (2013.01); *C08G 65/33337* (2013.01); *C08G 65/33389* (2013.01); *C08G 69/44* (2013.01); *C08G 69/48* (2013.01); *C08G 83/004* (2013.01); *C08G 83/006* (2013.01); *C08J 3/075* (2013.01); *C08F 2/22* (2013.01); *C08G 2210/00* (2013.01); *C08J 2300/202* (2013.01); *C08J 2371/02* (2013.01); *C08J 2400/202* (2013.01); *C08J 2471/02* (2013.01); *C08L 2203/02* (2013.01)

(58) Field of Classification Search
CPC ........ A61K 47/48215; A61K 47/48146; A61K 47/48546; A61K 47/48192; A61K 47/48315; A61K 47/48784; A61K 31/4188; C08G 65/332; C08G 65/3322; C08G 65/33337; C08G 65/33389; C08G 69/44; C08G 69/48; C08G 83/004; C08G 83/006; C08G 2210/00; C08J 3/075; C08J 2300/202; C08J 2371/02; C08J 2400/202; C08J 2471/02; C08L 2203/02; C08F 2/22
See application file for complete search history.

(56) References Cited

U.S. PATENT DOCUMENTS

| | | |
|---|---|---|
| 5,932,462 A | 8/1999 | Harris et al. |
| 8,377,917 B2 | 2/2013 | Hersel et al. |
| 8,906,847 B2 | 12/2014 | Cleemann et al. |
| 8,961,947 B2 | 2/2015 | Rehor et al. |
| 2002/0064546 A1 | 5/2002 | Harris |
| 2005/0009988 A1 | 1/2005 | Harris et al. |
| 2006/0178474 A1 | 8/2006 | Wu et al. |
| 2008/0241102 A1 | 10/2008 | Rau et al. |
| 2008/0253987 A1 | 10/2008 | Rehor et al. |
| 2009/0215923 A1* | 8/2009 | Carnahan .............. A61L 24/046 523/118 |
| 2010/0291021 A1 | 11/2010 | Vetter et al. |
| 2011/0053848 A1 | 3/2011 | Cleemann et al. |

(Continued)

FOREIGN PATENT DOCUMENTS

| | | |
|---|---|---|
| EA | 200501863 | 6/2006 |
| EP | 1625856 | 2/2006 |

(Continued)

OTHER PUBLICATIONS

Sigma-Aldrich Polyethyleneimine Product Data, p. 1-2, retrieved Apr. 14, 2016.*
International Search Report for Application No. PCT/EP2013/070962 dated Nov. 6, 2013.
Vinogradov S. et al., Nonogel Particles: Novel Drug Delivery Systems for Antisense Oligonucleotides, Colloids and Surfaces, B. Bioninterfaces, vol. 16, No. 1-4 (1999) pp. 291-304.
Gude et al., An Accurate Method for the Quantitation of Fmoc-derivatized Solid Phase Supports, Letters in Peptide Science vol. 9, No. 4 (2002) pp. 203-206.

(Continued)

*Primary Examiner* — Robert Jones, Jr.
(74) *Attorney, Agent, or Firm* — Haug Partners LLP

(57) ABSTRACT

The present invention relates to a process for the preparation of a hydrogel and to a hydrogel obtainable by said process. The present invention further relates to a process for the preparation of a hydrogel-spacer conjugate, to a hydrogel-spacer conjugate obtainable by said process, to a process for the preparation of a carrier-linked prodrug and to carrier-linked prodrugs obtainable by said process, in particular to carrier-linked prodrugs that provide for a controlled or sustained release of a drug from a carrier. In addition, the invention relates to the use of the hydrogel for the preparation of a carrier-linked prodrug.

44 Claims, No Drawings

(56) References Cited

U.S. PATENT DOCUMENTS

| | | | |
|---|---|---|---|
| 2012/0156259 A1* | 6/2012 | Rau | A61K 9/0024 424/400 |
| 2012/0156260 A1 | 6/2012 | Rau et al. | |
| 2012/0191039 A1 | 7/2012 | Rau et al. | |
| 2013/0030359 A1 | 1/2013 | Vetter et al. | |
| 2013/0035635 A1 | 2/2013 | Rau et al. | |
| 2013/0053301 A1 | 2/2013 | Rau et al. | |
| 2013/0150281 A1 | 6/2013 | Hersel et al. | |
| 2014/0249093 A1 | 9/2014 | Vetter et al. | |
| 2015/0057221 A1 | 2/2015 | Cleemann et al. | |

FOREIGN PATENT DOCUMENTS

| | | |
|---|---|---|
| RU | 2401283 | 10/2010 |
| WO | WO 9914259 | 3/1999 |
| WO | WO 2005/099768 | 10/2005 |
| WO | WO 2006/003014 | 1/2006 |
| WO | WO 2006/136586 | 12/2006 |
| WO | WO 2008/125655 | 10/2008 |
| WO | WO 2009/095479 | 8/2009 |
| WO | WO 2011/012715 | 2/2011 |
| WO | WO 2011/012718 | 2/2011 |
| WO | WO 2011/012721 | 2/2011 |
| WO | WO 2011/012722 | 2/2011 |
| WO | WO 2011/089214 | 7/2011 |
| WO | WO 2011/089215 | 7/2011 |
| WO | WO 2011/089216 | 7/2011 |
| WO | WO 2013/024053 | 2/2013 |
| WO | WO/2013/160340 | 10/2013 |

* cited by examiner

HYDROGEL PRODRUGS

The present application claims priority from PCT Patent Application No. PCT/EP2013/070962 filed on Oct. 8, 2013, which claims priority from European Patent Application No. EP 12188228.6 filed on Oct. 11, 2012, the disclosures of which are incorporated herein by reference in their entirety.

FIELD OF THE INVENTION

The present invention relates to a process for the preparation of a hydrogel and to a hydrogel obtainable by said process. The present invention further relates to a process for the preparation of a hydrogel-spacer conjugate, to a hydrogel-spacer conjugate obtainable by said process, to a process for the preparation of a carrier-linked prodrug and to carrier-linked prodrugs obtainable by said process, in particular to carrier-linked prodrugs that provide a controlled and/or sustained release of a drug from a carrier. In addition, the invention relates to the use of the hydrogel for the preparation of a carrier-linked prodrug.

BACKGROUND OF THE INVENTION

Conventional hydrogels are three-dimensional, hydrophilic or amphiphilic polymeric networks capable of taking up large quantities of water. These networks may be composed of various polymers and are insoluble due to the presence of covalent chemical and/or physical crosslinks, such as ionic, hydrophobic interactions or entanglements.

Many conventional hydrogels are severely limited in their application. Some hydrogels are used for pharmaceutical applications such as wound closure, tissue engineering or drug delivery. Hydrogels for tissue sealing are for example disclosed in WO 2008/125655 A1.

Further, WO 99/014259 A1 discloses cross-linked PEG hydrogels in which drug molecules are entrapped.

The release of entrapped drug molecules from such conventional hydrogels depends on the degradation of the hydrogel and may lead to a burst release, temporarily causing too high drug levels and difficult to predict drug release. It is desirable to control and/or sustain the release of the drug from a hydrogel. WO 06/003014 A2 and WO 2011/012715 A1 describe hydrogels as carriers in carrier-linked prodrugs, wherein the biologically active moieties are covalently linked to the hydrogel through reversible prodrug linkers. Such hydrogel-linked prodrugs release the drug controlled and with a specific half-live.

However, the hydrogels disclosed in WO 2011/012715 A1 are preferably used for the controlled and sustained release of smaller drug molecules and may not provide sufficient access for larger drug molecules, such as protein drugs, thus resulting in a low drug load of such hydrogels.

DETAILED DESCRIPTION OF THE INVENTION

Process for the Preparation of a Hydrogel and Hydrogel

Accordingly, there is a need for hydrogels that can be used as carriers for carrier-linked prodrugs, which are suitable for the controlled and sustained release of larger drug molecules.

It is therefore an object of the present invention to overcome at least some of the above-mentioned shortcomings and to provide a hydrogel, which can be used as a carrier for carrier-linked prodrugs which are suitable for the controlled and/or sustained release of larger drug molecules.

In one aspect, the present invention relates to a process for the preparation of a hydrogel comprising the steps of:
(a) providing a mixture comprising
  (a-i) at least one backbone reagent, wherein the at least one backbone reagent has a molecular weight ranging from 1 to 100 kDa, and comprises at least three amines ($-NH_2$ and/or $-NH-$);
  (a-ii) at least one crosslinker reagent, wherein the at least one crosslinker reagent has a molecular weight ranging from 6 to 40 kDa, the at least one crosslinker reagent comprising
    (i) at least two carbonyloxy groups ($-(C=O)-O-$ or $-O-(C=O)-$), and additionally
    (ii) at least two activated functional end groups selected from the group consisting of activated ester groups, activated carbamate groups, activated carbonate groups and activated thiocarbonate groups,
  and being PEG-based comprising at least 70% PEG; and
  (a-iii) a first solvent and at least a second solvent, which second solvent is immiscible in the first solvent,
in a weight ratio of the at least one backbone reagent to the at least one crosslinker reagent ranging from 1:99 to 99:1; and
(b) polymerizing the mixture of step (a) in a suspension polymerization to a hydrogel.

Generally, it is known that the design of the crosslinker influences the pore size of a hydrogel, but the expectation was that the longer the crosslinkers are, the more likely they are to form secondary structures which would obstruct access to the inner space of the hydrogel. Such obstructions would prevent larger protein drugs from entering the inner space of the hydrogel and attachment of such drug molecules would be restricted primarily to the surface and areas close to the surface of the hydrogel. It was now surprisingly found that despite these expected limitations large drugs, such as proteins, are able to enter the hydrogels of the present invention in amounts that render these hydrogels suitable carriers for prodrugs.

Within the Present Invention the Terms are Used with the Meaning as Follows

As used herein, the term "hydrogel" means a hydrophilic or amphiphilic polymeric network composed of homopolymers or copolymers, which is insoluble due to the presence of covalent chemical crosslinks. The crosslinks provide the network structure and physical integrity. Hydrogels exhibit a thermodynamic compatibility with water which allows them to swell in aqueous media.

As used herein, the term "reagent" means a chemical compound which comprises at least one functional group for reaction with the functional group of another reagent or moiety.

As used herein, the term "backbone reagent" means a reagent, which is suitable as a starting material for forming hydrogels. As used herein, a backbone reagent preferably does not comprise biodegradable linkages. A backbone reagent may comprise a "branching core" which refers to an atom or moiety to which more than one other moiety is attached.

As used herein, the term "crosslinker reagent" means a linear or branched reagent, which is suitable as a starting material for crosslinking backbone reagents. Preferably, the crosslinker reagent is a linear chemical compound. A crosslinker reagent comprises at least two biodegradable linkages.

As used herein, the term "moiety" means a part of a molecule, which lacks one or more atom(s) compared to the corresponding reagent. If, for example, a reagent of the formula "H—X—H" reacts with another reagent and becomes part of the reaction product, the corresponding moiety of the reaction product has the structure "H—X—" or "—X—", whereas each "—" indicates attachment to another moiety. Accordingly, a biologically active moiety is released from a prodrug as a drug.

Accordingly, the phrase "in bound form" is used to refer to the corresponding moiety of a reagent, i.e. "lysine in bound form" refers to a lysine moiety which lacks one or more atom(s) of the lysine reagent and is part of a molecule.

As used herein, the term "functional group" means a group of atoms which can react with other functional groups. Functional groups include but are not limited to the following groups: carboxylic acid (—(C=O)OH), primary or secondary amine (—NH$_2$, —NH—), maleimide, thiol (—SH), sulfonic acid (—(O=S=O)OH), carbonate, carbamate (—O(C=O)N<), hydroxy (—OH), aldehyde (—(C=O)H), ketone (—(C=O)—), hydrazine (>N—N<), isocyanate, isothiocyanate, phosphoric acid (—O(P=O)OHOH), phosphonic acid (—O(P=O)OHH), haloacetyl, alkyl halide, acryloyl, aryl fluoride, hydroxylamine, disulfide, vinyl sulfone, vinyl ketone, diazoalkane, oxirane, and aziridine.

As used herein, the term "activated functional group" means a functional group, which is connected to an activating group, i.e. a functional group was reacted with an activating reagent. Preferred activated functional groups include but are not limited to activated ester groups, activated carbamate groups, activated carbonate groups and activated thiocarbonate groups. Preferred activating groups are selected from formulas ((f-i) to (f-vi):

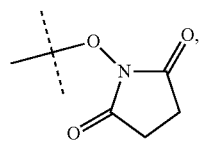
(f-i)

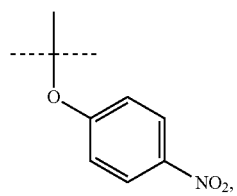
(f-ii)

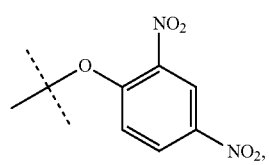
(f-iii)

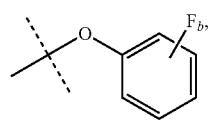
(f-iv)

-continued

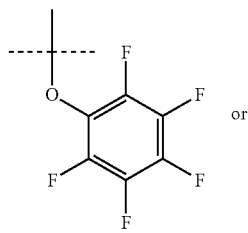
(f-v)

or

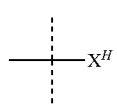
(f-vi)

wherein
the dashed lines indicate attachment to the rest of the molecule;
b is 1, 2, 3 or 4; and
$X^H$ is Cl, Br, I, or F.

Accordingly, a preferred activated ester has the formula

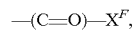

wherein
$X^F$ is selected from formula (f-i), (f-ii), (f-iii), (f-iv), (f-v) and (f-vi).

Accordingly, a preferred activated carbamate has the formula

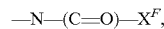

wherein
$X^F$ is selected from formula (f-i), (f-ii), (f-iii), (f-iv), (f-v) and (f-vi).

Accordingly, a preferred activated carbonate has the formula

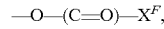

wherein
$X^F$ is selected from formula (f-i), (f-ii), (f-iii), (f-iv), (f-v) and (f-vi).

Accordingly, a preferred activated thioester has the formula

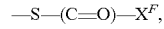

wherein
$X^F$ is selected from formula (f-i), (f-ii), (f-iii), (f-iv), (f-v) and (f-vi).

Accordingly, an "activated end functional group" is an activated functional group which is localized at the end of a moiety or molecule, i.e. is a terminal activated functional group.

As used herein, the term "capping group" means a moiety which is irreversibly, i.e. permanently, connected to a functional group to render it incapable of reacting with functional groups of other reagents or moieties.

As used herein, the term "protecting group" means a moiety which is reversibly connected to a functional group to render it incapable of reacting with, for example, another functional group. Suitable alcohol (—OH) protecting groups are, for example, acetyl, benzoyl, benzyl, β-methoxyethoxymethyl ether, dimethoxytrityl, methoxymethyl ether, methoxytrityl, p-methoxybenzyl ether, methylthiomethyl ether, pivaloyl, tetrahydropyranyl, trityl, trimethylsilyl, tert-butyldimethylsilyl, tri-iso-propylsilyloxymethyl, triisopropylsilyl ether, methyl ether, and ethoxyethyl ether. Suitable amine protecting groups are, for example, carbobenzyloxy, p-methoxybenzyl carbonyl, tert-butyloxycarbonyl, 9-fluorenylmethyloxyarbonyl, acetyl, benzoyl, benzyl, carbamate, p-methoxybenzyl, 3,4-dimethoxybenzyl, p-methoxyphenyl, and tosyl. Suitable carbonyl protecting groups are, for example, acetals and ketals, acylals and dithianes. Suitable carboxylic acid protecting groups are, for example, methyl esters, benzyl esters, tert-butyl esters, 2,6-dimethylphenol, 2,6-diisopropylphenol, 2,6.-di-tert-butylphenol, silyl esters, orthoesters, and oxazoline. Suitable phosphate protecting groups are, for example, 2-cyanoethyl and methyl.

As used herein, the terms "work-up" and "working-up" refer to the series of manipulations required to isolate and purify the product(s) of a chemical reaction, in particular of a polymerization.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may for example also comprise functional groups or capping moieties. Preferably, a polymer has a molecular weight of at least 0.5 kDa, e.g. a molecular weight of at least 1 kDa, a molecular weight of at least 2 kDa, a molecular weight of at least 3 kDa or a molecular weight of at least 5 kDa.

As used herein, the term "polymeric" means a reagent or a moiety comprising one or more polymer(s).

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers. As used herein, the term "number average molecular weight" means the ordinary arithmetic means of the molecular weights of the individual polymers.

As used herein, the term "polymerization" or "polymerizing" means the process of reacting monomer or macromonomer reagents in a chemical reaction to form polymer chains or networks, including but not limited to hydrogels.

As used herein, the term "macromonomer" means a molecule that was obtained from the polymerization of monomer reagents.

As used herein, the term "condensation polymerization" or "condensation reaction" means a chemical reaction, in which the functional groups of two reagents react to form one single molecule, i.e. the reaction product, and a low molecular weight molecule, for example water, is released.

As used herein, the term "suspension polymerization" means a heterogeneous and/or biphasic polymerization reaction, wherein the monomer reagents are dissolved in a first solvent, forming the disperse phase which is emulsified in a second solvent, forming the continuous phase. In the present invention, the monomer reagents are the at least one backbone reagent and the at least one crosslinker reagent. Both the first solvent and the monomer reagents are not soluble in the second solvent. Such emulsion is formed by stirring, shaking, exposure to ultrasound or Microsieve™ emulsification, more preferably by stirring or Microsieve™ emulsification and more preferably by stirring. This emulsion is stabilized by an appropriate emulsifier. The polymerization is initiated by addition of a base as initiator which is soluble in the first solvent. A suitable commonly known base suitable as initiator may be a tertiary base, such as tetramethylethylenediamine (TMEDA).

As used herein, the term "immiscible" means the property where two substances are not capable of combining to form a homogeneous mixture.

As used herein, the term "polyamine" means a reagent or moiety comprising more than one amine (—NH— and/or —NH$_2$), e.g. from 2 to 64 amines, from 4 to 48 amines, from 6 to 32 amines, from 8 to 24 amines, or from 10 to 16 amines. Particularly preferred polyamines comprise from 2 to 32 amines.

As used herein, the term "PEG-based comprising at least X % PEG" in relation to a moiety or reagent means that said moiety or reagent comprises at least X % (w/w) ethylene glycol units (—CH$_2$CH$_2$O—), wherein the ethylene glycol units may be arranged blockwise, alternating or may be randomly distributed within the moiety or reagent and preferably all ethylene glycol units of said moiety or reagent are present in one block; the remaining weight percentage of the PEG-based moiety or reagent are other moieties especially selected from the following substituents and linkages:

$C_{1-50}$ alkyl, $C_{2-50}$ alkenyl, $C_{2-50}$ alkynyl, $C_{3-10}$ cycloalkyl, 4- to 7-membered heterocyclyl, 8- to 11-membered heterobicyclyl, phenyl; naphthyl; indenyl; indanyl; and tetralinyl; and linkages selected from the group comprising

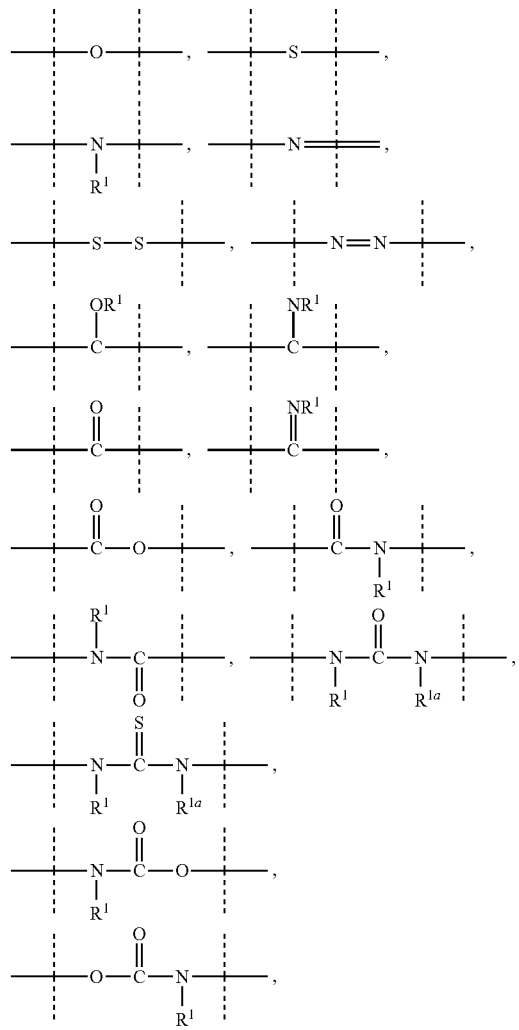

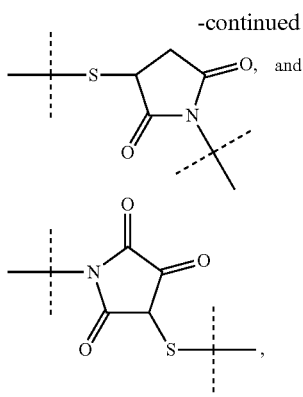

wherein
dashed lines indicate attachment to the remainder of the moiety or reagent, and $R^1$ and $R^{1a}$ are independently of each other selected from H and $C_{1-6}$ alkyl.

As used herein, the term "$C_{1-4\ alkyl}$" alone or in combination means a straight-chain or branched alkyl group having 1 to 4 carbon atoms. If present at the end of a molecule, examples of straight-chain and branched $C_{1-4}$ alkyl groups are methyl, ethyl, n-propyl, isopropyl, n-butyl, isobutyl, sec-butyl and tert-butyl. When two moieties of a molecule are linked by the $C_{1-4}$ alkyl group, then examples for such $C_{1-4}$ alkyl groups are —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—, —CH$_2$—CH$_2$—CH$_2$—CH$_2$—, and —CH$_2$—CH$_2$—CH$_2$(CH$_3$)—. Each hydrogen atom of a $C_{1-4}$ alkyl group may be replaced by a substituent as defined below.

As used herein, the term "$C_{1-6}$ alkyl" alone or in combination means a straight-chain or branched alkyl group having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are —CH$_2$—, —CH$_2$—CH$_2$—, —CH(CH$_3$)—, —CH$_2$—CH$_2$—CH$_2$—, —CH(C$_2$H$_5$)— and —C(CH$_3$)$_2$—. Each hydrogen atom of a $C_{1-6}$ alkyl group may be replaced by a substituent as defined below.

Accordingly, as used herein, the term "$C_{1-20}$ alkyl" alone or in combination means a straight-chain or branched alkyl group having 1 to 20 carbon atoms. The term "$C_{8-18}$ alkyl" alone or in combination means a straight-chain or branched alkyl group having 8 to 18 carbon atoms. Accordingly, as used herein, the term "$C_{1-50}$ alkyl" alone or in combination means a straight-chain or branched alkyl group having 1 to 50 carbon atoms. Each hydrogen atom of a $C_{1-20}$ alkyl group, a $C_{8-18}$ alkyl group and $C_{1-50}$ alkyl group may be replaced by a substituent. In each case the alkyl group may be present at the end of a molecule or two moieties of a molecule may be linked by the alkyl group.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are —CH=CH$_2$, —CH=CH—CH$_3$, —CH$_2$—CH=CH$_2$, —CH=CHCH$_2$—CH$_3$ and —CH=CH—CH=CH$_2$. When two moieties of a molecule are linked by the $C_{2-6}$ alkenyl group, then an example for such $C_{2-6}$ alkenyl is —CH=CH—. Each hydrogen atom of a $C_{2-6}$ alkenyl group may be replaced by a substituent as defined below. Optionally, one or more triple bond(s) may occur.

Accordingly, as used herein, the term "$C_{2-20}$ alkenyl" alone or in combination means a straight-chain or branched hydrocarbon residue comprising at least one carbon-carbon double bond having 2 to 20 carbon atoms. The term "$C_{2-50}$ alkenyl" alone or in combination means a straight-chain or branched hydrocarbon residue comprising at least one carbon-carbon double bond having 2 to 50 carbon atoms. If present at the end of a molecule, examples are —CH=CH$_2$, —CH=CH—CH$_3$, —CH$_2$—CH=CH$_2$, —CH=CHCH$_2$—CH$_3$ and —CH=CH—CH=CH$_2$. When two moieties of a molecule are linked by the alkenyl group, then an example is e.g. —CH=CH—. Each hydrogen atom of a $C_{2-20}$ alkenyl or $C_{2-50}$ alkenyl group may be replaced by a substituent as defined below. Optionally, one or more triple bond(s) may occur.

As used herein, the term "$C_{2-6}$ alkynyl" alone or in combination means straight-chain or branched hydrocarbon residue comprising at least one carbon-carbon triple bond having 2 to 6 carbon atoms. If present at the end of a molecule, examples are —C≡CH, —CH$_2$—C≡CH, CH$_2$—CH$_2$—C≡CH and CH$_2$—C≡C—CH$_3$. When two moieties of a molecule are linked by the alkynyl group, then an example is: —C≡C—. Each hydrogen atom of a $C_{2-6}$ alkynyl group may be replaced by a substituent as defined below. Optionally, one or more double bond(s) may occur.

Accordingly, as used herein, the term "$C_{2-20}$ alkynyl" alone or in combination means a straight-chain or branched hydrocarbon residue comprising at least one carbon-carbon triple bond having 2 to 20 carbon atoms and "$C_{2-50}$ alkynyl" alone or in combination means a straight-chain or branched hydrocarbon residue comprising at least one carbon-carbon triple bond having 2 to 50 carbon atoms. If present at the end of a molecule, examples are —C≡CH, —CH$_2$—C≡CH, CH$_2$—CH$_2$—C≡CH and CH$_2$—C≡C—CH$_3$. When two moieties of a molecule are linked by the alkynyl group, then an example is —C≡C—. Each hydrogen atom of a $C_{2-20}$ alkynyl or $C_{2-50}$ alkynyl group may be replaced by a substituent as defined below. Optionally, one or more double bond(s) may occur.

As used herein, the terms "$C_{3-8}$ cycloalkyl" or "$C_{3-8}$ cycloalkyl ring" means a cyclic alkyl chain having 3 to 8 carbon atoms, which may be saturated or unsaturated, e.g. cyclopropyl, cyclobutyl, cyclopentyl, cyclohexyl, cyclohexenyl, cycloheptyl, cyclooctyl. Each hydrogen atom of a cycloalkyl carbon may be replaced by a substituent as defined below. The term "$C_{3-8}$ cycloalkyl" or "$C_{3-8}$ cycloalkyl ring" also includes bridged bicycles like norbonane or norbonene. Accordingly, "$C_{3-5}$ cycloalkyl" means a cycloalkyl having 3 to 5 carbon atoms and "$C_{3-10}$ cycloalkyl" means a cycloalkyl having 3 to 10 carbon atoms.

Accordingly, as used herein, the term "$C_{3-10}$ cycloalkyl" means a carbocyclic ring system having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl, cyclodecyl. The term "$C_{3-10}$ cycloalkyl" also includes at least partially saturated carbomono- and -bicycles.

As used herein, the term "halogen" means fluoro, chloro, bromo or iodo. Particularly preferred is fluoro or chloro.

As used herein, the term "4- to 7-membered heterocyclyl" or "4- to 7-membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 4- to 7-membered heterocycles include but are not limited to azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 4- to 7-membered heterocyclyl or 4- to 7-membered heterocyclic group may be replaced by a substituent as defined below.

As used herein, the term "8- to 11-membered heterobicyclyl" or "8- to 11-membered heterobicycle" means a heterocyclic system of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

The term "substituted" means that one or more —H atom(s) of a molecule or moiety are replaced by a different atom or a group of atoms, which are referred to as "substituent". Suitable substituents are selected from the group consisting of halogen; CN; COOR$^9$; OR$^9$; C(O)R$^9$; C(O)N(R$^9$R$^{9a}$); S(O)$_2$N(R$^9$R$^{9a}$); S(O)N(R$^9$R$^{9a}$); S(O)$_2$R$^9$; S(O)R$^9$; N(R$^9$)S(O)$_2$N(R$^{9a}$R$^{9b}$); SR$^9$; N(R$^9$R$^{9a}$); NO$_2$; OC(O)R$^9$; N(R$^9$)C(O)R$^{9a}$; N(R$^9$)S(O)$_2$R$^{9a}$; N(R$^9$)S(O)R$^{9a}$; N(R$^9$)C(O)OR$^{9a}$; N(R$^9$)C(O)N(R$^{9a}$R$^{9b}$); OC(O)N(R$^9$R$^{9a}$); T; C$_{1-50}$ alkyl; C$_{2-50}$ alkenyl; or C$_{2-50}$ alkynyl, wherein T; C$_{1-50}$ alkyl; C$_{2-50}$ alkenyl; and C$_{2-50}$ alkynyl are optionally substituted with one or more R$^{10}$, which are the same or different and wherein C$_{1-50}$ alkyl; C$_{2-50}$ alkenyl; and C$_{2-50}$ alkynyl are optionally interrupted by one or more group(s) selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

wherein
R$^9$, R$^{9a}$, R$^{9b}$ are independently selected from the group consisting of H; T; and C$_{1-50}$ alkyl; C$_{2-50}$ alkenyl; or C$_{2-50}$ alkynyl, wherein T; C$_{1-50}$ alkyl; C$_{2-50}$ alkenyl; and C$_{2-50}$ alkynyl are optionally substituted with one or more R$^{10}$, which are the same or different and wherein C$_{1-50}$ alkyl; C$_{2-50}$ alkenyl; and C$_{2-50}$ alkynyl are optionally interrupted by one or more group(s) selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

T is selected from the group consisting of phenyl; naphthyl; indenyl; indanyl; tetralinyl; C$_{3-10}$ cycloalkyl; 4 to 7 membered heterocyclyl; or 8- to 11-membered heterobicyclyl, wherein T is optionally substituted with one or more R$^{10}$, which are the same or different;

R$^{10}$ is halogen; CN; oxo (=O); COOR$^{12}$; OR$^{12}$; C(O)R$^{12}$; C(O)N(R$^{12}$R$^{12a}$); S(O)$_2$N(R$^{12}$R$^{12a}$); S(O)N(R$^{12}$R$^{12a}$); S(O)$_2$R$^{12}$; S(O)R$^{12}$; N(R$^{12}$)S(O)$_2$N(R$^{12a}$R$^{12b}$); SR$^{12}$; N(R$^{12}$R$^{12a}$); NO$_2$; OC(O)R$^{12}$; N(R$^{12}$)C(O)R$^{12a}$; N(R$^{12}$)S(O)$_2$R$^{12a}$; N(R$^{12}$)S(O)R$^{12a}$; N(R$^{12}$)C(O) OR$^{12a}$; N(R$^{12}$)C(O)N(R$^{12a}$R$^{12b}$); OC(O)N(R$^{12}$R$^{12a}$); or C$_{1-6}$ alkyl, wherein C$_{1-6}$ alkyl is optionally substituted with one or more halogen, which are the same or different;

R$^{11}$, R$^{11a}$, R$^{12}$, R$^{12a}$, R$^{12b}$ are independently selected from the group consisting of H; or C$_{1-6}$ alkyl, wherein C$_{1-6}$ alkyl is optionally substituted with one or more halogen, which are the same or different.

In one embodiment R$^9$, R$^{9a}$, R$^{9b}$ may be independently of each other H.

In one embodiment R$^{10}$ is C$_{1-6}$ alkyl.

In one embodiment T is phenyl.

Preferably, a maximum of 6 —H atoms of a molecule are independently replaced by a substituent, e.g. 5—H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

As used herein, the term "interrupted" means that between two carbon atoms or at the end of a carbon chain between the respective carbon atom and the hydrogen atom one or more atom(s) are inserted.

As used herein, the term "prodrug" means a compound that undergoes biotransformation before exhibiting its pharmacological effects. Prodrugs can thus be viewed as biologically active moieties connected to specialized non-toxic protective groups used in a transient manner to alter or to eliminate undesirable properties in the parent molecule. This also includes the enhancement of desirable properties in the drug and the suppression of undesirable properties.

As used herein, the term "carrier-linked prodrug" means a prodrug that contains a temporary linkage of a biologically active moiety with a transient carrier group that produces improved physicochemical or pharmacokinetic properties and that can be easily removed in vivo, usually by a hydrolytic cleavage.

As used herein, the term "reversible prodrug linker moiety" means a moiety which on its one end is attached to a biologically active moiety D through a reversible linkage and on another end is attached through a permanent linkage, which in the present invention is formed by the reaction of an amine functional group of a backbone moiety or $A^{x2}$ with $A^{y1}$, thereby linking the biologically active moiety to the hydrogel carrier in the carrier-linked prodrugs of the present invention. A "reversible linkage" is a linkage that is non-enzymatically hydrolytically degradable, i.e. cleavable, under physiological conditions (aqueous buffer at pH 7.4, 37° C.) with a half-life ranging from one hour to twelve months.

In contrast, a "permanent linkage" is non-enzymatically hydrolytically degradable under physiological conditions (aqueous buffer at pH 7.4, 37° C.) with half-lives of more than twelve months.

A "biodegradable linkage" is a linkage that is enzymatically and/or non-enzymatically hydrolytically degradable, i.e. cleavable, under physiological conditions (aqueous buffer at pH 7.4, 37° C.) with a half-life ranging from one hour to twelve months. Preferably, also a biodegradable linkage is non-enzymatically hydrolytically degradable under physiological conditions.

As used herein, the term "traceless prodrug linker" means a reversible prodrug linker which upon cleavage releases the drug in its free form. As used herein, the term "free form" of a drug means the drug in its unmodified, pharmacologically active form.

As used herein, the term "peptide" means a short polymer of amino acid monomers linked by peptide bonds. The term "polypeptide" means a peptide comprising up to and including 50 amino acid monomers. The term "protein" means a peptide of more than 50 amino acid monomers.

As used herein, the term "oligonucleotide" means a short nucleic acid polymer of up to 100 bases.

As used herein, the term "pharmaceutical composition" means one or more active ingredients, and one or more inert ingredients, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing the carrier-linked prodrug of the present invention and one or more pharmaceutically acceptable excipient(s).

As used herein, the term "excipient" refers to a diluent, adjuvant, or vehicle with which the therapeutic is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, water, ethanol and the like. The pharmaceutical composition, if desired, can also contain minor amounts of wetting or emulsifying agents, pH buffering agents, like, for example, acetate, succinate, tris, carbonate, phosphate, HEPES (4-(2-hydroxyethyl)-1-piperazineethanesulfonic acid), MES (2-(N-morpholino)ethanesulfonic acid), or can contain detergents, like Tween®, poloxamers, poloxamines, CHAPS, Igepal® (octylphenoxy poly(ethyleneoxy)ethanol), or amino acids like, for example, glycine, lysine, or histi-dine. These pharmaceutical compositions can take the form of solutions, suspensions, emulsions, tablets, pills, capsules, powders, sustained-release formulations and the like. The pharmaceutical composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Examples of suitable pharmaceutical excipients are described in "Remington's Pharmaceutical Sciences" by E. W. Martin. Such compositions will contain a therapeutically effective amount of the drug or biologically active moiety, together with a suitable amount of excipient so as to provide the form for proper administration to the patient. The formulation should suit the mode of administration.

In general the term "comprise" or "comprising" also encompasses "consist of" or "consisting of".

Some of the backbone and crosslinker reagents, which can be used as starting material in process step (a) are commercially available. Further, the backbone and crosslinker reagents can be prepared according to a method described in the Examples section. A method for the synthesis of a suitable backbone reagent is described in example 1 of WO2011/012715A1, which is incorporated by reference herein. Example 2 of WO2011/012715A1 further provides methods for the synthesis of crosslinker reagents of a lower molecular weight which methods can be amended using standard chemistry knowledge to obtain crosslinker reagents suitable for the present invention. Based on these methods the person skilled in the art is able to apply standard chemical knowledge to obtain the backbone and crosslinker reagents used in the present invention.

The mixture of step (a) comprises a first solvent and at least a second second solvent. Said first solvent is preferably selected from the group comprising dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol and water and mixtures thereof.

The at least one backbone reagent and at least one crosslinker reagent are dissolved in the first solvent, i.e. the disperse phase of the suspension polymerization. In one embodiment the backbone reagent and the crosslinker reagent are dissolved separately, i.e. in different containers, using either the same or different solvent and preferably using the same solvent for both reagents. In another embodiment, the backbone reagent and the crosslinker reagent are dissolved together, i.e. in the same container and using the same solvent.

A suitable solvent for the backbone reagent is an organic solvent. Preferably, the solvent is selected from the group consisting of dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol and water and mixtures thereof. More preferably, the backbone reagent is dissolved in a solvent selected from the group comprising acetonitrile, dimethyl sulfoxide, methanol or mixtures thereof. Most preferably, the backbone reagent is dissolved in dimethylsulfoxide.

In one embodiment the backbone reagent is dissolved in the solvent in a concentration ranging from 1 to 300 mg/ml, more preferably from 5 to 60 mg/ml and most preferably from 10 to 40 mg/ml.

A suitable solvent for the crosslinker reagent is an organic solvent. Preferably, the solvent is selected from the group comprising dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol, water or mixtures thereof. More preferably, the crosslinker reagent is dissolved in a solvent selected from the group comprising dimethylformamide, acetonitrile, dimethyl sulfoxide, methanol or mixtures thereof. Most preferably, the crosslinker reagent is dissolved in dimethylsulfoxide.

In one embodiment the crosslinker reagent is dissolved in the solvent in a concentration ranging from 5 to 500 mg/ml, more preferably from 25 to 300 mg/ml and most preferably from 50 to 200 mg/ml.

The at least one backbone reagent and the at least one crosslinker reagent are mixed in a weight ratio ranging from 1:99 to 99:1, e.g. in a ratio ranging from 2:98 to 90:10, in a weight ratio ranging from 3:97 to 88:12, in a weight ratio ranging from 3:96 to 85:15, in a weight ratio ranging from 2:98 to 90:10 and in a weight ratio ranging from 5:95 to 80:20; particularly preferred in a weight ratio from 5:95 to 80:20, wherein the first number refers to the backbone reagent and the second number to the crosslinker reagent.

Preferably, the ratios are selected such that the mixture of step (a) comprises a molar excess of amine groups from the backbone reagent compared to the activated functional end groups of the crosslinker reagent. Consequently, the hydrogel resulting from the process of the present invention has free amine groups which can be used to couple other moieties to the hydrogel, such as spacers, affinity ligands, chelators and/or reversible prodrug linker moieties.

The at least one second solvent, i.e. the continuous phase of the suspension polymerization, is preferably an organic solvent, more preferably an organic solvent selected from the group comprising linear, branched or cyclic $C_{5-30}$ alkanes; linear, branched or cyclic $C_{5-30}$ alkenes; linear, branched or cyclic $C_{5-30}$ alkynes; linear or cyclic poly (dimethylsiloxanes); aromatic $C_{6-20}$ hydrocarbons; and mixtures thereof. Even more preferably, the at least second solvent is selected from the group comprising linear, branched or cyclic $C_{5-16}$ alkanes; toluene; xylene; mesitylene; hexamethyldisiloxane; or mixtures thereof. Most preferably, the at least second solvent selected from the group comprising linear $C_{7-11}$ alkanes, such as heptane, octane, nonane, decane and undecane.

Preferably, the mixture of step (a) further comprises a detergent. Preferred detergents are Cithrol™ DPHS (PEG-30 dipolyhydroxystearate), Hypermer™ A70, Hypermer™ B246, Hypermer™ 1599A, Hypermer™ 2296, or Hypermer™ 1083. Most preferred is Cithrol™ DPHS (PEG-30 dipolyhydroxystearate).

Preferably, the detergent has a concentration of 0.1 g to 100 g per 1 L total mixture, i.e. disperse phase and continuous phase together. More preferably, the detergent has a concentration of 0.5 g to 10 g per 1 L total mixture, and most preferably, the detergent has a concentration of 0.5 g to 5 g per 1 L total mixture.

Preferably, the mixture of step (a) is an emulsion.

The polymerization in step (b) is initiated by adding a base. Preferably, the base is a non-nucleophilic base soluble in alkanes, more preferably the base is selected from N,N,N',N'-tetramethylethylene diamine (TMEDA), 1,4-dimethylpiperazine, 4-methylmorpholine, 4-ethylmorpholine, 1,4-diazabicyclo[2.2.2]octane, 1,1,4,7,10,10-hexamethyltriethylenetetramine, 1,4,7-trimethyl-1,4,7-triazacyclononane, tris[2-(dimethylamino)ethyl]amine, triethylamine, diisopropylethylamine (DIPEA), trimethylamine, N,N-dimethylethylamine, N,N,N',N'-tetramethyl-1,6-hexanediamine, N,N,N',N'',N''-pentamethyldiethylenetriamine, 1,8-diazabicyclo[5.4.0]undec-7-ene, 1,5-diazabicyclo[4.3.0]non-5-ene, and hexamethylenetetramine. Even more preferably, the base is selected from TMEDA, 1,4-dimethylpiperazine, 4-methylmorpholine, 4-ethylmorpholine, 1,4-diazabicyclo[2.2.2]octane, 1,1,4,7,10,10-hexamethyltriethylenetetramine, 1,4,7-trimethyl-1,4,7-triazacyclononane, tris[2-(dimethylamino)ethyl]amine, 1,8-diazabicyclo[5.4.0]undec-7-ene, 1,5-diazabicyclo[4.3.0] non-5-ene, and hexamethylenetetramine. Most preferably, the base is TMEDA.

The base is added to the mixture of step (a) in an amount of 1 to 500 equivalents per activated functional end group in the mixture, preferably in an amount of 5 to 50 equivalents, more preferably in an amount of 5 to 25 equivalents and most preferably in an amount of 10 equivalents.

In process step (b), the polymerization of the hydrogel of the present invention is a condensation reaction, which preferably occurs under continuous stirring of the mixture of step (a). Preferably, the tip speed (tip speed=π×stirrer rotational speed×stirrer diameter) ranges from 0.2 to 10 meter per second (m/s), more preferably from 0.5 to 4 m/s and most preferably from 1 to 2 m/s.

In a preferred embodiment of step (b), the polymerization reaction is carried out in a cylindrical vessel equipped with baffles. The diameter to height ratio of the vessel may range from 4:1 to 1:2, more preferably the diameter to height ratio of the vessel ranges from 2:1 to 1:1.

Preferably, the reaction vessel is equipped with an axial flow stirrer selected from the group comprising pitched blade stirrer, marine type propeller, or Lightnin A-310. More preferably, the stirrer is a pitched blade stirrer.

Step (b) can be performed in a broad temperature range, preferably at a temperature from −10° C. to 100 Co, more preferably at a temperature of 0° C. to 80° C., even more preferably at a temperature of 10° C. to 50° C. and most preferably at ambient temperature. "Ambient temperature" refers to the temperature present in a typical laboratory environment and preferably means a temperature ranging from 17 to 25° C.

Preferably, the hydrogel obtained from the polymerization is a shaped article, such as a coating, mesh, stent, nanoparticle or a microparticle. More preferably, the hydrogel is in the form of microparticular beads having a diameter from 1 to 500 micrometer, more preferably with a diameter from 10 to 300 micrometer, even more preferably with a diameter from 20 and 150 micrometer and most preferably with a diameter from 30 to 130 micrometer. The afore-mentioned diameters are measured when the hydrogel microparticles are fully hydrated in water.

In one embodiment, the process for the preparation of a hydrogel of the present invention further comprises the step of:
(c) working-up the hydrogel.

Step (c) comprises one or more of the following step(s):
(c1) removing excess liquid from the polymerization reaction,
(c2) washing the hydrogel to remove solvents used during polymerization,
(c3) transferring the hydrogel into a buffer solution,
(c4) size fractionating/sieving of the hydrogel,
(c5) transferring the hydrogel into a container,
(c6) drying the hydrogel,
(c7) transferring the hydrogel into a specific solvent suitable for sterilization, and
(c8) sterilizing the hydrogel, preferably by gamma radiation Preferably, step (c) comprises all of the following steps (c1) removing excess liquid from the polymerization reaction,
(c2) washing the hydrogel to remove solvents used during polymerization,
(c3) transferring the hydrogel into a buffer solution,
(c4) size fractionating/sieving of the hydrogel,
(c5) transferring the hydrogel into a container,
(c7) transferring the hydrogel into a specific solvent suitable for sterilization, and
(c8) sterilizing the hydrogel, preferably by gamma radiation.

The Backbone Reagent

The at least one backbone reagent has a molecular weight ranging from 1 to 100 kDa, preferably from 2 to 50 kDa, more preferably from 5 and 30 kDa, even more preferably from 5 to 25 kDa and most preferably from 5 to 15 kDa.

Preferably, the backbone reagent is PEG-based comprising at least 10% PEG, more preferably comprising at least 20% PEG, even more preferably comprising at least 30% PEG and most preferably comprising at least 40% PEG.

In one embodiment the backbone reagent is present in the form of its acidic salt, preferably in the form of an acid addition salt. Suitable acid addition salts are formed from acids which form non-toxic salts. Examples include but are not limited to the acetate, aspartate, benzoate, besylate, bicarbonate, carbonate, bisulphate, sulphate, borate, camsylate, citrate, edisylate, esylate, formate, fumarate, gluceptate, gluconate, glucuronate, hexafluorophosphate, hibenzate, hydrochloride, hydrobromide, hydroiodide, isethionate, lactate, malate, maleate, malonate, mesylate, methylsulphate, naphthylate, nicotinate, nitrate, orotate, oxalate, palmitate, pamoate, phosphate, hydrogen phosphate, dihydrogen phosphate, sacharate, stearate, succinate, tartrate and tosylate. Particularly preferred, the backbone reagent is present in the form of its hydrochloride salt.

In one embodiment, the at least one backbone reagent is selected from the group consisting of
a compound of formula (I)

$$B(-(A^0)_{x1}-(SP)_{x2}-A^1-P-A^2-Hyp^1)_x \qquad (I),$$

wherein
B is a branching core,
SP is a spacer moiety selected from the group consisting of $C_{1-6}$ alkyl, $C_{2-6}$ alkenyl and $C_{2-6}$ alkynyl,
P is a PEG-based polymeric chain comprising at least 80% PEG, preferably at least 85% PEG, more preferably at least 90% PEG and most preferably at least 95% PEG,
$Hyp^1$ is a moiety comprising an amine (—$NH_2$ and/or —NH—) or a polyamine comprising at least two amines (—$NH_2$ and/or —NH—),
x is an integer from 3 to 16,
x1, x2 are independently of each other 0 or 1, provided that x1 is 0, if x2 is 0,
$A^0$, $A^1$, $A^2$ are independently of each other selected from the group consisting of

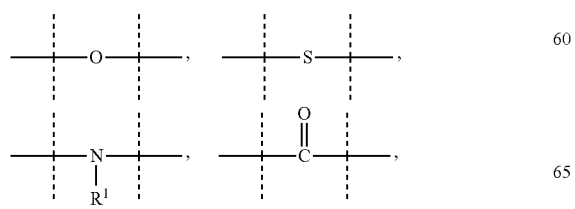

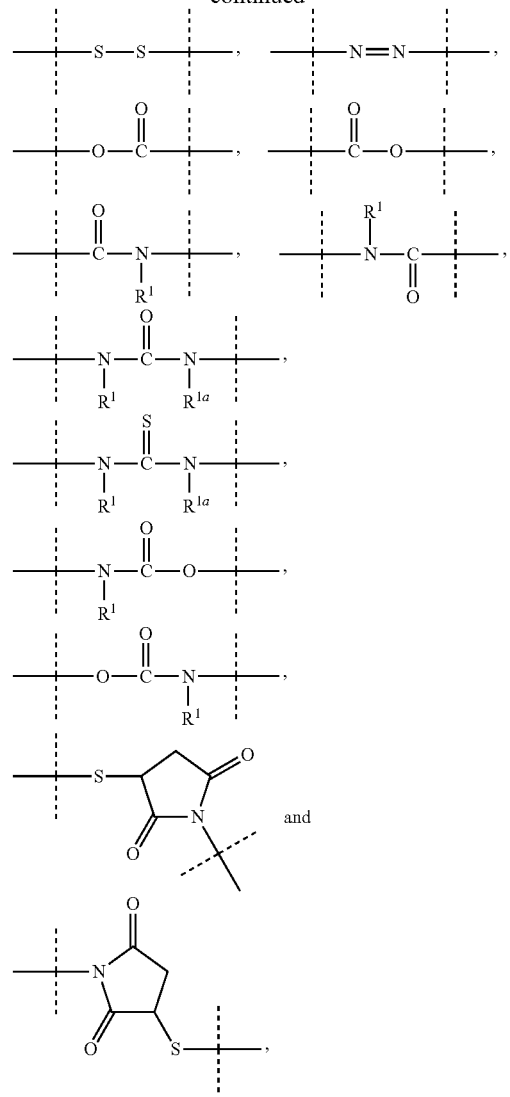

wherein $R^1$ and $R^{1a}$ are independently of each other selected from H and $C_{1-6}$ alkyl;
a compound of formula (II)

$$Hyp^2-A^3-P-A^4-Hyp^3 \qquad (II),$$

wherein
P is defined as above in the compound of formula (I),
$Hyp^2$, $Hyp^3$ are independently of each other a polyamine comprising at least two amines (—$NH_2$ and/or —NH—), and
$A^3$ and $A^4$ are independently selected from the group consisting of

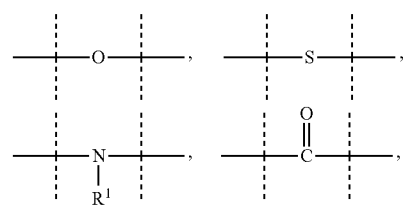

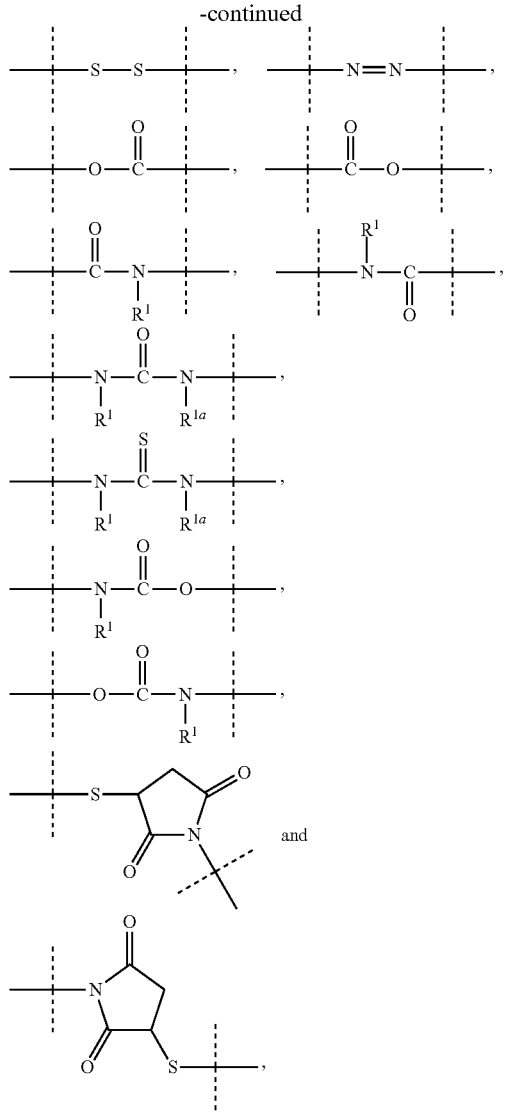

wherein $R^1$ and $R^{1a}$ are independently of each other selected from H and $C_{1-6}$ alkyl;

a compound of formula (III)

$$P^1\text{-}A^5\text{-}Hyp^4 \qquad (III),$$

wherein $P^1$ is a PEG-based polymeric chain comprising at least 80% PEG, preferably at least 85% PEG, more preferably at least 90% PEG and most preferably at least 95% PEG, $Hyp^4$ is a polyamine comprising at least three amines (—$NH_2$ and/or —NH), and $A^5$ is selected from the group consisting of wherein $R^1$ and $R^{1a}$ are independently of each other selected from H and $C_{1-6}$ alkyl;

and a compound of formula (IV), $$T^1\text{-}A^6\text{-}Hyp^5 \qquad (IV),$$

wherein $Hyp^5$ is a polyamine comprising at least three amines (—$NH_2$ and/or —NH), and $A^6$ is selected from the group consisting of

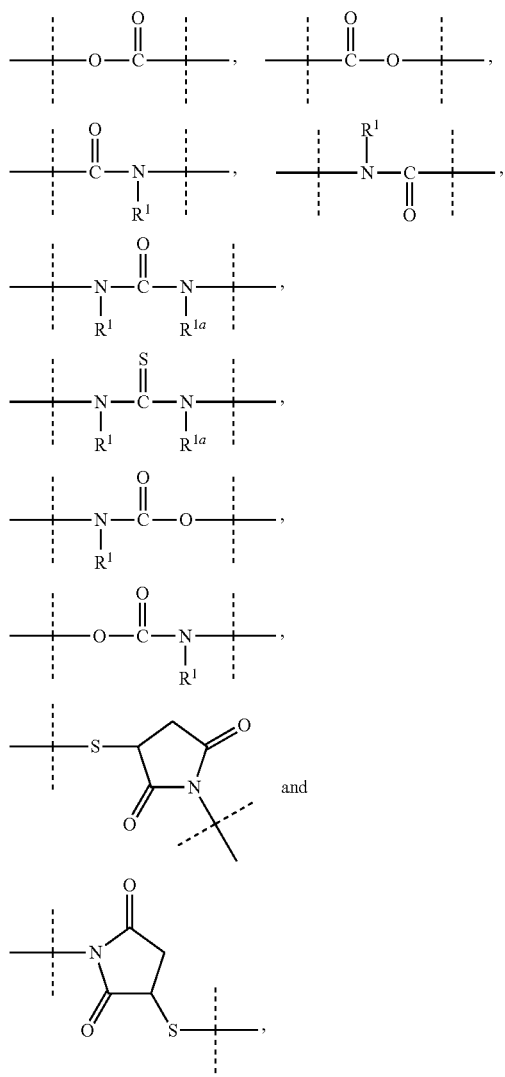

wherein R¹ and R¹ᵃ are independently of each other selected from H and $C_{1-6}$ alkyl; and T¹ is selected from the group consisting of $C_{1-50}$ alkyl, $C_{2-50}$ alkenyl or $C_{2-50}$ alkynyl, which fragment is optionally interrupted by one or more group(s) selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4- to 7-membered heterocyclyl, phenyl or naphthyl.

In the following sections the term "Hyp$^x$" refers to Hyp¹, Hyp², Hyp³, Hyp⁴ and Hyp⁵ collectively.

Preferably, the backbone reagent is a compound of formula (I), (II) or (III), more preferably the backbone reagent is a compound of formula (I) or (III), and most preferably the backbone reagent is a compound of formula (I).

In a preferred embodiment, in a compound of formula (I), x is 4, 6 or 8. Preferably, in a compound of formula (I) x is 4 or 8, most preferably, x is 4.

In a preferred embodiment in the compounds of formula (I) to (IV), A⁰, A¹, A², A³, A⁴, A⁵ and A⁶ are selected from the group comprising

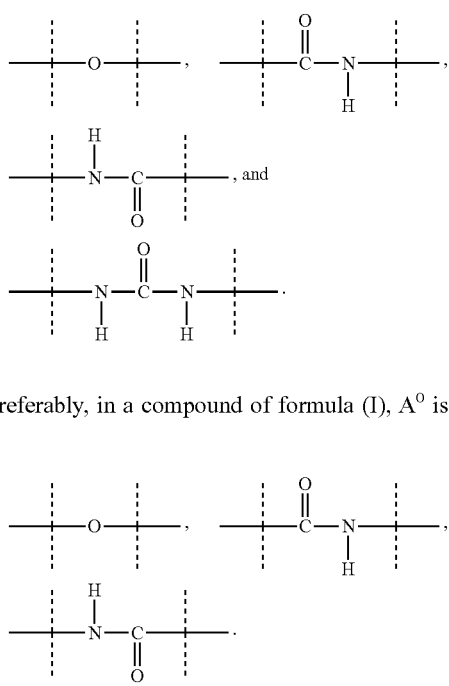

Preferably, in a compound of formula (I), A⁰ is

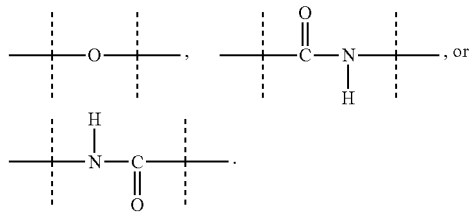

Preferably, in a compound of formula (I), A¹ is

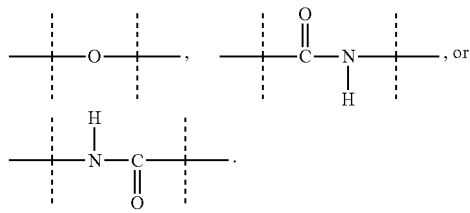

Preferably, in a compound of formula (I), A² is

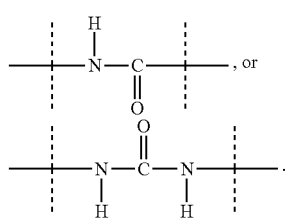

Preferably, in a compound of formula (II), A³ is

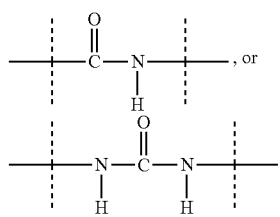

and A⁴ is
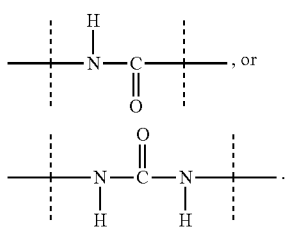, or
Preferably, in a compound of formula (III), A⁵ is
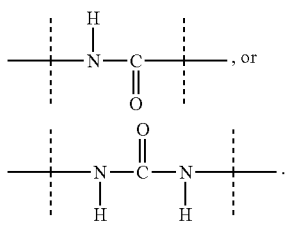, or
Preferably, in a compound of formula (IV), A⁶ is
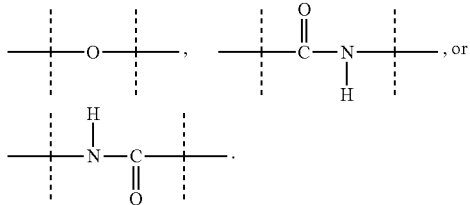
Preferably, in a compound of formula (IV), $T^1$ is selected from H and $C_{1-6}$ alkyl.
In one embodiment, in a compound of formula (I), the branching core B is selected from the following structures:
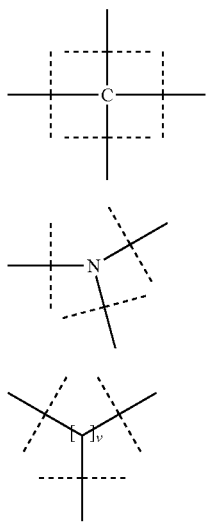
(a-i)
(a-ii)
(a-iii)
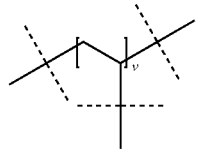
(a-iv)
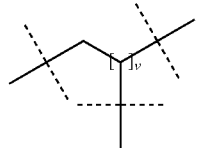
(a-v)
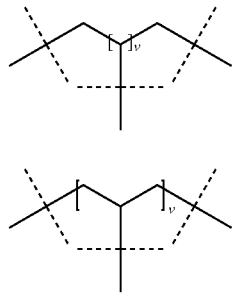
(a-vi)
(a-vii)
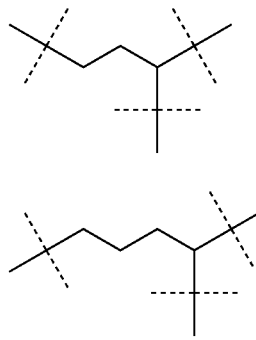
(a-viii)
(a-ix)
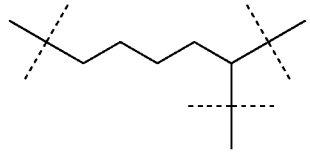
(a-x)
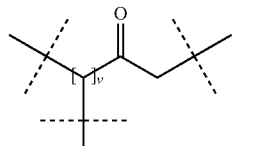
(a-xi)
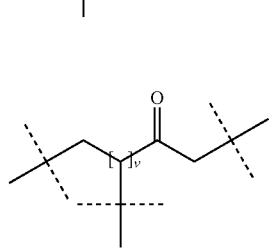
(a-xii)

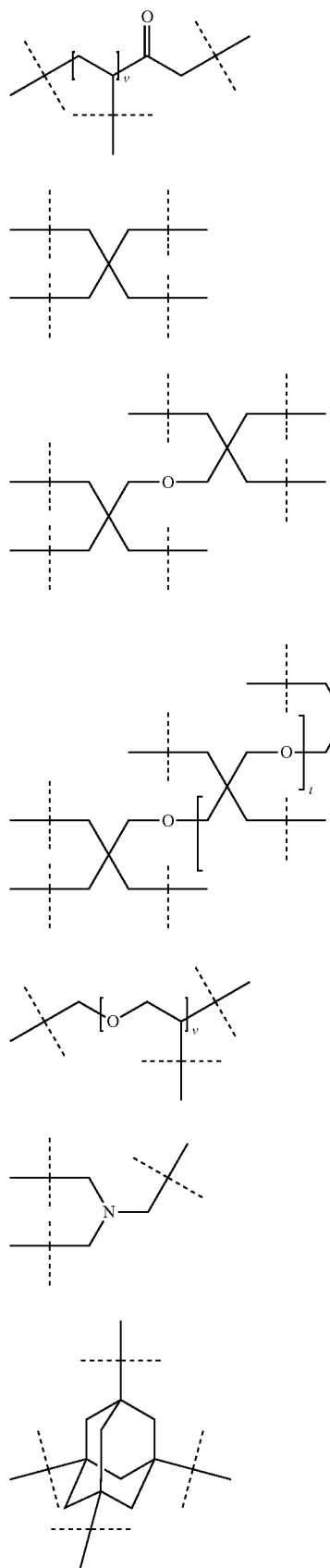
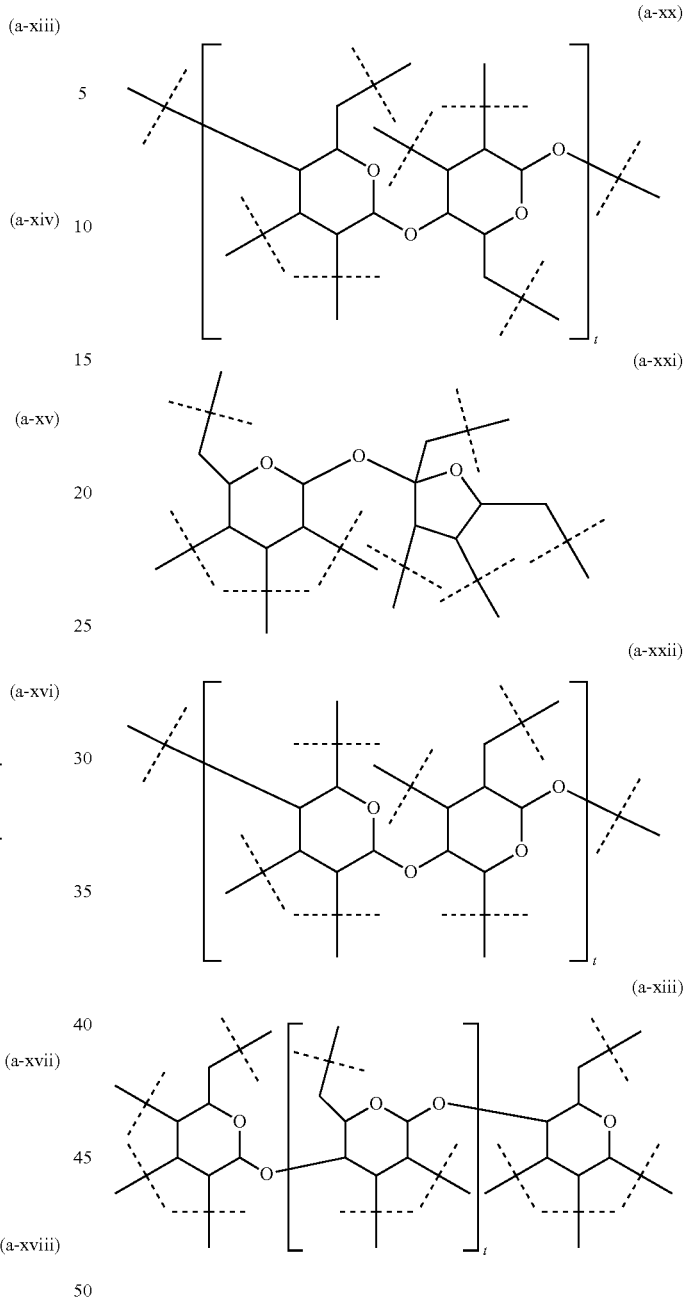

wherein
dashed lines indicate attachment to $A^0$ or, if x1 and x2 are both 0, to $A^1$,
t is 1 or 2; preferably t is 1,
v is 1, 2, 3, 4, 5, 6, 7, 8, 9, 10, 11, 12, 13 or 14; preferably, v is 2, 3, 4, 5, 6; more preferably, v is 2, 4 or 6; most preferably, v is 2.

In a preferred embodiment, B has a structure of formula (a-i), (a-ii), (a-iii), (a-iv), (a-v), (a-vi), (a-vii), (a-viii), (a-ix), (a-x), (a-xiv) or (a-xv). More preferably, B has a structure of formula (a-iii), (a-iv), (a-v), (a-vi), (a-vii), (a-viii), (a-ix), (a-x) or (a-iv). Most preferably, B has a structure of formula (a-xiv).

A preferred embodiment is a combination of B and $A^0$, or, if x1 and x2 are both 0 a preferred combination of B and $A^1$, which is selected from the following structures:

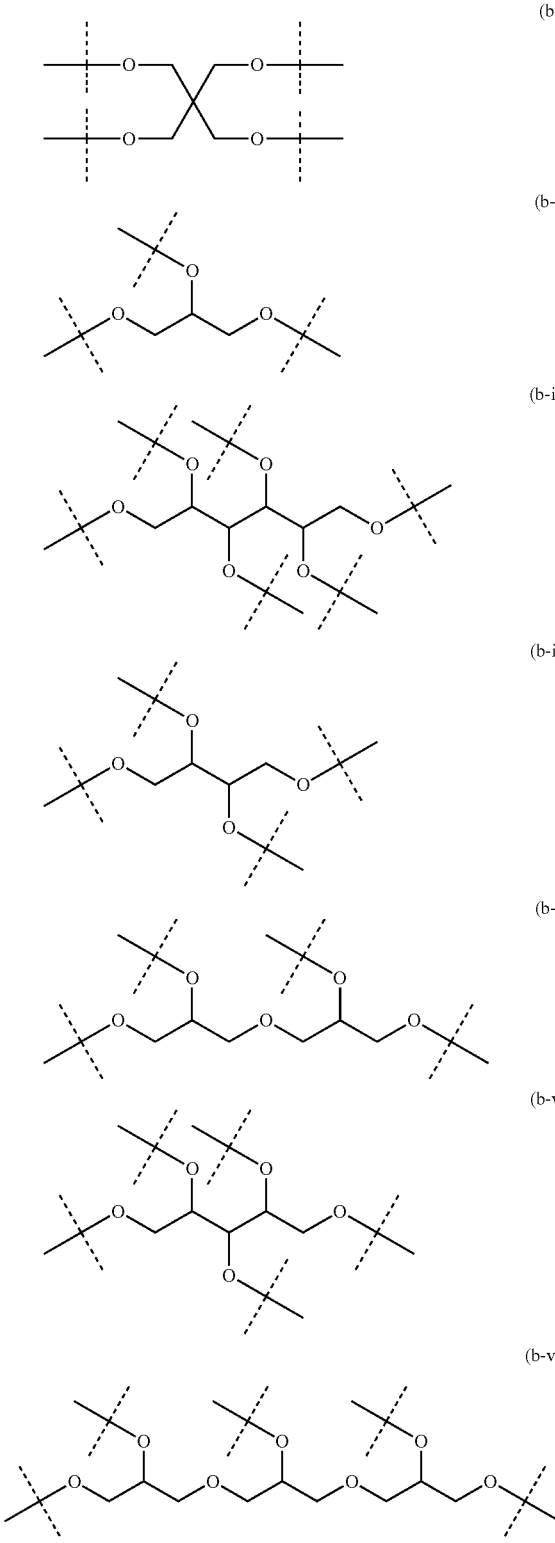

wherein
dashed lines indicate attachment to SP or, if x1 and x2 are both 0, to P.

More preferably, the combination of B and A⁰ or, if x1 and x2 are both 0, the combination of B and A¹, has a structure of formula of formula (b-i), (b-iv), (b-vi) or (b-viii) and most preferably has a structure of formula of formula (b-i).

In one embodiment, x1 and x2 of formula (I) are 0.

In one embodiment, the PEG-based polymeric chain P has a molecular weight from 0.3 kDa to 40 kDa; e.g. from 0.4 to 35 kDa, from 0.6 to 38 kDa, from 0.8 to 30 kDa, from 1 to 25 kDa, from 1 to 15 kDa or from 1 to 10 kDa. Most preferably P has a molecular weight from 1 to 10 kDa.

In one embodiment, the PEG-based polymeric chain $P^1$ has a molecular weight from 0.3 kDa to 40 kDa; e.g. from 0.4 to 35 kDa, from 0.6 to 38 kDA, from 0.8 to 30 kDa, from 1 to 25 kDa, from 1 to 15 kDa or from 1 to 10 kDa. Most preferably $P^1$ has a molecular weight from 1 to 10 kDa.

In one embodiment, in the compounds of formulas (I) or (II), P has the structure of formula (c-i):

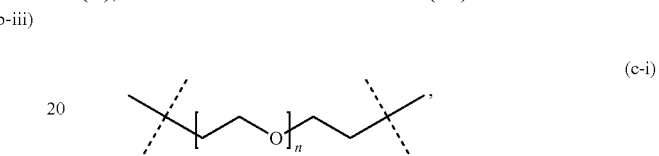

(c-i)

wherein n ranges from 6 to 900, more preferably n ranges from 20 to 700 and most preferably n ranges from 20 to 250.

In one embodiment, in the compounds of formulas (III), $P^1$ has the structure of formula (c-ii): (c-ii),

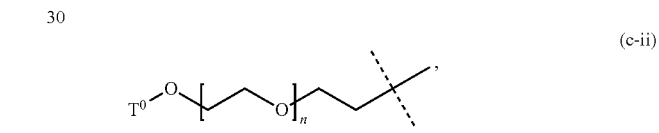

(c-ii)

wherein
n ranges from 6 to 900, more preferably n ranges from 20 to 700 and most preferably n ranges from 20 to 250;
$T^0$ is selected from the group comprising $C_{1-6}$ alkyl, $C_{2-6}$ alkenyl and $C_{2-6}$ alkynyl, which is optionally interrupted by one or more group(s) selected from —NH—, —N($C_{1-4}$ alkyl)-, —O—, —S—, —C(O)—, —C(O)NH—, —C(O)N($C_{1-4}$ alkyl)-, —O—C(O)—, —S(O)— or —S(O)$_2$—.

In one embodiment, in the compounds of formulas (I) to (IV), the moiety $Hyp^x$ is a polyamine and preferably comprises in bound form and, where applicable, in R- and/or S-configuration a moiety of the formulas (d-i), (d-ii), (d-iii) and/or (d-iv):

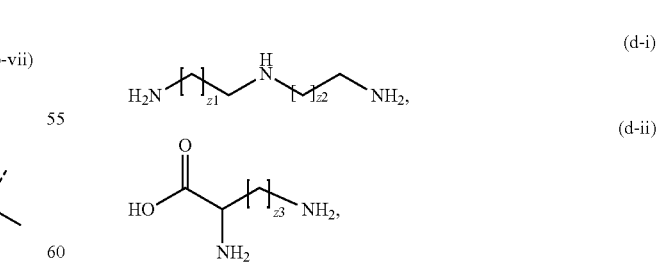

-continued (d-iv)

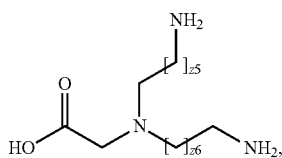

wherein z1, z2, z3, z4, z5, z6 are independently of each other 1, 2, 3, 4, 5, 6, 7 or 8.

More preferably, $Hyp^x$ comprises in bound form and in R- and/or S-configuration lysine, ornithine, diaminoproprionic acid and/or diaminobutyric acid. Most preferably, $Hyp^x$ comprises in bound form and in R- and/or S-configuration lysine.

$Hyp^x$ has a molecular weight from 40 Da to 30 kDa, preferably from 0.3 kDa to 25 kDa, more preferably from 0.5 kDa to 20 kDa, even more preferably from 1 kDa to 20 kDa and most preferably from 2 kDa to 15 kDa.

$Hyp^x$ is preferably selected from the group consisting of a moiety of formula (e-i)

(e-i)

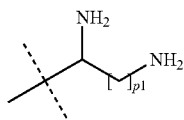

wherein p1 is an integer from 1 to 5, preferably p1 is 4, and the dashed line indicates attachment to $A^2$ if the backbone reagent has a structure of formula (I) and to $A^3$ or $A^4$ if the backbone reagent has the structure of formula (II);

a moiety of formula (e-ii)

(e-ii)

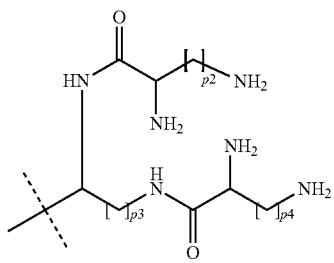

wherein p2, p3 and p4 are identical or different and each is independently of the others an integer from 1 to 5, preferably p2, p3 and p4 are 4, and the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III) and to $A^6$ if the backbone reagent has a structure of formula (IV);

a moiety of formula (e-iii)

(e-iii)

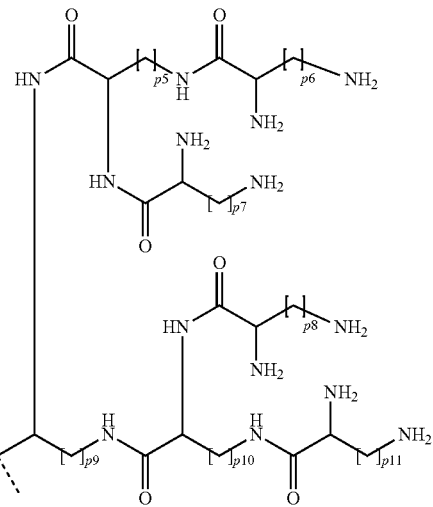

wherein p5 to p11 are identical or different and each is independently of the others an integer from 1 to 5, preferably p5 to p11 are 4, and the dashed line indicates attachment to $A^2$ if the backbone reagent is of formula (I), to $A^3$ or $A^4$ if the backbone reagent is of formula (II), to A5 if the backbone reagent is of formula (III) and to $A^6$ if the backbone reagent is of formula (IV);

a moiety of formula (e-iv)

(e-iv)

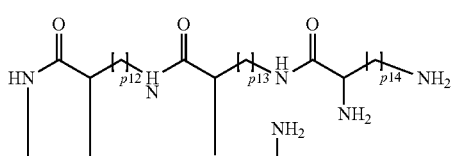

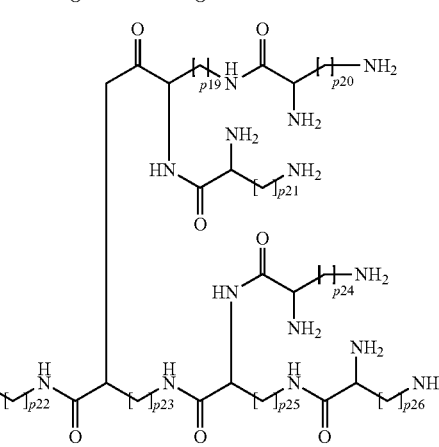

wherein p12 to p26 are identical or different and each is independently of the others an integer from 1 to 5, preferably p12 to p26 are 4, and the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III) and to $A^6$ if the backbone reagent has a structure of formula (IV);

a moiety of formula (e-v)

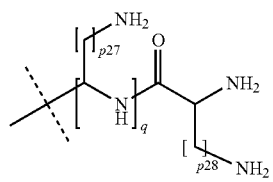

(e-v)

wherein p27 and p28 are identical or different and each is independently of the other an integer from 1 to 5, preferably p27 and p28 are 4, q is an integer from 1 to 8, preferably q is 2 or 6 and most preferably q is 6, and the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III) and to $A^6$ if the backbone reagent has a structure of formula (IV);

a moiety of formula (e-vi)

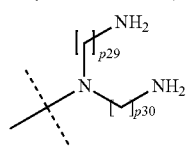

(e-vi)

wherein p29 and p30 are identical or different and each is independently of the other an integer from 2 to 5, preferably p29 and p30 are 3, and the dashed line indicates attachment to $A^2$ if the backbone reagent has the structure of formula (I), to $A^3$ or $A^4$ if the backbone reagent has the structure of formula (II), to $A^5$ if the backbone reagent has the structure of formula (III) and to $A^6$ if the backbone reagent has the structure of formula (IV);

a moiety of formula (e-vii)

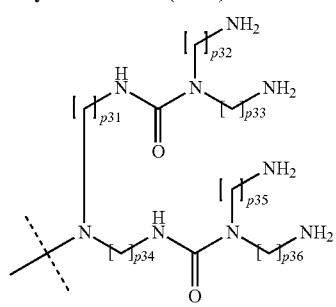

(e-vii)

wherein p31 to p36 are identical or different and each is independently of the others an integer from 2 to 5, preferably p31 to p36 are 3, and the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III) and to $A^6$ if the backbone reagent has a structure of formula (IV);

a moiety of formula (e-viii)

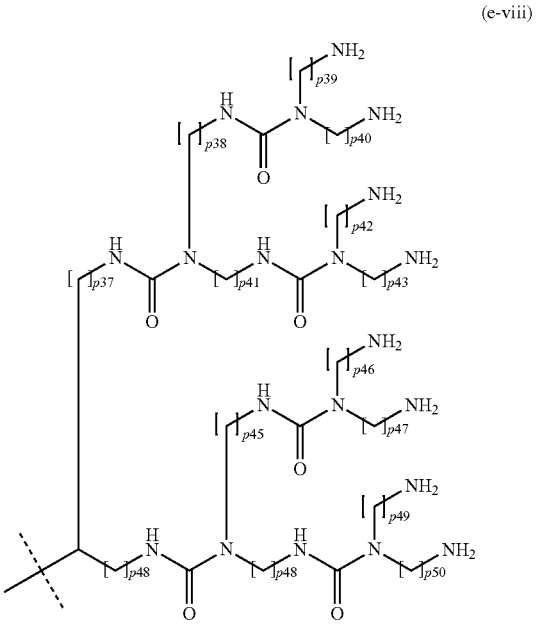

(e-viii)

wherein p37 to p50 are identical or different and each is independently of the others an integer from 2 to 5, preferably p37 to p50 are 3, and the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III) and to $A^6$ if the backbone reagent has a structure of formula (IV); and a moiety of formula (e-ix):

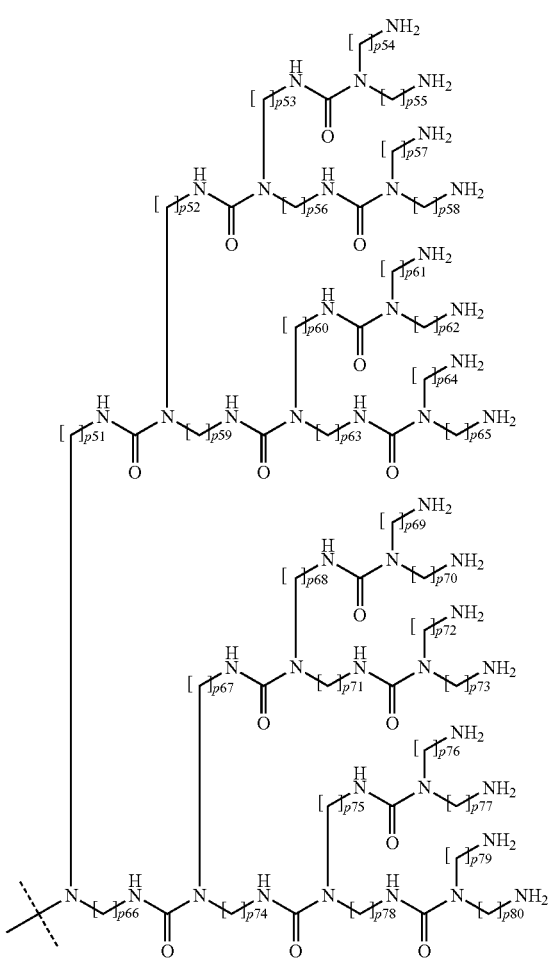

(e-ix)

wherein
p51 to p80 are identical or different and each is independently of the others an integer from 2 to 5, preferably p51 to p80 are 3, and
the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III) and to $A^6$ if the backbone reagent has a structure of formula (IV); and wherein the moieties (e-i) to (e-v) may at each chiral center be in either R- or S-configuration, preferably, all chiral centers of a moiety (e-i) to (e-v) are in the same configuration.

Preferably, $Hyp^x$ is has a structure of formulas (e-i), (e-ii), (e-iii), (e-iv), (e-vi), (e-vii), (e-viii) or (e-ix). More preferably, $Hyp^x$ has a structure of formulas (e-ii), (e-iii), (e-iv), (e-vii), (e-viii) or (e-ix), even more preferably $Hyp^x$ has a structure of formulas (e-ii), (e-iii), (e-vii) or (e-viii) and most preferably $Hyp^x$ has the structure of formula (e-iii).

If $Hyp^x$ comprises in bound form lysine, it is preferred that it comprises D-lysine, because it was surprisingly found that hydrogels comprising backbone moieties comprising D-lysine—as opposed to those comprising L-lysine—are more stable when administered to a patient.

If the backbone reagent has a structure of formula (I), a preferred moiety-$A^2$-$Hyp^1$ is a moiety of the formula

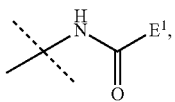

wherein
the dashed line indicates attachment to P; and
E1 is selected from formulas (e-i) to (e-ix).

If the backbone reagent has a structure of formula (II) a preferred moiety $Hyp^2$-$A^3$- is a moiety of the formula

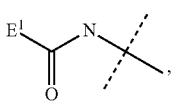

wherein
the dashed line indicates attachment to P; and
$E^1$ is selected from formulas (e-i) to (e-ix);
and a preferred moiety -$A^4$-$Hyp^3$ is a moiety of the formula

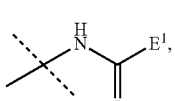

wherein
the dashed line indicates attachment to P; and
$E^1$ is selected from formulas (e-i) to (e-ix).

If the backbone reagent has a structure of formula (III), a preferred moiety -$A^5$-$Hyp^4$ is a moiety of the formula

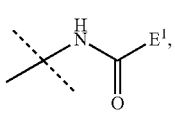

wherein
the dashed line indicates attachment to $P^1$; and
$E^1$ is selected from formulas (e-i) to (e-ix).

More preferably, the backbone reagent has a structure of formula (I) and B is has a structure of formula (a-xiv).

Even more preferably, the backbone reagent has the structure of formula (I), B has the structure of formula (a-xiv), x1 and x2 are 0, and $A^1$ is —O—.

Even more preferably, the backbone reagent has the structure of formula (I), B has the structure of formula (a-xiv), $A^1$ is —O—, and P has a structure of formula (c-i).

Even more preferably, the backbone reagent is of formula (I), B is of formula (a-xiv), x1 and x2 are 0, $A^1$ is —O— and P is of formula (c-i).

Even more preferably, the backbone reagent is formula (I), B is of formula (a-xiv), x1 and x2 are 0, $A^1$ is —O—, P is of formula (c-i), $A^2$ is —NH—(C=O)— and $Hyp^1$ is of formula (e-iii).

Most preferably, the backbone reagent has the following formula:

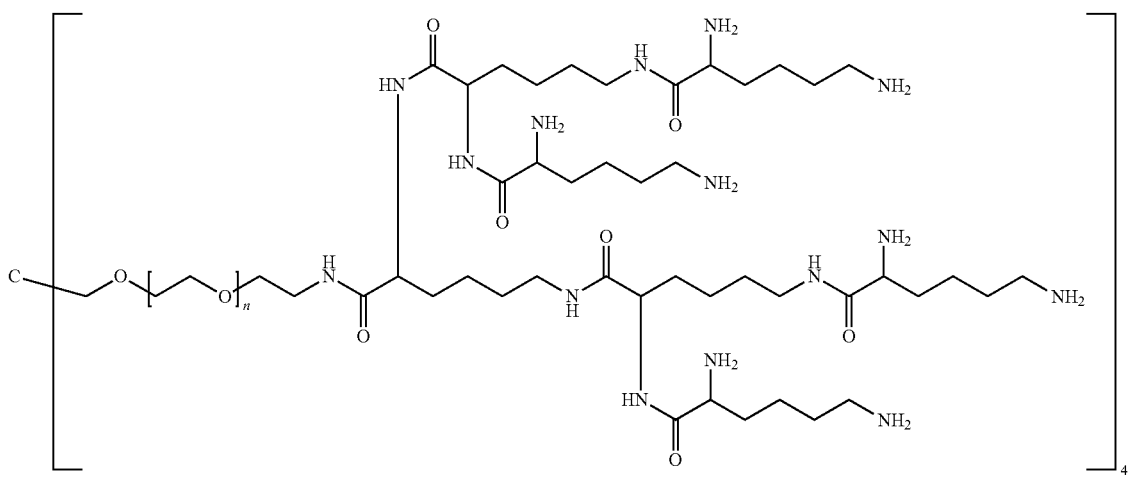

wherein
n ranges from 10 to 40, preferably from 10 to 30, more preferably from 10 to 20.

Equally preferably, n ranges from 20 to 30 kDa and most preferably n is 28.

SP of formula (I) is a spacer moiety selected from the group comprising $C_{1-6}$ alkyl, $C_{2-6}$ alkenyl and $C_{2-6}$ alkynyl, preferably SP is —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, —CH=CH— or —CH=CH—, most preferably SP is —$CH_2$—, —$CH_2$—$CH_2$— or —CH=CH—.

The Crosslinker Reagent

The at least one crosslinker reagent comprises at least two carbonyloxy groups (—(C=O)—O— or —O—(C=O)—), which are biodegradable linkages. These biodegradable linkages are necessary to render the hydrogel biodegradable. Additionally, the at least one crosslinker reagent comprises at least two activated functional end groups which during the polymerization of step (b) react with the amines of the at least one backbone reagent.

The crosslinker reagent has a molecular weight ranging from 6 to 40 kDa, more preferably ranging from 6 to 30 kDa, even more preferably ranging from 6 to 20 kDa, even more preferably ranging from 6 to 15 kDa and most preferably ranging from 6 to 10 kDa.

The crosslinker reagent comprises at least two activated functional end groups selected from the group comprising activated ester groups, activated carbamate groups, activated carbonate groups and activated thiocarbonate groups, which during polymerization react with the amine groups of the backbone reagents, forming amide bonds, i.e. a backbone moiety and a crosslinker moiety are preferably connected through an amide linkage.

In one preferred embodiment, the crosslinker reagent is a compound of formula (V-I):

wherein
each $D^1$, $D^2$, $D^3$ and $D^4$ are identical or different and each is independently of the others selected from the group comprising —O—, —$NR^5$—, —S— and —$CR^6R^{6a}$—;
each $R^1$, $R^{1a}$, $R^2$, $R^{2a}$, $R^3$, $R^{3a}$, $R^4$, $R^{4a}$, $R^6$ and $R^{6a}$ are identical or different and each is independently of the others selected from the group comprising —H, —$OR^7$, —$NR^7R^{7a}$, —$SR^7$ and $C_{1-6}$ alkyl; optionally, each of the pair(s) $R^1/R^2$, $R^3/R^4$, $R^{1a}/R^{2a}$, and $R^{3a}/R^{4a}$ may independently form a chemical bond and/or each of the pairs $R^1/R^{1a}$, $R^2/R^{2a}$, $R^3/R^{3a}$, $R^4/R^{4a}$, $R^6/R^{6a}$, $R^1/R^2$, $R^3/R^4$, $R^{1a}/R^{2a}$, and $R^{3a}/R^{4a}$ are independently of each other joined together with the atom to which they are attached to form a $C_{3-8}$ cycloalkyl or to form a ring A or are joined together with the atom to which they are attached to form a 4- to 7-membered heterocyclyl or 8- to 11-membered heterobicyclyl or adamantyl;
each $R^5$ is independently selected from —H and $C_{1-6}$ alkyl; optionally, each of the pair(s) $R^1/R^5$, $R^2/R^5$, $R^3/R^5$, $R^4/R^5$ and $R^5/R^6$ may independently form a chemical bond and/or are joined together with the atom to which they are attached to form a 4- to 7-membered heterocyclyl or 8- to 11-membered heterobicyclyl;
each $R^7$, $R^{7a}$ is independently selected from H and $C_{1-6}$ alkyl;
A is selected from the group consisting of indenyl, indanyl and tetralinyl;
$P^2$ is

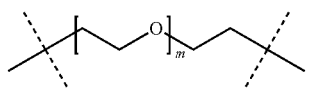

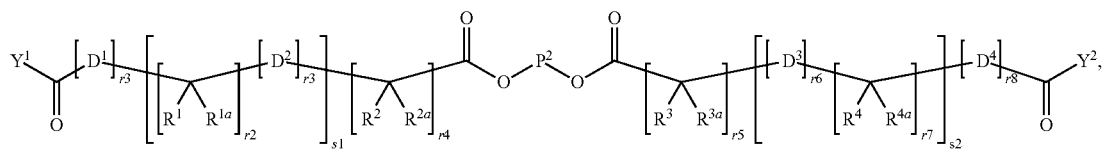

(V-I)

m ranges from 120 to 920, preferably from 120 to 460 and more preferably from 120 to 230, r1, r2, r7, r8 are independently 0 or 1;
r3, r6 are independently 0, 1, 2, 3, or 4;
r4, r5 are independently 1, 2, 3, 4, 5, 6, 7, 8, 9 or 10;
s1, s2 are independently 1, 2, 3, 4, 5 or 6;
$Y^1$, $Y^2$ are identical or different and each is independently of the other selected from formulas (f-i) to (f-vi):

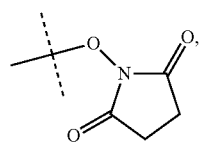

(f-i)

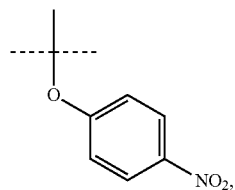

(f-ii)

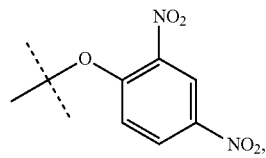

(f-iii)

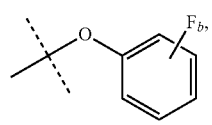

(f-iv)

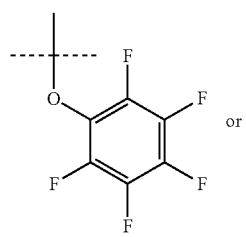

(f-v)

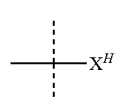

(f-vi)

wherein
the dashed lines indicate attachment to the rest of the molecule,
b is 1, 2, 3 or 4
$X^H$ is Cl, Br, I, or F.

Preferably, the crosslinker reagent is a compound of formula (V-II):

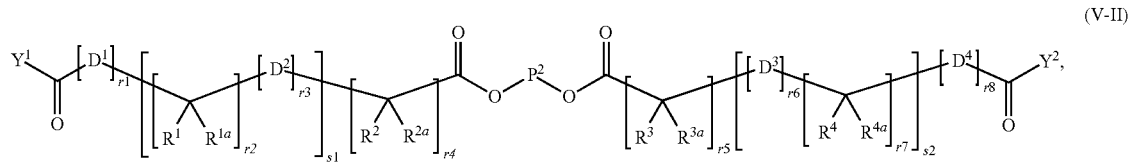

(V-II)

wherein
$D^1$, $D^2$, $D^3$ and $D^4$ are identical or different and each is independently of the others selected from the group comprising —O—, —$NR^5$—, —S— and —$CR^5R^{5a}$—;
$R^1$, $R^{1a}$, $R^2$, $R^{2a}$, $R^3$, $R^{3a}$, $R^4$, $R^{4a}$, $R^5$ and $R^{5a}$ are identical or different and each is independently of the others selected from the group comprising H and $C_{1-6}$ alkyl; optionally, one or more of the pair(s) $R^1/R^{1a}$, $R^2/R^{2a}$, $R^3/R^{3a}$, $R^4/R^{4a}$, $R^1/R^2$, $R^3/R^4$, $R^{1a}/R^{2a}$, and $R^{3a}/R^{4a}$ form a chemical bond or are joined together with the atom to which they are attached to form a $C_{3-8}$ cycloalkyl or to form a ring A or are joined together with the atom to which they are attached to form a 4- to 7-membered heterocyclyl or 8- to 11-membered heterobicyclyl or adamantyl;
A is selected from the group consisting of phenyl, naphthyl, indenyl, indanyl and tetralinyl;
$P^2$ is

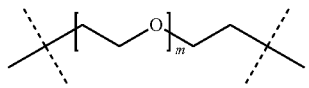

m ranges from 120 to 920, preferably from 120 to 460 and more preferably from 120 to 230,
r1, r2, r7, r8 are independently 0 or 1;
r3, r6 are independently 0, 1, 2, 3, or 4;
r4, r5 are independently 1, 2, 3, 4, 5, 6, 7, 8, 9 or 10;
s1, s2 are independently 1, 2, 3, 4, 5 or 6;
$Y^1$, $Y^2$ are identical or different and each is independently of the other selected from formulas (f-i) to (f-vi):

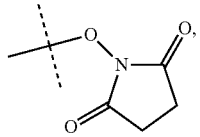

(f-i)

(f-ii)

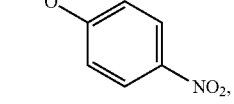

(f-iii)

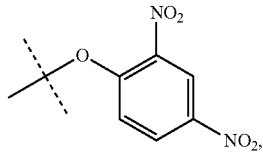

-continued (f-iv)
(f-v)
(f-vi)

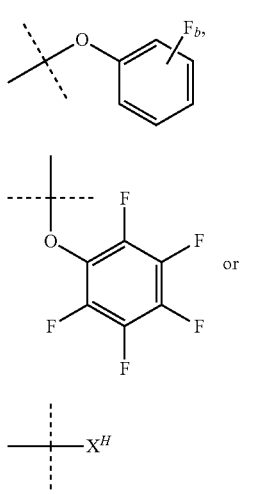

wherein
the dashed lines indicate attachment to the rest of the molecule,
b is 1, 2, 3 or 4
$X^H$ is Cl, Br, I, or F.

It is understood that the moieties

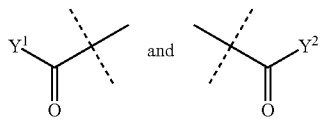

represent the at least two activated functional end groups.

Preferably, $Y^1$ and $Y^2$ of formula (V-I) and (V-II) have a structure of formula (f-i), (f-ii) or (f-v). More preferably, $Y^1$ and $Y^2$ have a structure of formula (f-i) or (f-ii) and most preferably, $Y^1$ and $Y^2$ have a structure of formula (f-i).

Preferably, both moieties $Y^1$ and $Y^2$ of formula (V-I) and (V-II) have the same structure. More preferably, both moieties $Y^1$ and $Y^2$ have the structure of formula (f-i).

Preferably, r1 of formula (V-I) and (V-II) is 0.
Preferably, r1 and s1 of formula (V-I) and (V-II) are both 0.

Preferably, one or more of the pair(s) $R^1/R^{1a}$, $R^2/R^{2a}$, $R^3/R^{3a}$, $R^4/R^{4a}$, $R^1/R^2$, $R^3/R^4$, $R^{1a}/R^{2a}$, and $R^{3a}/R^{4a}$ of formula (V-I) and (V-II) form a chemical bond or are joined together with the atom to which they are attached to form a $C_{3-8}$ cycloalkyl or form a ring A.

Preferably, one or more of the pair(s) $R^1/R^2$, $R^{1a}/R^{2a}$, $R^3/R^4$, $R^{3a}/R^{4a}$ of formula (V-I) and (V-II) are joined together with the atom to which they are attached to form a 4- to 7-membered heterocyclyl or 8- to 11-membered heterobicyclyl.

Preferably, the crosslinker reagent of formula (V-I) and (V-II) is symmetric, i.e. the moiety

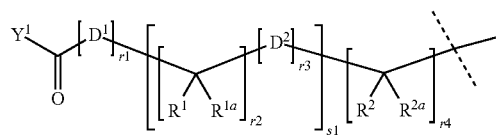

has the same structure as the moiety

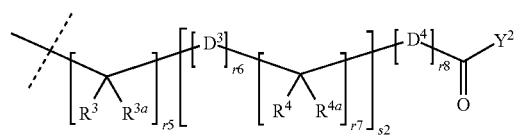

In one preferred embodiments s1, s2, r1 and r8 of formula (V-I) and (V-II) are 0.

In another preferred embodiment s1, s2, r1 and r8 of formula (V-I) and (V-II) are 0 and r4 of formula (V-I) and (V-II) and r5 are 1.

Preferred crosslinker reagents are of formula (V-1) to (V-54):

(V-1)
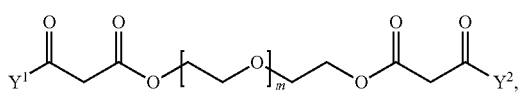

(V-2)
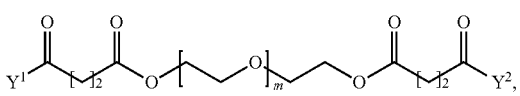

(V-3)
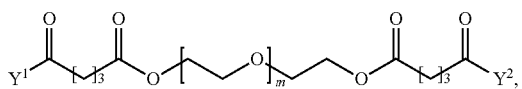

(V-4)
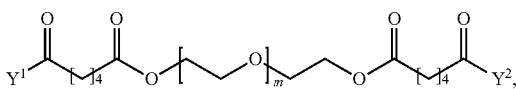

(V-5)
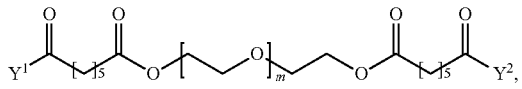

(V-6)
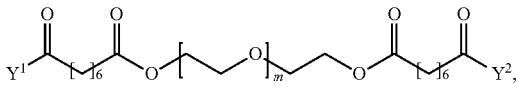

(V-7)
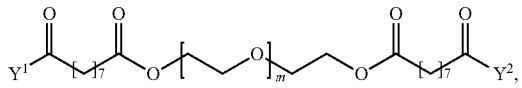

(V-8)
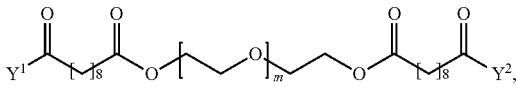

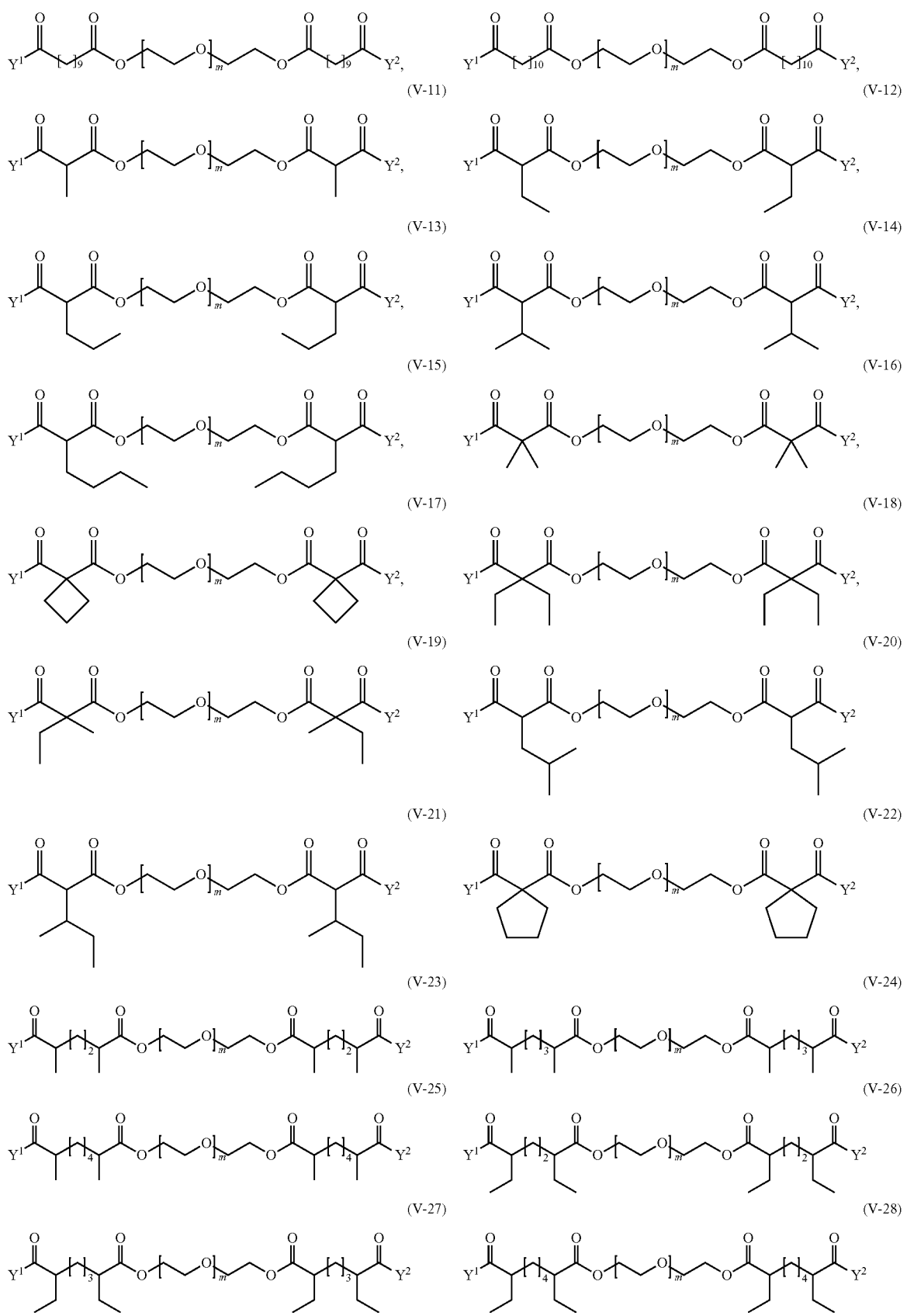

-continued
(V-29) 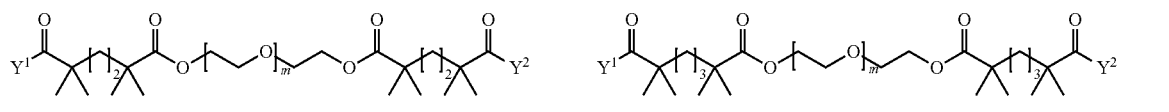
(V-30)
(V-31) 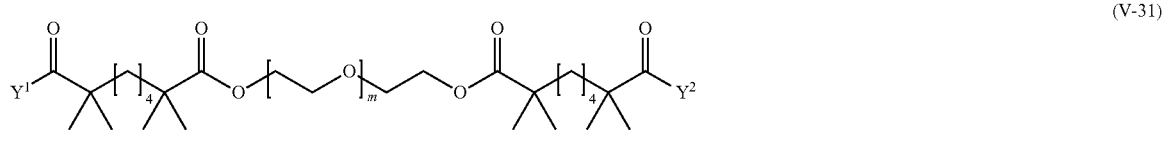
(V-32) 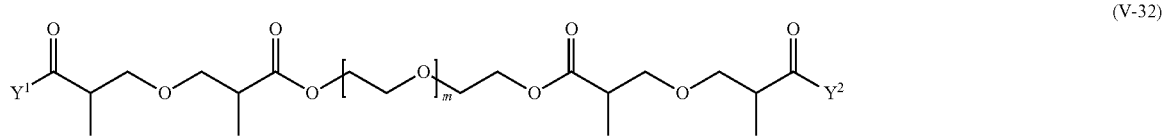
(V-33) 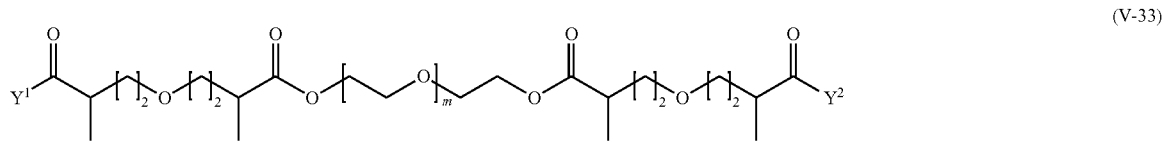
(V-34) 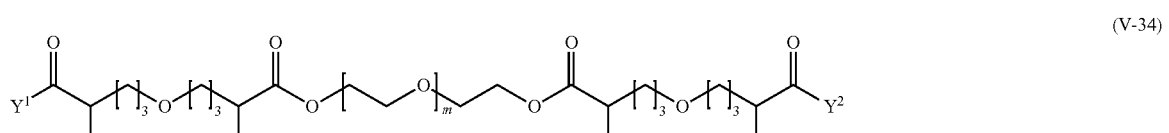
(V-35) 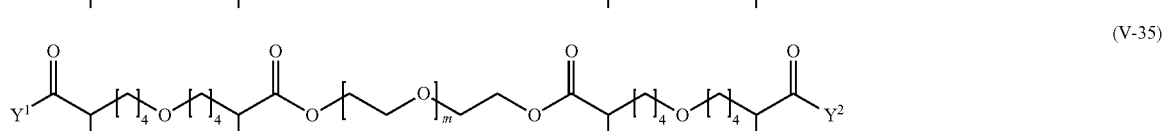
(V-36) (V-37) 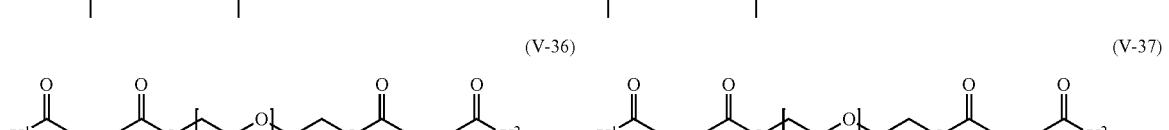
(V-38) (V-39) 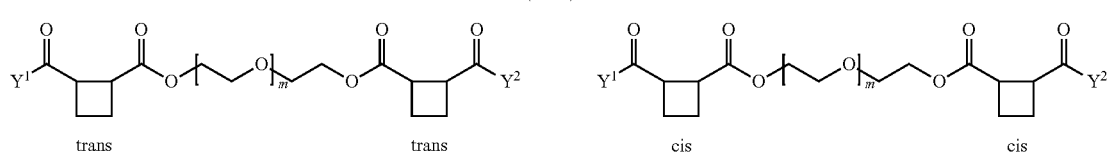
(V-40) (V-41) 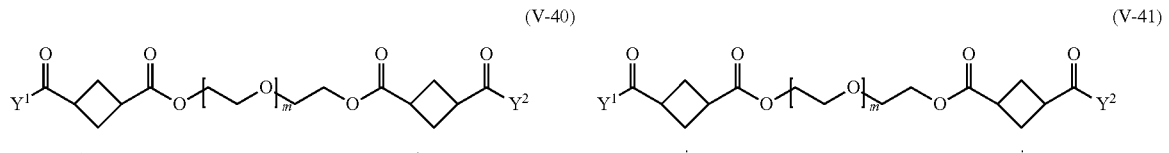
(V-42) (V-43) 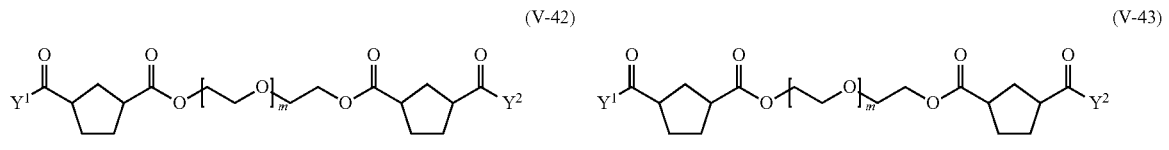

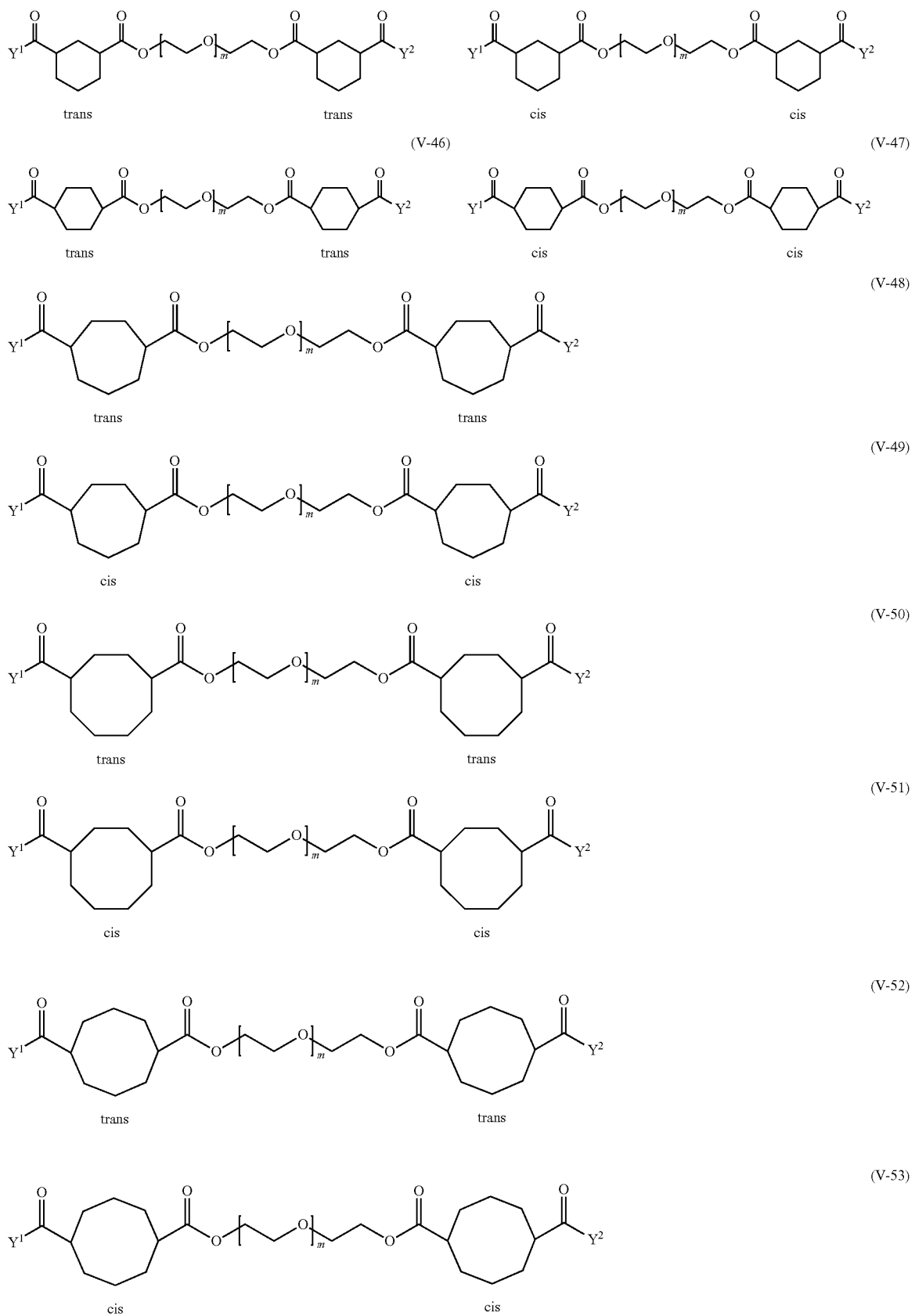

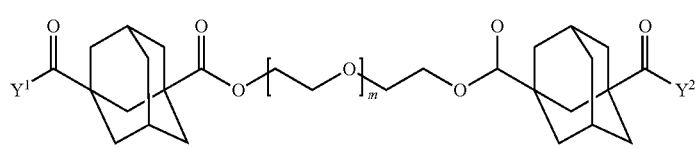
wherein
each crosslinker reagent may be in the form of its racemic mixture, where applicable; and
m, $Y^1$ and $Y^2$ are defined as above.
Even more preferred crosslinker reagents are of formula (Va-1) to (Va-54):
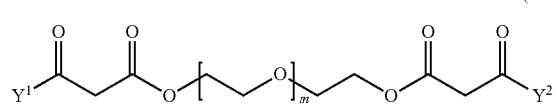
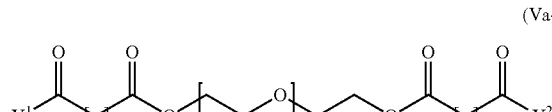
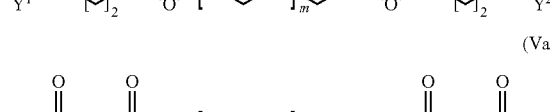
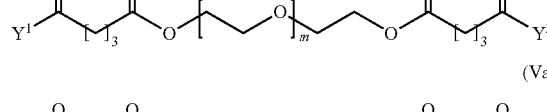
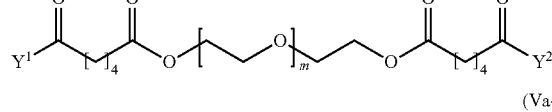
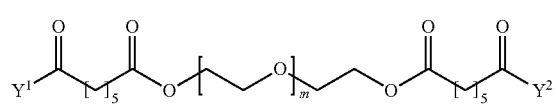
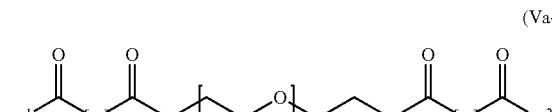
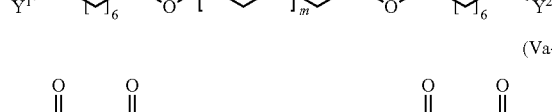
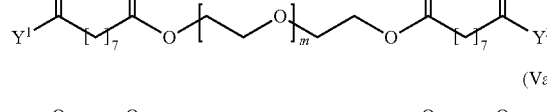
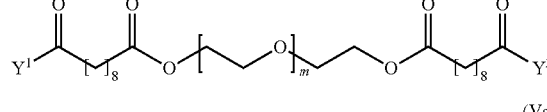
-continued
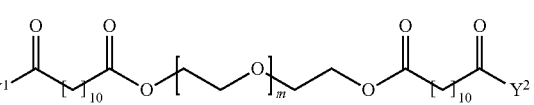
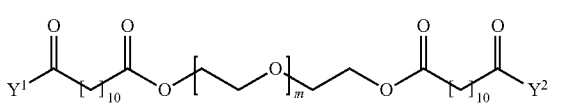
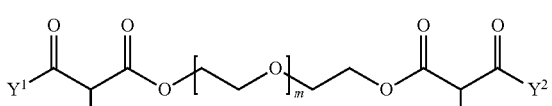
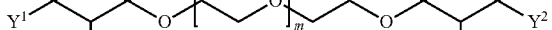
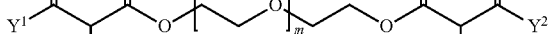

(Va-18)
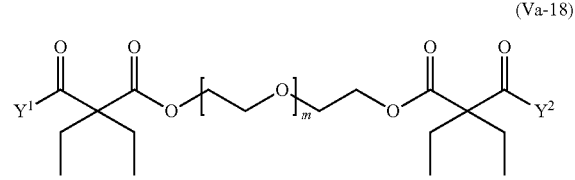
(Va-19)
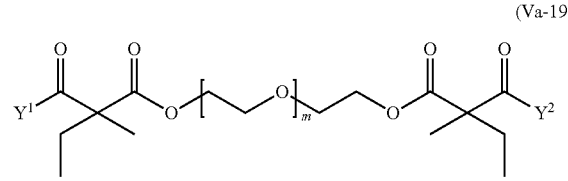
(Va-20)
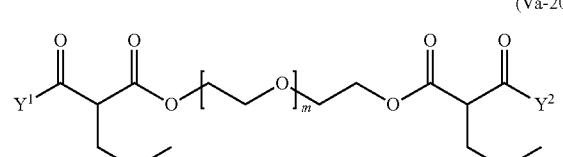
(Va-21)
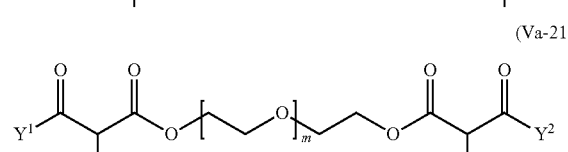
(Va-22)
(Va-23)
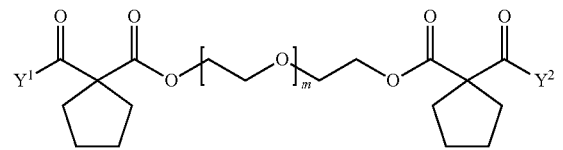
(Va-24)
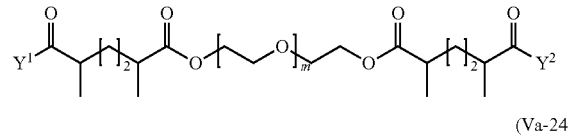
(Va-25)
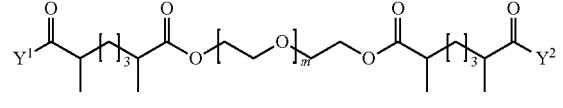
(Va-26)
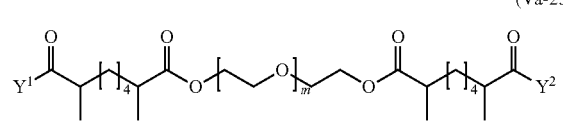
(Va-27)
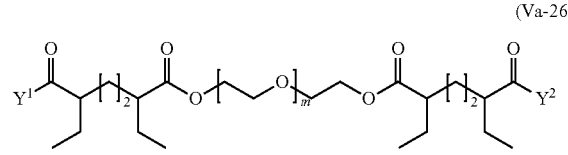
(Va-28)
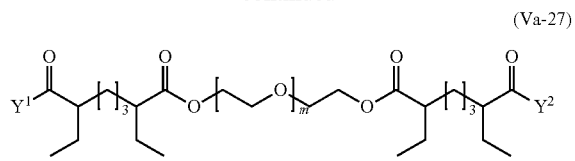
(Va-29)
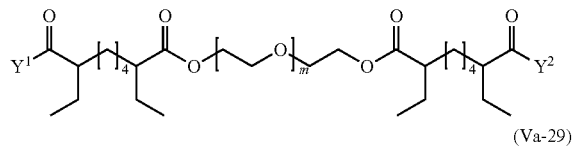
(Va-30)
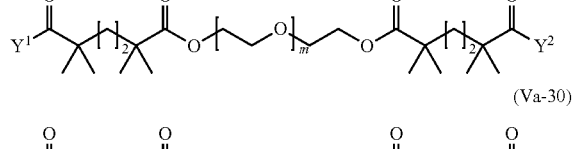
(Va-31)
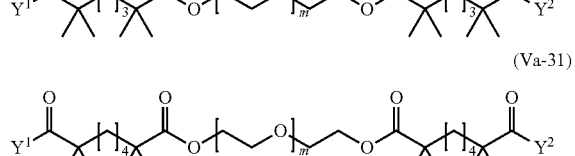
(Va-32)
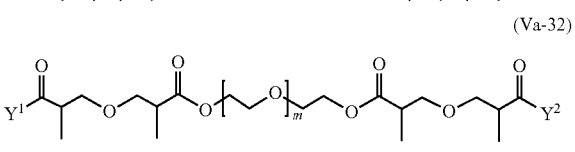
(Va-33)
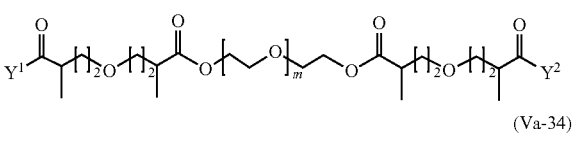
(Va-34)
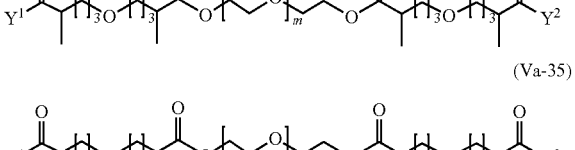
(Va-35)
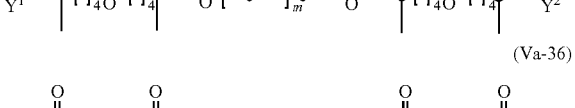
(Va-36)
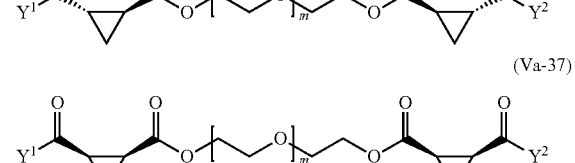
(Va-37)
(Va-38)
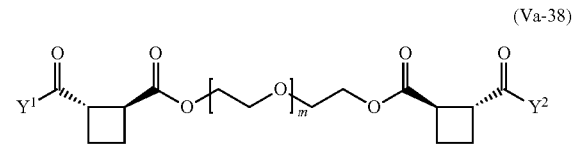

wherein
each crosslinker reagent may be in the form of its racemic mixture, where applicable; and
m, $Y^1$ and $Y^2$ are defined as above.

It was surprisingly found that the use of crosslinker reagents with branches, i.e. residues other than H, at the alpha carbon of the carbonyloxy group lead to the formation of hydrogels which are more resistant against enzymatic degradation, such as degradation through esterases.

Similarly, it was surprisingly found that the fewer atoms there are between the (C=O) of a carbonyloxy group and the (C=O) of the adjacent activated ester, activated carbamate, activated carbonate or activated thiocarbamate, the more resistant against degradation the resulting hydrogels are, such as more resistant against degradation through esterases.

Accordingly, crosslinker reagents V-11 to V-54, V-1, V-2, Va-11 to Va-54, Va-1 and Va-2 are preferred crosslinker reagents. Crosslinker reagents Va-11 to Va-54, Va-1 and Va-2 are most preferred crosslinker reagents. Most preferred is crosslinker reagent Va-14.

In another embodiment, crosslinker reagents V-1, V-2, V-5, V-6, V-7, V-8, V-9, V-10, V-11, V-12, V-13, V-14, V-15, V-16, V-17, V-18, V-19, V-20, V-21, V-22, V-23, V-24, V-25, V-26, V-27, V-28, V-29, V-30, V-31, V-32, V-33, V-34, V-35, V-36, V-37, V-38, V-39, V-40, V-41, V-42, V-43, V-44, V-45, V-46, V-47, V-48, V-49, V-50, V-51, V-52, V-53 an V-54 are preferred crosslinker reagents. More preferably, the at least one crosslinker reagent is of formula V-5, V-6, V-7, V-8, V-9, V-10, V-14, V-22, V-23, V-43, V-44, V-45 or V-46, and most preferably, the at least one crosslinker reagent is of formula V-5, V-6, V-9 or V-14.

In another embodiment, crosslinker reagents Va-1, Va-2, Va-5, Va-6, Va-7, Va-8, Va-9, Va-10, Va-11, Va-12, Va-13, Va-14, Va-15, Va-16, Va-17, Va-18, Va-19, Va-20, Va-21, Va-22, Va-23, Va-24, Va-25, Va-26, Va-27, Va-28, Va-29, Va-30, Va-31, Va-32, Va-33, Va-34, Va-35, Va-36, Va-37, Va-38, Va-39, Va-40, Va-41, Va-42, Va-43, Va-44, Va-45, Va-46, Va-47, Va-48, Va-49, Va-50, Va-51, Va-52, Va-53 an Va-54 are even more preferred crosslinker reagents. More preferably, the at least one crosslinker reagent is of formula Va-5, Va-6, Va-7, Va-8, Va-9, Va-10, Va-14, Va-22, Va-23, Va-43, Va-44, Va-45 or Va-46, and most preferably, the at least one crosslinker reagent is of formula Va-5, Va-6, Va-9 or Va-14.

The preferred embodiments of the compound of formula (V-I) and (V-II) as mentioned above apply accordingly to the preferred compounds of formulas (V-1) to (V-54) and to the more preferred compounds of formulas (Va-1) to (Va-54).

In another aspect, the present invention relates to a hydrogel obtainable by a process of the present invention as defined above.

The hydrogel contains from 0.01 to 1 mmol/g primary amine groups (—$NH_2$), more preferably, from 0.02 to 0.5 mmol/g primary amine groups and most preferably from 0.05 to 0.3 mmol/g primary amine groups. The term "X mmol/g primary amine groups" means that 1 g of dry hydrogel comprises X mmol primary amine groups. Measurement of the amine content of the hydrogel is carried out according to Gude et al. (Letters in Peptide Science, 2002, 9(4): 203-206, which is incorporated by reference in its entirety) and is also described in detail in the Examples section.

Preferably, the term "dry" as used herein means having a residual water content of a maximum of 10%, preferably less than 5% and more preferably less than 2% (determined according to Karl Fischer). The preferred method of drying is lyophilization.

Process for the Preparation of a Hydrogel-Spacer Conjugate

In another aspect, the present invention relates to a process for the preparation of a hydrogel-spacer conjugate comprising the step of:

(d) reacting the hydrogel from step (b) or (c) with a spacer reagent of formula (VI)

  (VI), $A^{x1}$-$S^0$-$A^{x2}$ wherein $S^0$ is selected from the group comprising $C_{1-50}$ alkyl, $C_{2-50}$ alkenyl and $C_{2-50}$ alkynyl, which fragment is optionally interrupted by one or more group(s) selected from —NH—, —N($C_{1-4}$ alkyl)-, —O—, —S, —C(O)—, —C(O)NH, —C(O)N($C_{1-4}$ alkyl)-, —O—C(O)—, —S(O)—, —S(O)$_2$—, 4- to 7-membered heterocyclyl, phenyl and naphthyl;

$A^{x1}$ is a functional group for reaction with an amine group of the hydrogel; and $A^{x2}$ is a functional group;

in the presence of a solvent to obtain a hydrogel-spacer conjugate.

Preferably, $A^{x1}$ is selected from the group comprising activated carboxylic acid; Cl—(C═O)—; NHS—(C═O)—, wherein NHS is N-hydroxysuccinimide; ClSO$_2$—; $R^1$(C═O)—; I—; Br—; Cl—; SCN—; and CN—, wherein $R^1$ is selected from the group comprising H, $C_{1-6}$ alkyl, alkenyl, $C_{2-6}$ alkynyl, $C_3$-8 cycloalkyl, 4- to 7-membered heterocyclyl, 8- to 11-membered heterobicyclyl, phenyl, naphthyl, indenyl, indanyl, and tetralinyl.

Most preferably, $A^{x1}$ is an activated carboxylic acid.

Suitable activating reagents to obtain the activated carboxylic acid are for example N,N'-dicyclohexyl-carbodiimide (DCC), 1-ethyl-3-carbodiimide (EDC), benzotriazol-1-yl-oxytripyrrolidinophosphonium hexafluorophosphate (PyBOP), bromotripyrrolidinophosphonium hexafluorophosphate (PyBrOP), 1-cyano-2-ethoxy-2-oxoethylidenaminooxy)dimethylamino-morpholino-carbenium hexafluorophosphate (COMU), 1-hydroxybenzotriazole (HOBT), 1-hydroxy-7-azabenzotriazole (HOAT), O-(6-chlorobenzotriazol-1-yl)-N,N,N',N'-tetramethyluronium hexafluorophosphate (HCTU), 1—H-benzotriazolium (HBTU), (O-(7-azabenzotriazol-1-yl)-N,N,N',N'-tetramethyluronium hexafluorophosphate (HATU), and O-(benzotriazol-1-yl)-N,N,N',N'-tetramethyluronium tetrafluoroborate (TBTU). These reagents are commercially available and well-known to the skilled person.

Preferably, $A^{x2}$ is selected from the group comprising -maleimide, —SH, —$NH_2$, —SeH, —$N_3$, —C≡CH, —$CR^1$═$CR^{1a}R^{1b}$, —OH, —(CH═$X^0$)—$R^1$, —(C═O)—S—$R^1$, —(C═O)—H, —NH—$NH_2$, —O—$NH_2$, —Ar—$X^0$, —Ar—Sn($R^1$)($R^{1a}$)($R^{1b}$), —Ar—B(OH)(OH),

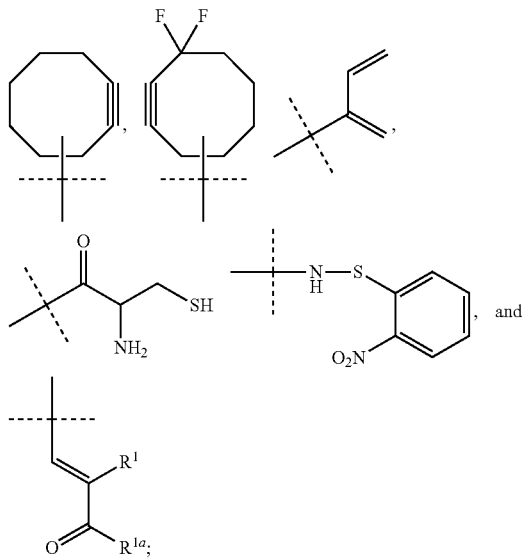

with optional protecting groups;

wherein $X^0$ is —OH, —$NR^1R^{1a}$, —SH, and —SeH,

Ar is selected from phenyl, naphthyl, indenyl, indanyl, and tetralinyl, and $R^1$, $R^{1a}$, $R^{1b}$ are independently of each other selected from the group comprising H, $C_{1-6}$ alkyl, $C_{2-6}$ alkenyl, $C_{2-6}$ alkynyl, $C_{3-8}$ cycloalkyl, 4- to 7-membered heterocyclyl, 8- to 11-membered heterobicyclyl, phenyl, naphthyl, indenyl, indanyl, and tetralinyl.

More preferably, $A^{x2}$ is selected from —$NH_2$, maleimide and thiol and most preferably $A^{x2}$ is maleimide. Equally preferred is thiol (—SH).

Suitable reaction conditions are described in the Examples sections and are known to the person skilled in the art.

Process step (d) may be carried out in the presence of a base. Suitable bases include customary inorganic or organic bases. These preferably include alkaline earth metal or alkali metal hydrides, hydroxides, amides, alkoxides, acetates, carbonates or bicarbonates such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN), N,N-diisopropylethylamine (DIPEA), diazabicycloundecene (DBU) or collidine.

Process step (d) may be carried out in the presence of a solvent. Suitable solvents for carrying out the process step (d) of the invention include organic solvents. These preferably include water and aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, carbon tetrachloride, dichloroethane or trichloroethane; alcohols such as methanol, ethanol, n- or i-propanol, n-, i-, sec- or tert-butanol, ethanediol, propane-1,2-diol, ethoxyethanol, methoxyethanol, diethylene glycol monomethyl ether, dimethylether, diethylene glycol; acetonitrile, N-methyl-2-pyrrolidone (NMP), dimethylformamide (DMF), dimethyl sulfoxide (DMSO), N,N-dimethylacetamide, nitromethane, nitrobenzene, hexamethylphosphoramide (HMPT), 1,3-dimethyl-2-imidazolidinone (DMI), 1,3-dimethyl-3,4,5,6-tetrahydro-2(1H)-pyrimidinone (DMPU), ethyl acetate, acetone, butanone; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; or mixtures thereof. Preferably, the solvent is selected from water, acetonitrile or N-methyl-2-pyrrolidone.

In another aspect, the present invention relates to a hydrogel-spacer conjugate obtainable by the above-described process.

Process for the Preparation of a Carrier-Linked Prodrug

In another aspect, the present invention relates to a process for the preparation of a carrier-linked prodrug comprising the step of:

(e) reacting the hydrogel of step (b) or (c) or the hydrogel-spacer conjugate of step (d) with a prodrug linker-biologically active moiety reagent of formula (VII)

$A^{y1}$-L-D    (VII), wherein
$A^{y1}$ is a functional group for reaction with an amine of the hydrogel of step (b) or (c) or for reaction with the functional group $A^{x2}$ of the hydrogel-spacer conjugate of step (d),
L is a prodrug linker;
D is a biologically active moiety;
in the presence of a solvent, to obtain a carrier linked prodrug.

Process step (e) may be carried out in the presence of a solvent. Suitable solvents for carrying out the process step (e) of the invention include organic solvents. These preferably include water and aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, carbon tetrachloride, dichloroethane or trichloroethane; alcohols such as methanol, ethanol, n- or i-propanol, n-, i-, sec- or tert-butanol, ethanediol, propane-1,2-diol, ethoxyethanol, methoxyethanol, diethylene glycol monomethyl ether, dimethylether, diethylene glycol; acetonitrile, N-methyl-2-pyrrolidone (NMP), dimethylformamide (DMF), dimethyl sulfoxide (DMSO), N,N-dimethylacetamide, nitromethane, nitrobenzene, hexamethylphosphoramide (HMPT), 1,3-dimethyl-2-imidazolidinone (DMI), 1,3-dimethyl-3,4,5,6-tetrahydro-2(1H)-pyrimidinone (DMPU), ethyl acetate, acetone, butanone; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; or mixtures thereof. Preferably, the solvent is selected from water, acetonitrile or N-methyl-2-pyrrolidone.

If the prodrug linker-biologically active moiety reagent of formula (VII) reacts with an amine of the hydrogel of step (b) or (c), then $A^{y1}$ is maleimide or OH—, preferably maleimide.

If the prodrug linker-biologically active moiety reagent of formula (VII) reacts with $A^{x2}$ of the hydrogel-spacer conjugate of step (d), the structure of $A^{y1}$ depends on the structure of $A^{x2}$ with which $A^{y1}$ reacts. Preferred pairs of $A^{x2}/A^{y1}$ are selected from the following:

| $A^{x2}$ | $A^{y1}$ |
|---|---|
| -maleimide | HS—, H$_2$N—, or HSe— |
| —SH, —NH$_2$, or —SeH | maleimide- |
| —N$_3$ | HC≡C—, 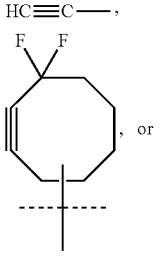, or 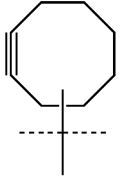 |
| —C≡CH, 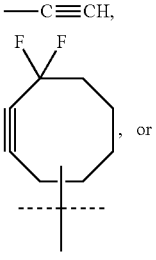, or 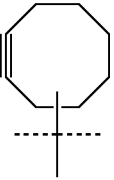 | N$_3$— |

-continued

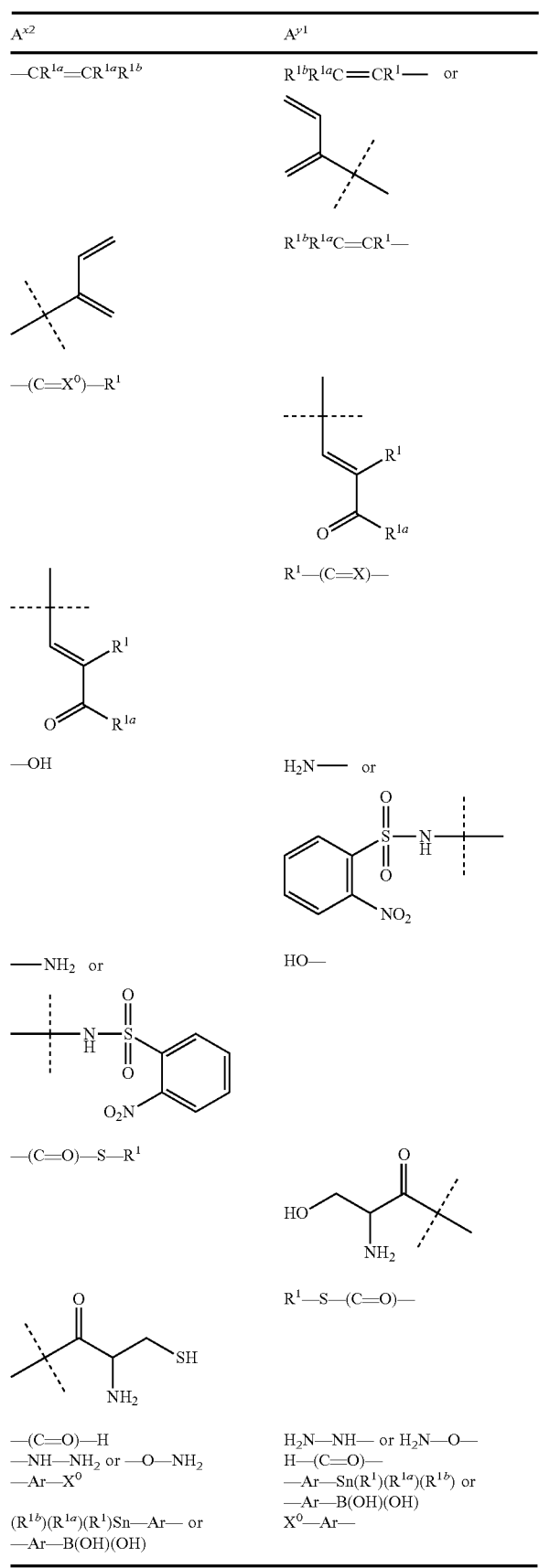

wherein $X^0$ is —OH, —NR$^1$R$^{1a}$, —SH, and —SeH;

R$^1$, R$^{1a}$, R$^{1b}$ are independently of each other selected from the group comprising H, C$_{1-6}$ alkyl, C$_{2-6}$ alkenyl, C$_{2-6}$ alkynyl, C$_{3-8}$ cycloalkyl, 4- to 7-membered heterocyclyl, 8- to 11-membered heterobicyclyl, phenyl, naphthyl, indenyl, indanyl, and tetralinyl; and Ar is selected from phenyl, naphthyl, indenyl, indanyl, and tetralinyl.

More preferably, A$^{y1}$ is selected from —SH or -maleimide and most preferably A$^{y1}$ is —SH and, accordingly, a preferred A$^{x2}$ is -maleimide or —SH and a most preferred A$^{x2}$ is -maleimide.

In a particularly preferred embodiment A$^{x2}$ is a thiol and A$^{y1}$ of formula (VII) is of formula (VIIa)

$$T\text{-}PG^0\text{-}S— \tag{VIIa}$$

wherein

T is H or a tag moiety;

PG$^0$ is a sulfur-activating moiety; and

S is sulfur.

In one embodiment PG$^0$ of formula (VIIa) is selected from the group consisting of

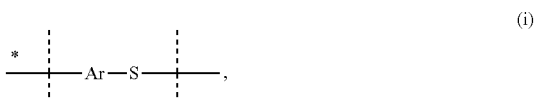 (i)

 (ii)

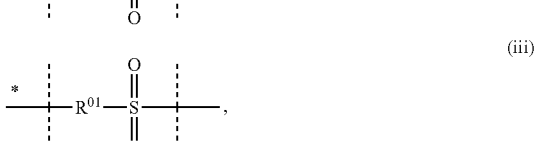 (iii)

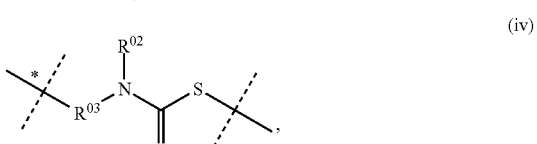 (iv)

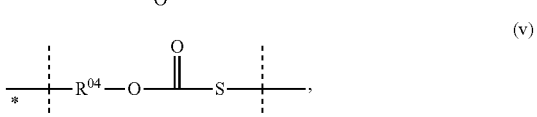 (v)

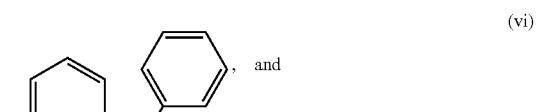 (vi)

, and

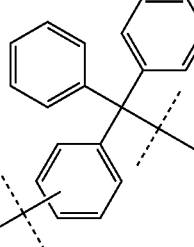

(vii)

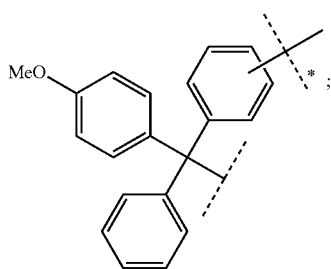

wherein the dashed lines marked with an asterisk indicate attachment to T of formula (VIIa) and the unmarked lines indicate attachment to the sulfur of formula (VIIa);

Ar is an aromatic moiety which is optionally further substituted;

$R^{01}$, $R^{03}$, $R^{04}$ are independently of each other a chemical bond or is $C_{1-50}$ alkyl; $C_{2-50}$ alkenyl; or $C_{2-50}$ alkynyl, wherein $C_{1-50}$ alkyl; $C_{2-50}$ alkenyl; and $C_{2-50}$ alkynyl are optionally substituted with one or more $R^3$, which are the same or different and wherein $C_{1-50}$ alkyl; $C_{2-50}$ alkenyl; and $C_{2-50}$ alkynyl are optionally interrupted by one or more groups selected from the group consisting of -Q-, —C(O)O—; —O—; —C(O)—; —C(O)N($R^4$)—; —S(O)$_2$N($R^4$)—; —S(O)N($R^4$)—; —S(O)$_2$—; —S(O)—; —N($R^4$)S(O)$_2$N($R^{4a}$)—; —S—; —N($R^4$)—; —OC(O)$R^4$; —N($R^4$)C(O)—; —N($R^4$)S(O)$_2$—; —N($R^4$)S(O)—; —N($R^4$)C(O)O—; —N($R^4$)C(O)N($R^{4a}$)—; and —OC(O)N($R^4R^{4a}$);

$R^{02}$ is —H; $C_{1-50}$ alkyl; $C_{2-50}$ alkenyl; or $C_{2-50}$ alkynyl, wherein $C_{1-50}$ alkyl; $C_{2-50}$ alkenyl; and $C_{2-50}$ alkynyl are optionally substituted with one or more $R^3$, which are the same or different and wherein $C_{1-50}$ alkyl; $C_{2-50}$ alkenyl; and $C_{2-50}$ alkynyl are optionally interrupted by one or more groups selected from the group consisting of -Q-, —C(O)O—; —O—; —C(O)—; —C(O)N($R^4$)—; —S(O)$_2$N($R^4$)—; —S(O)N($R^4$)—; —S(O)$_2$—; —S(O)—; —N($R^4$)S(O)$_2$N($R^{4a}$)—; —S—; —N($R^4$)—; —OC(O)$R^4$; —N($R^4$)C(O)—; —N($R^4$)S(O)$_2$—; —N($R^4$)S(O)—; —N($R^4$)C(O)O—; —N($R^4$)C(O)N($R^{4a}$)—; and —OC(O)N($R^4R^{4a}$);

Q is selected from the group consisting of phenyl; naphthyl; indenyl; indanyl; tetralinyl; $C_{3-10}$ cycloalkyl; 4- to 7-membered heterocyclyl; and 8- to 11-membered heterobicyclyl, wherein T is optionally substituted with one or more $R^3$, which are the same or different;

$R^3$ is halogen; —CN; oxo (=O); —COO$R^5$; —O$R^5$; —C(O)$R^5$; —C(O)N($R^5R^{5a}$); —S(O)$_2$N($R^5R^{5a}$); —S(O)N($R^5R^{5a}$); —S(O)$_2R^5$; —S(O)$R^5$; —N($R^5$)S(O)$_2$N($R^{5a}R^{5b}$); —S$R^5$; —N($R^5R^{5a}$); —NO$_2$; —OC(O)$R^5$; —N($R^5$)C(O)$R^{5a}$; —N($R^5$)S(O)$_2R^{5a}$; —N($R^5$)S(O)$R^{5a}$; —N(R)C(O)O$R^{5a}$; —N($R^5$)C(O)N($R^{5a}R^{5b}$); —OC(O)N($R^{5a}R^{5a}$); or $C_{1-6}$ alkyl, wherein $C_{1-6}$ alkyl is optionally substituted with one or more halogen, which are the same or different; and $R^4$, $R^{4a}$, $R^5$, $R^{5a}$, $R^{5b}$ are independently selected from the group consisting of —H; or $C_{1-6}$ alkyl, wherein $C_{1-6}$ alkyl is optionally substituted with one or more halogen, which are the same or different.

Preferably, $R^{01}$ is $C_{1-6}$ alkyl. Even more preferably, $R^1$ is selected from —CH$_2$—, —CH$_2$—CH$_2$— and —CH$_2$—CH$_2$—CH$_2$—.

Preferably, $R^{02}$ is selected from H and $C_{1-6}$ alkyl.

Preferably, $R^{03}$ is $C_{1-6}$ alkyl.

Preferably, $R^{04}$ is $C_{1-6}$ alkyl.

Preferably, Ar is selected from the group consisting of

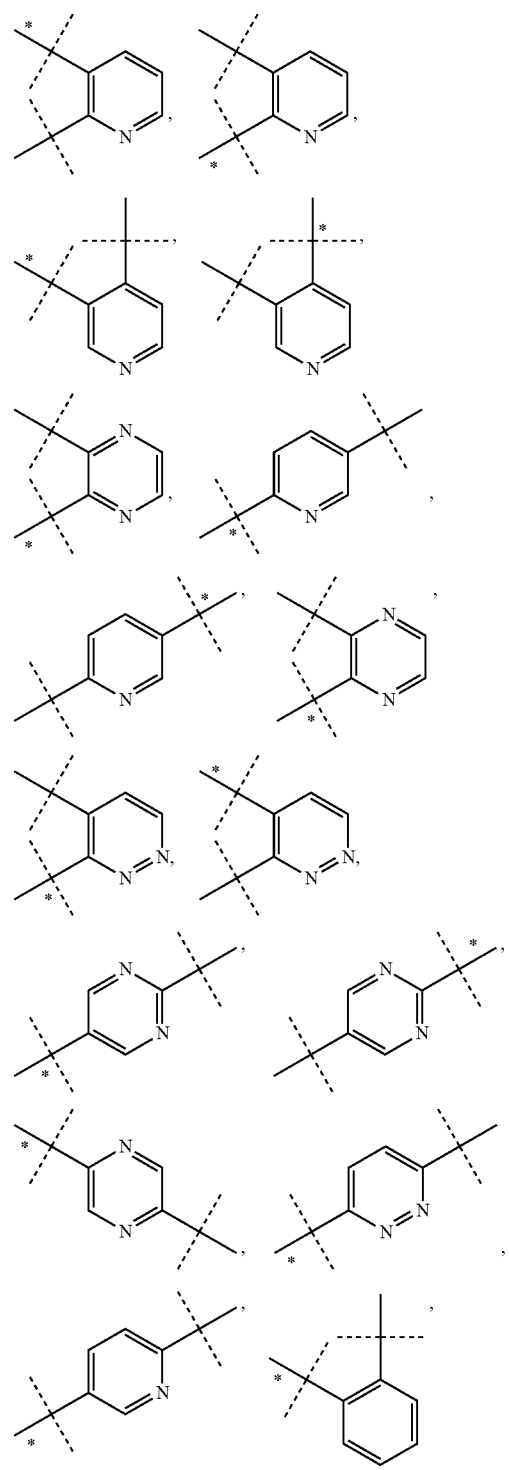

-continued

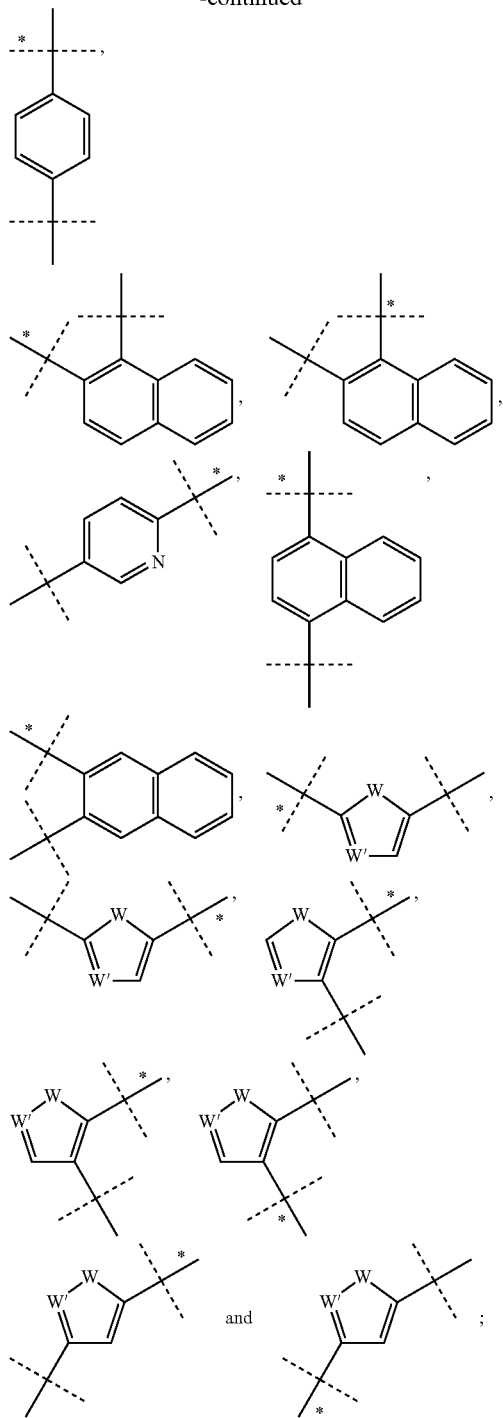

wherein
dashed lines marked with an asterisk indicate attachment to T of formula (VIIa) and the unmarked dashed lines indicate attachment to the rest of PG⁰ of formula (VIIa);
W is independently of each other O, S, or N;
W' is N; and
wherein Ar is optionally substituted with one or more substituent(s) independently selected from the group consisting of $NO_2$, Cl and F.
More preferably, $PG^0$ of formula (VIIa) is selected from the group consisting of

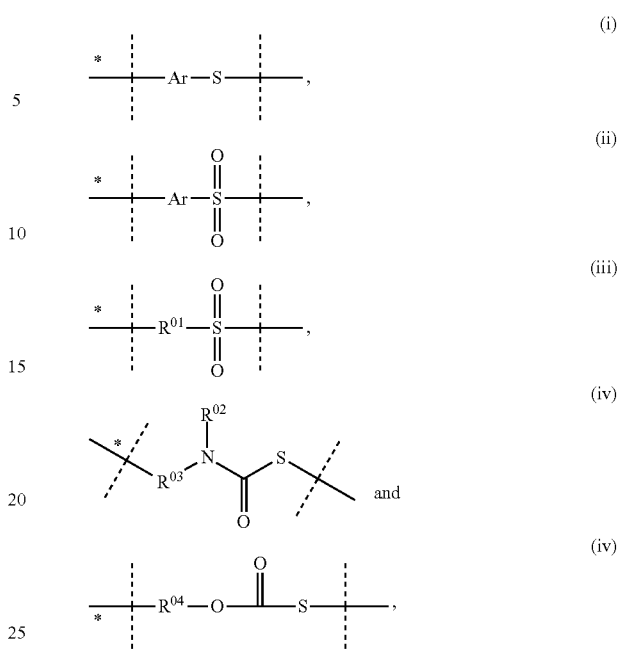

wherein
the dashed lines marked with an asterisk indicate attachment to T of formula (VIIa) and the unmarked lines indicate attachment to the sulfur of formula (VIIa); and Ar, $R^{01}$, $R^{02}$, $R^{03}$ and $R^{04}$ are used as above.

More preferably, $PG^0$ of formula (VIIa) is

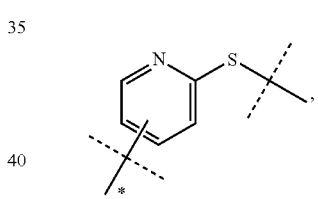

wherein
the dashed line marked with an asterisk indicates attachment to T of formula (VIIa) and the unmarked dashed line indicates attachment to the sulfur of formula (VIIa).

Most preferably, $PG^0$ of formula (VIIa) is

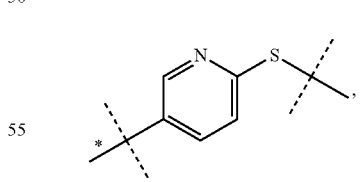

wherein
the dashed line marked with an asterisk indicates attachment to T of formula (VIIa) and the unmarked dashed line indicates attachment to the sulfur of formula (VIIa).

In one preferred embodiment T of formula (VIIa) is H.
In another embodiment, T of formula (VIIa) comprises a polymeric moiety. Preferably, T of formula (VIIa) comprises a polymer selected from the group consisting of 2-methacryloyl-oxyethyl phosphoylcholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(alkylene glycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(imino carbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

If T of formula (VIIa) is a polymeric moiety it is preferred that T has a molecular weight of at least 1 kDa, preferably of at least 3 kDa and most preferably of at least 5 kDa. If T of formula (VIIa) is a polymeric moiety it is preferred that it has a molecular weight of at most 1000 kDa, e.g. at most 800 kDa, at most 500 kDa, at most 250 kDa, at most 200 kDa, or at most 100 kDa.

In another embodiment, T of formula (VIIa) comprises an affinity ligand. Preferably, T of formula (VIIa) comprises, more preferably T is an affinity ligand moiety selected from the group consisting of 4-aminobenzamidine, 3-(2'-aminobenzhydryloxy)tropane, ϵ-aminocaproyl-p-chlorobenzylamide, 1-amino-4-[3-(4,6-dichlorotriazin-2-ylamino)-4-sulfophenylamino]anthraquinone-2-sulfonic acid, 2-(2'-amino-4'-methylphenylthio)-N,N-dimethylbenzylamine dihydrochloride, angiopoietin-1, aptamers, arotinoid acid, avidin, biotin, calmodulin, cocaethylene, cytosporone B, N,N-dihexyl-2-(4-fluorophenyl)indole-3-acetamide, N,N-dipropyl-2-(4-chlorophenyl)-6,8-dichloro-imidazo[1,2-a]pyridine-3-acetamide, 5-fluoro-2'-deoxyuridine 5'-(p-aminophenyl) monophosphate, S-hexyl-L-glutathione, (S,S)-4-phenyl-α-(4-phenyloxazolidin-2-ylidene)-2-oxazoline-2-acetonitrile, Pro-Leu-Gly hydroxamate, 2-(4-(2-(trifluoromethyl)phenyl)piperidine-1-carboxamido)benzoic acid, trimethyl(m-aminophenyl)ammonium chloride, urocortin III, cofactors like adenosin triphosphate, s-adenosyl methionine, ascorbic acid, cobalamine, coenzyme A, coenzyme B, coenzyme M, coenzyme Q, coenzyme F420, cytidine triphosphate, flavin mononucleotide, flavin adenine dinucleotide, glutathion, heme, lipoamide, menaquinone, methanofuran, methylcobalamine, molybdopterin, NAD+, NADP+, nucleotide sugars, 3'-phosphoadenosine-5'-phosphosulfate, pyridoxal phosphate, polyhistidines, pyrroloquinoline quinone, riboflavin, streptavidin, tetrahydrobiopterin, tetrahydromethanopterin, tetrahydrofolic acid, biotin carboxyl carrier protein (BCCP), chitin binding protein, FK506 binding proteins, FLAG tag, green fluorescent protein, glutathion-S-transferase, hemagglutinin, maltose binding protein, myc tag, NusA, protein C epitope, S-tag, strep-tag, thioredoxins, triazines and antibody fragments.

If T of formula (VIIa) comprises an affinity ligand, it is preferred that the affinity ligand is a polyhistidine.

In another embodiment, T of formula (VIIa) comprises a charged moiety. Preferably, T of formula (VIIa) comprises at least one positive and/or negative charge. It is understood that the number of positive and negative charges of T is unequal to ensure that T is a charged molecule.

Preferably, T of formula (VIIa) comprises at least one positive or negative charge, e.g. at least two positive or negative charges, at least three positive or negative charges, at least four positive or negative charges, at least five positive or negative charges, at least six positive or negative charges, at least seven positive or negative charges, at least eight positive or negative charges, at least nine positive or negative charges, at least ten positive or negative charges, at least eleven positive or negative charges, at least twelve positive or negative charges, at least thirteen positive or negative charges, at least fourteen positive or negative charges or at least fifteen positive or negative charges.

More preferably, T of formula (VIIa) comprises at least one positive charge, such as one positive charge, two positive charges, three positive charges, four positive charges, five positive charges, six positive charges, seven positive charges, eight positive charges, nine positive charges, ten positive charges, eleven positive charges, twelve positive charges, thirteen positive charges, fourteen positive charges or fifteen positive charges. More preferably, T of formula (VIIa) comprises one positive charge, two positive charges, three positive charges, four positive charges, five positive charges, six positive charges, seven positive charges or eight positive charges. More preferably, T of formula (VIIa) comprises two positive charges, three positive charges, four positive charges, five positive charges or six positive charges.

Preferably, the at least one positive charge of T of formula (VIIa) is provided by an ammonium or phosphonium.

Preferably, T of formula (VIIa) comprises a polyamide containing at least one quaternary ammonium residue and/or at least one protonated ammonium residue, optionally comprising further functional groups. Preferably, such optional further functional groups are amine functional groups. Preferably, T of formula (VIIa) comprises at least one quaternary ammonium residue and/or at least one protonated ammonium residue. Even more preferably, T of formula (VIIa) comprises four quaternary ammonium residues and/or four protonated ammonium residues.

Preferably, T of formula (VIIa) comprises in bound form a polyamine. More preferably, T of formula (VIIa) comprises in bound form a polyamine selected from the group consisting of ethylene diamine, 1,3-diaminopropane, hexamethylene diamine, cadaverin, putrescin, spermine, spermidine, norspermidine and tetraethylmethylenediamine.

Even more preferably, T of formula (VIIa) comprises a moiety of formula (a):

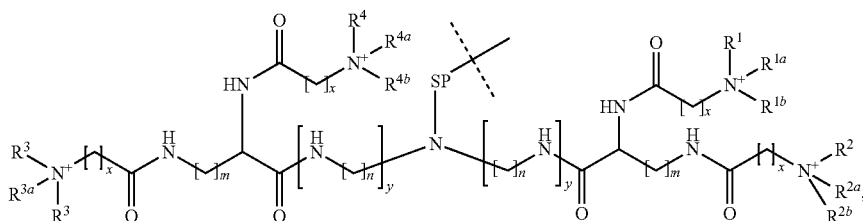

(a)

wherein
the dashed line indicates attachment to $PG^0$;
$R^1$, $R^{1a}$, $R^{1b}$, $R^2$, $R^{2a}$, $R^{2b}$, $R^3$, $R^{3a}$, $R^{3b}$, $R^4$, $R^{4a}$, $R^{4b}$ are independently of each other H or methyl;
each m is independently of each other 1, 2, 3, 4, 5, 6, 7, or 8;
each n is independently of each other 1, 2, 3, 4, 5, 6, 7, or 8;
each x is independently of each other 1, 2, 3, 4, 5, 6, 7 or 8:
each y is independently of each other 0, 1, 2, 3, 4, 5, 6, 7 or 8; and
SP is a spacer moiety.

Preferably, the moiety of formula (a) is symmetric, i.e. the moiety

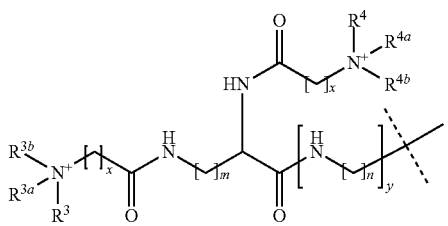

is the same as the moiety

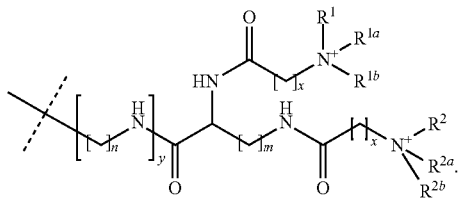

In one embodiment $R^1$, $R^{1a}$, $R^{1b}$ of formula (a) are all methyl.
In another embodiment $R^1$ of formula (a) is H and $R^{1a}$ and $R^{1b}$ of formula (a) are both methyl.
In one embodiment $R^2$, $R^{2a}$, $R^{2b}$ of formula (a) are all methyl.
In another embodiment $R^2$ of formula (a) is H and $R^{2a}$ and $R^{2b}$ of formula (a) are both methyl.
In one embodiment $R^3$, $R^{3a}$, $R^{3b}$ of formula (a) are all methyl.
In another embodiment $R^3$ of formula (a) is H and $R^{3b}$ of formula (a) are both methyl.
In one embodiment $R^4$, $R^{4a}$, $R^{4b}$ of formula (a) are all methyl.
In another embodiment $R^4$ of formula (a) is H and $R^{4a}$ and $R^{4b}$ of formula (a) are both methyl.

Preferably, m of formula (a) is 1, 2, 3, 4, 5 or 6. More preferably, m of formula (a) is 2, 3, 4, or 5, even more preferably, m of formula (a) is 3, 4 or 5 and most preferably, m of formula (a) is 4.
Preferably, n of formula (a) is 1, 2, 3, 4, 5 or 6. More preferably, n of formula (a) is 2, 3, 4, or 5, even more preferably, n of formula (a) is 2, 3 or 4 and most preferably, n of formula (a) is 3.
Preferably, x of formula (a) is 1, 2, 3, 4, 5 or 6. More preferably, n of formula (a) is 1, 2, 3, or 4, even more preferably, x of formula (a) is 1, 2, or 3 and most preferably, x of formula (a) is 1.
Preferably, y of formula (a) is 1, 2, 3, 4, 5 or 6. More preferably, y of formula (a) is 1, 2, 3, or 4, even more preferably, y of formula (a) is 1, 2, or 3 and most preferably, y of formula (a) is 1.
In one preferred embodiment, $R^1$, $R^{1a}$, $R^{1b}$, $R^2$, $R^{2a}$, $R^{2b}$, $R^3$, $R^{3a}$, $R^{3b}$, $R^4$, $R^{4a}$, $R^{4b}$ are methyl; m is 4; n is 3; y is 1 and x is 1.
In another preferred embodiment, $R^1$, $R^2$, $R^3$, $R^4$ are H; $R^{1a}$, $R^{1b}$, $R^{2a}$, $R^{2b}$, $R^{3a}$, $R^{3b}$, $R^{4a}$, $R^{4b}$ are methyl, m is 4; n is 3; y is 1 and x is 1.
Preferred counter ions for T of formula (I) are Cl⁻, TFA⁻ and $SO_4^-$.
If $A^{y1}$ is of formula (VIIa) and T is a tag moiety, then T can be used to purify prodrug linker-biologically active moiety reagent of formula (VII) which have a defined number of moieties $A^{y1}$-L per moiety D from a mixture of prodrug linker-biologically active moiety reagents of formula (VII) in which each D is connected to x moieties $A^{y1}$-L and wherein x is a positive integer, such as 1, 2, 3, 4, 5, 6, 7, 8, 9, or 10. T can thus be used to isolate monoconjugates of the prodrug linker-biologically active moiety reagent of formula (VII).
The method of isolating a monoconjugates of the prodrug linker-biologically active depends on the tag moiety T of formula (VIIa).
If T of formula (VIIa) is a polymeric moiety with a molecular weight of at least 10% (w/w) of D of formula (VII), the isolation step is preferably size-exclusion chromatography.
If T of formula (VIIa) comprises an affinity ligand, the isolation step is preferably affinity chromatography.
If T of formula (VIIa) comprises a charged moiety, the isolation step is preferably ion exchange chromatography.
In a preferred embodiment T of formula (VIIa) is a charged moiety and the isolation step is preferably ion exchange chromatography.
Preferably, process step (e) comprises the step of reacting a hydrogel-spacer conjugate of step (d) with a prodrug-biologically active moiety reagent of formula (VII).
Suitable reaction conditions are described in the Examples sections and are known to the person skilled in the art.

Consequently, the process for the preparation of a carrier-linked prodrug preferably comprises the steps of:
(d) reacting the hydrogel from step (b) or (c) with a spacer reagent of formula (VI)

$$A^{x1}\text{-}S^0\text{-}A^{x2} \quad (VI),$$

wherein
$S^0$ is selected from the group comprising $C_{1-50}$ alkyl, $C_{2-50}$ alkenyl and $C_{2-50}$ alkynyl, which fragment is optionally interrupted by one or more group(s) selected from —NH—, —N($C_{1-4}$ alkyl)-, —O—, —S—, —C(O)—, —C(O)NH, —C(O)N($C_{1-4}$ alkyl)-, —O—C(O)—, —S(O)—, —S(O)$_2$—, 4- to 7-membered heterocyclyl, phenyl and naphthyl;
$A^{x1}$ is a functional group for reaction with an amine group of the hydrogel; and
$A^{x2}$ is a functional group;
in the presence of a solvent to obtain a hydrogel-spacer conjugate; and
(e) reacting the hydrogel-spacer conjugate of step (d) with a prodrug linker-biologically active moiety reagent of formula (VII)

$$A^1\text{-}L\text{-}D \quad (VII),$$

wherein
$A^{y1}$ is a functional group for reaction with the functional group $A^{x2}$ of the hydrogel-spacer conjugate of step (d),
L is a prodrug linker;
D is a biologically active moiety;
in the presence of a solvent, to obtain a carrier linked prodrug.

Preferred combinations of $A^{x2}$ and $A^{y1}$ are as disclosed above.

The prodrug linker reagent or the prodrug linker moiety as part of the prodrug linker-biologically active moiety reagent may have the structure of any prodrug linker moiety known in the art.

Preferably, the prodrug linker reagent or the prodrug linker moiety as part of the prodrug linker-biologically active moiety reagent is a traceless prodrug linker reagent or moiety.

A preferred prodrug linker is disclosed and can be obtained as described in WO 2005/099768 A2. Accordingly, a preferred prodrug linker-biologically active moiety reagent $A^{y1}$-L-D has the structure of formula (h-i) or (h-ii):

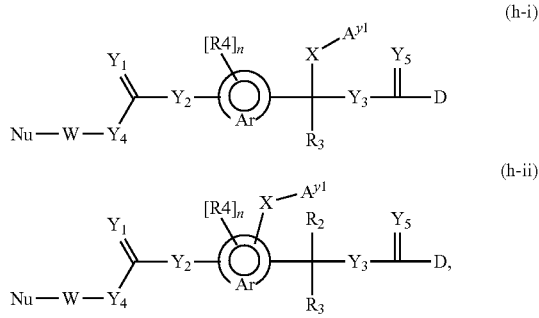

wherein
$A^{y1}$ is a functional group as defined in step (e),
D is a biologically active moiety which is connected to L via an amine-group of the corresponding drug;

X is a spacer moiety such as $R_5$—$Y_6$,
$Y_1$, $Y_2$ are independently O, S or $NR_6$,
$Y_3$, $Y_5$ are independently O or S,
$Y_4$ is O, $NR_6$ or $C(R_7)(R_8)$—,
$Y_6$ is O, S, $NR_6$, succinimide, maleimide, unsaturated carbon-carbon bonds or any heteroatom containing a free electron pair or is absent,
$R_2$, $R_3$ are independently of each other selected from hydrogel, substituted or non-substituted linear, branched or cyclical alkyl or heteroalkyl, aryls, substituted aryls, substituted or non-substituted heteroaryl, cyano, nitro, halogen, carboxy, carboxylalkyl, alkylcarbonyl or carboxamidoalkyl;
$R^4$ is selected from hydrogen, substituted or non-substituted linear, branched or cyclical alkyl or heteroalkyl, aryl, substituted aryl, substituted or non-substituted heteroaryl, substituted or non-substituted linear, branched or cyclical alkoxy, substituted or non-substituted linear, branched or cyclical heteroalkyloxy, aryloxy or heteroaryloxy, cyano, halogen,
$R_5$ is selected from substituted or non-substituted linear, branched or cyclical alkyl or heteroalkyl, aryls, substituted aryls, substituted or non-substituted heteroaryls,
$R_6$ is selected from hydrogel, substituted or non-substituted linear, branched or cyclical alkyl or heteroalkyl, aryls, substituted or non-substituted heteroaryls,
$R_7$, $R_8$ are independently selected from hydrogen, substituted or non-substituted linear, branched or cyclical alkyl or heteroalkyl, aryls, substituted aryls, substituted or non-substituted heteroaryls, carboxyalkyl, alkylcarbonyl, carboxamidoalkyl, cyano or halogen,
W is selected from substituted or non-substituted linear, branched or cyclical alkyl, aryls, substituted aryls, substituted or non-substituted linear, branched or cyclical heteroalkyl, substituted or non-substituted heteroaryls,
Nu is a nucleophile,
n is zero or a positive integer, and
Ar is a multi-substituted aromatic hydrocarbon or a multi-substituted aromatic heterocycle.

It is understood that in formulas (h-i) and (h-ii) L corresponds to the moiety linking $A^{y1}$ and D.

Preferably, $R_2$, $R_3$, R4, $R_5$, $R_6$, $R_7$ and $R_8$ of formula (h-i) and (h-ii) are independently selected from H, $C_{1-6}$ alkyl, $C_{2-6}$ alkenyl and $C_{2-6}$ alkynyl.

Preferably, $Y_6$ of formula (h-i) and (h-ii) is $C_{1-20}$ alkyl, $C_{2-20}$ alkenyl or $C_{2-20}$ alkynyl.

Preferably, Nu of formula (h-i) and (h-ii) is selected from the group of nucleophiles consisting of primary, secondary and tertiary amino groups, thiol, carboxylic acid, hydroxylamine, hydrazine and nitrogen containing heteroaryl.

Preferably, W of formula (h-i) and (h-ii) is —$(CR_9R_{10})_b$—, wherein $R_9$ and $R_{10}$ are independently selected from H, $C_{1-6}$ alkyl, $C_{2-6}$ alkenyl and $C_{2-6}$ alkynyl and wherein b is 1, 2, 3, 4 or 5.

Preferably, n of formula (h-i) and (h-ii) is 0, 1 or 2, more preferably, n is 0 or 1 and most preferably n is 0.

Preferably, Ar of formula (h-i) and (h-ii) is selected from

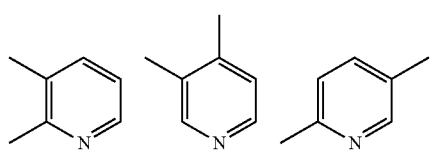

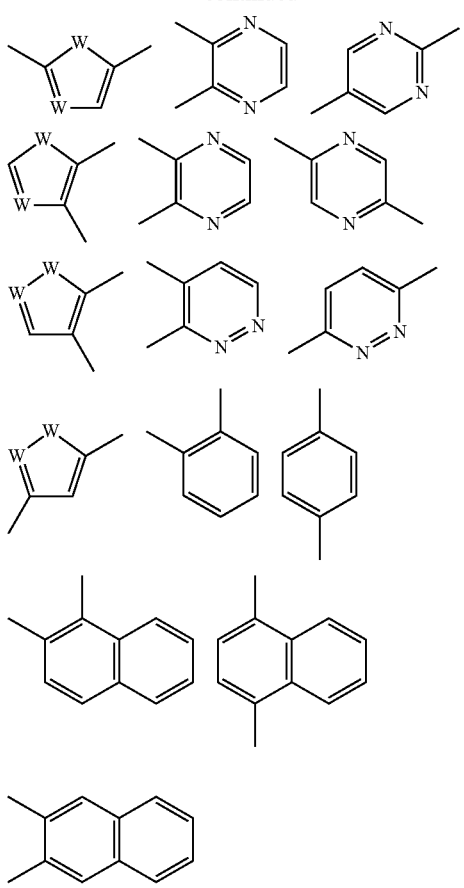

Other preferred prodrug linkers are disclosed and can be obtained as described in WO 2006/136586 A2. Accordingly, a preferred prodrug linker-biologically active moiety reagent $A^y$-L-D has the structure of formula (h-iii), (h-iv) or (h-v):

(iii)

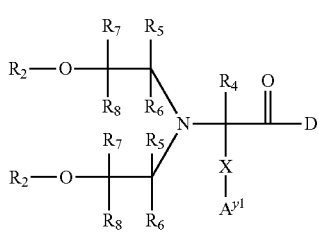

(h-iv)

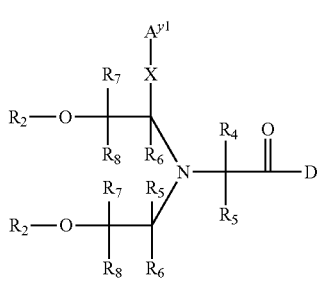

(h-v)

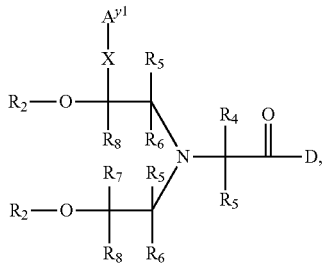

wherein
- $A^{y1}$ is a functional group as defined in step (e);
- D is a biologically active moiety which is connected to to L via an amine-group of the corresponding drug forming an amide linkage;
- X is a spacer moiety such as R13-Y1;
- Y1 is O, S, NR6, succinimide, maleimide, unsaturated carbon-carbon bonds or any heteroatom-containing a free electron pair or is absent;
- $R^{13}$ is selected from substituted or non-substituted linear, branched or cyclical alkyl or heteroalkyl, aryls, substituted aryls, substituted or non-substituted heteroaryls;
- $R_2$ and $R_3$ are selected independently from hydrogen, acyl groups, or protecting groups for hydroxyl groups;
- $R_4$ to $R_{12}$ are selected independently from hydrogen, substituted or non-substituted linear, branched or cyclical alkyl or heteroalkyl, aryls, substituted aryls, substituted or non-substituted heteroaryls, cyano, nitro, halogen, carboxy, carboxamide.

It is understood that in formulas (h-iii), (h-iv) and (h-v) L corresponds to the moiety linking $A^{y1}$ and D.

Preferably, $R_2$, $R_3$, $R_4$, $R_5$, $R_6$, $R_7$, $R_8$, $R_9$, $R_{10}$, $R_{11}$ and $R_{12}$ of formula (h-iii), (h-iv) and (h-v) are independently selected from H, $C_{1-6}$ alkyl, $C_{2-6}$ alkenyl and $C_{2-6}$ alkynyl.

Preferably, in the formulas (h-iii), (h-iv) and (h-v) Y1 is $C_{1-20}$ alkyl, $C_{2-20}$ alkenyl or $C_{2-20}$ alkynyl.

Another preferred prodrug linker is disclosed and can be obtained as described in WO 2009/095479 A2. Accordingly, a preferred prodrug linker-biologically active moiety reagent $A^{y1}$-L-D has the structure of formula (h-vi):

(h-vi)

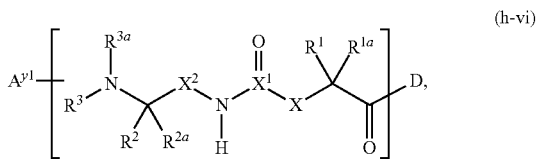

wherein
- $A^{y1}$ is a functional group as defined in step (e);
- D is a biologically active moiety which is connected to the rest of the molecule via an aromatic amine of the corresponding drug by forming an amide linkage;
- $X^1$ is $C(R^4R^{4a})$; $N(R^4)$; O; $C(R^4R^{4a})$—$C(R^5R^{5a})$; $C(R^5R^{5a})$—$C(R^4R^{4a})$; $C(R^4R^{4a})$—$N(R^6)$; $N(R^6)$—$C(R^4R^{4a})$; $C(R^4R^{4a})$—O; or O—$C(R^4R^{4a})$;
- $X^1$ is C; or S(O);
- $X^2$ is $C(R^7, R^{7a})$; or $C(R^7, R^{7a})$—$C(R^8, R^{8a})$;
- $R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, $R^{8a}$ are independently selected from the group consisting of H; and $C_{1-4}$ alkyl;

optionally, one or more of the pair(s) $R^{1a}/R^{4a}$, $R^{1a}/R^{5a}$, $R^{4a}/R^{5a}$, $R^{4a}/R^{5a}$, $R^{7a}/R^{8a}$ form a chemical bond;

optionally, one or more of the pair(s) $R^1/R^{1a}$, $R^2/R^{2a}$, $R^4/R^{4a}$, $R^5/R^{5a}$, $R^7/R^{7a}$, $R^8/R^{8a}$ are joined together with the atom to which they are attached to form a $C_{3-8}$ cycloalkyl; or 4- to 7-membered heterocyclyl;

optionally, one or more of the pair(s) $R^1/R^4$, $R^1/R^5$, $R^1/R^6$, $R^4/R^5$, $R^7/R^8$, $R^2/R^3$ are joined together with the atoms to which they are attached to form a ring A;

optionally, $R^3/R^{3a}$ are joined together with the nitrogen atom to which they are attached to form a 4- to 7-membered heterocycle;

A is selected from the group consisting of phenyl; naphthyl; indenyl; indanyl; tetralinyl; $C_{3-10}$ cycloalkyl; 4- to 7-membered heterocyclyl; and 8- to 11-membered heterobicyclyl;

provided that one hydrogen of $R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$ or $R^{8a}$ is replaced by $A^{y1}$.

It is understood that in formula (h-vi) L corresponds to the moiety linking $A^{y1}$ and D.

Another preferred prodrug linker is disclosed and can be obtained as described in WO 2011/012721 A1 and WO 2011/012722 A1. Accordingly, a preferred prodrug linker-biologically active moiety reagent $A^{y1}$-L-D has the structure of formula (h-vii):

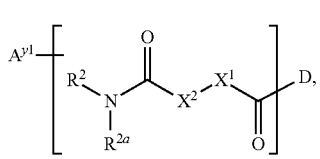

(h-vii)

wherein

D is a biologically active moiety which is connected to the rest of the molecule via an aromatic amine of the corresponding drug by forming an amide linkage;

$A^{y1}$ is a functional group as defined in step (e);

$X^1$ is $C(R^1R^{1a})$ or a cyclic fragment selected from $C_{3-8}$ cycloalkyl, 4- to 7-membered heterocyclyl, phenyl, naphthyl, indenyl, indanyl, tetralinyl, or 8- to 11-membered heterobicyclyl, wherein in case $X^1$ is a cyclic fragment, said cyclic fragment is incorporated into $L^1$ via two adjacent ring atoms and the ring atom of $X^1$, which is adjacent to the carbon atom of the amide bond, is also a carbon atom;

$X^2$ is a chemical bond or selected from $C(R^3R^{3a})$, $N(R^3)$, O, $C(R^3R^{3a})$—$C(R^4R^{4a})$, $C(R^3R^{3a})$—$N(R^4)$, $N(R^3)$—$C(R^4R^{4a})$, $C(R^3R^{3a})$—O, or O—$C(R^3R^{3a})$, wherein in case $X^1$ is a cyclic fragment, $X^2$ is a chemical bond, $C(R^3R^{3a})$, $N(R^3)$ or O;

optionally, in case $X^1$ is a cyclic fragment and $X^2$ is $C(R^3R^{3a})$, the order of the $X^1$ fragment and the $X^2$ fragment within $L^1$ may be changed and the cyclic fragment is incorporated into $L^1$ via two adjacent ring atoms;

$R^1$, $R^3$ and $R^4$ are independently selected from the group consisting of H, $C_{1-4}$ alkyl and —$N(R^5R^{5a})$;

$R^{1a}$, $R^2$, $R^{3a}$, $R^{4a}$ and $R^{5a}$ are independently selected from the group consisting of H, and $C_{1-4}$ alkyl;

$R^5$ is $C(O)R^6$;

$R^6$ is $C_{1-4}$ alkyl;

optionally, one of the pairs $R^{1a}/R^{4a}$, $R^{3a}/R^{4a}$ or $R^{1a}/R^{3a}$ form a chemical bond; provided that one hydrogen of $R^1$, $R^{1a}$, $R^2$, $R^{2a}$, $R^3$, $R^{3a}$, $R^4$, $R^{4a}$, $R^5$, $R^{5a}$ or $R^6$ is replaced by $A^{y1}$.

It is understood that in formula (h-vii) L corresponds to the moiety linking $A^{y1}$ and D.

Another preferred prodrug linker is disclosed and can be obtained as described in WO 2011/089214 A1. Accordingly, a preferred prodrug linker-biologically active moiety reagent $A^{y1}$-L-D has the structure of formula (h-viii):

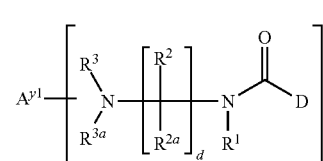

(h-viii)

wherein $A^{y1}$ is a functional group as defined in step (e);

D is a biologically active moiety which is connected to the rest of the molecule via an aromatic hydroxyl (—OH) of the corresponding drug by forming a carbamate linkage;

$R^1$ is selected from the group consisting of $C_{1-4}$ alkyl; heteroalkyl; $C_{3-8}$ cycloalkyl; and

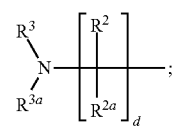

$R^2$, $R^{2a}$, $R^3$ and $R^{3a}$ are independently selected from hydrogen, substituted or non-substituted linear, branched or cyclic $C_{1-4}$ alkyl or heteroalkyl;

each d is independently 2, 3 or 4;

provided that one hydrogen of $R^1$, $R^2$, $R^{2a}$, $R^3$, or $R^{3a}$ is replaced by $A^y$.

It is understood that in formula (h-viii) L corresponds to the moiety linking $A^{y1}$ and D.

Another preferred prodrug linker is disclosed and can be obtained as described in WO 2011/089216 A1. Accordingly, a preferred prodrug linker-biologically active moiety reagent $A^{y1}$-L-D has the structure of formula (h-ix):

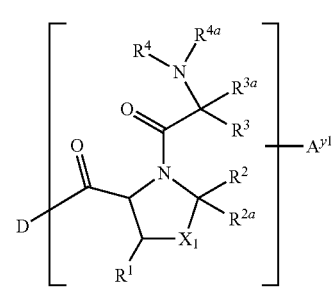

(h-ix)

wherein $A^{y1}$ is a functional group as defined in step (e);

D is a biologically active moiety which is connected to the rest of the molecule via an aliphatic amine of the corresponding drug by forming an amide linkage;

$X_1$ is selected from O, S or CH—$R^{1a}$;
$R^1$ and $R^{1a}$ are independently selected from H, OH, $CH_3$;
$R^2$, $R^{2a}$, $R^4$ and $R^{4a}$ are independently selected from H and $C_{1-4}$ alkyl,
$R^3$ and $R^{3a}$ are independently selected from H, $C_{1-4}$ alkyl, and $R^5$;
$R^5$ is selected from

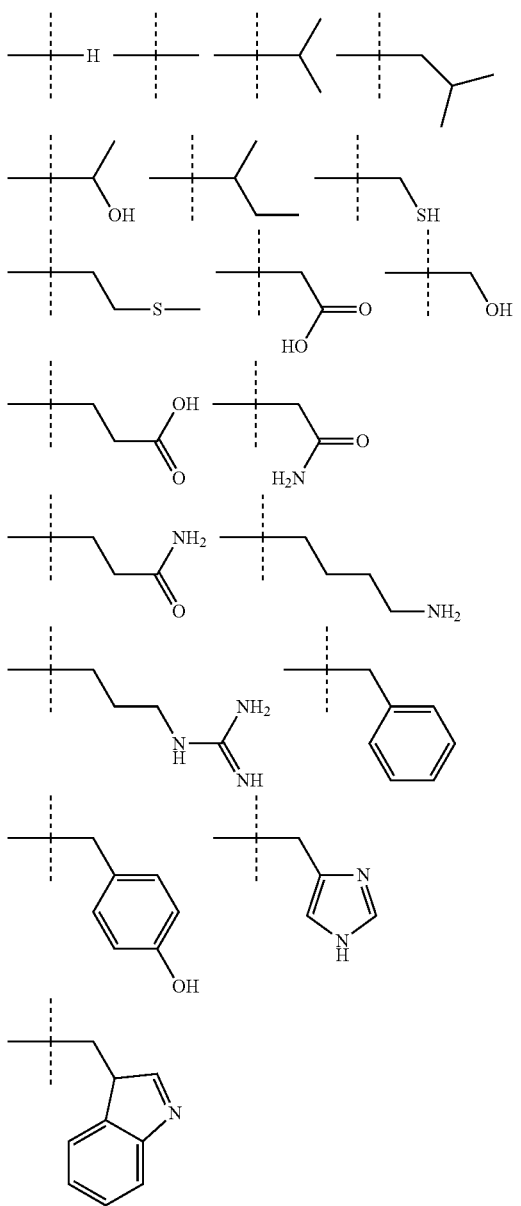

wherein
dashed lines indicate attachment to the rest of the moiety.
provided that one hydrogen of $R^1$, $R^{1a}$, $R^2$, $R^{2a}$, $R^3$, $R^{3a}$, $R^4$, $R^{4a}$ and $R^5$ is replaced by $A^{y1}$.

It is understood that in formula (h-ix) L corresponds to the moiety linking $A^{y1}$ and D.

Preferably, $R^3$ of formula (h-ix) is H and $R^{3a}$ of formula (h-ix) is $R^5$.

Preferably, one of $R^4/R^{4a}$ of formula (h-ix) is H.

Optionally, one or more of the pair(s) $R^3/R^{3a}$, $R^4/R^{4a}$, $R^3/R^4$ of formula (h-ix) may independently form one or more cyclic fragment(s) selected from $C_{3-8}$ cycloalkyl, 4- to 7-membered heterocyclyl, or 8- to 11-membered heterobicyclyl.

Optionally, $R^3$, $R^{3a}$, $R^4$ and $R^{4a}$ of formula (h-ix) are further substituted with $C_{1-6}$ alkyl, $C_{2-6}$ alkenyl, $C_{2-6}$ alkynyl, phenyl, 4- to 7-membered heterocycle or halogen.

Another preferred prodrug linker is disclosed and can be obtained as described in WO 2011/089215 A1. Accordingly, a preferred prodrug linker-biologically active moiety reagent $A^{y1}$-L-D has the structure of formula (h-x):

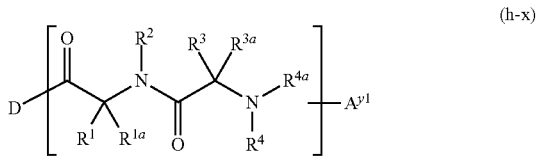

(h-x)

wherein
$A^{y1}$ is a functional group as defined in step (e);
D is a biologically active moiety which is connected to the rest of the molecule via an aromatic amine of the corresponding drug by forming an amide linkage;
$R^1$, $R^{1a}$, $R^2$, $R^3$, $R^{3a}$, $R^4$ and $R^{4a}$ are independently selected from H and $C_{1-4}$ alkyl;
optionally, any two of $R^1$, $R^{1a}$, $R^2$, $R^3$, $R^{3a}$, $R^4$ and $R^{4a}$ may independently form one or more cyclic fragment(s) selected from $C_{3-8}$ cycloalkyl, 4- to 7-membered heterocyclyl, phenyl, naphthyl, indenyl, indanyl, tetralinyl, or 8- to 11-membered heterobicyclyl;
optionally, $R^1$, $R^{1a}$, $R^2$, $R^3$, $R^{3a}$, $R^4$ and $R^{4a}$ are further substitute with a substituent selected from the group comprising $C_{1-6}$ alkyl, $C_{2-6}$ alkenyl, $C_{2-6}$ alkynyl, $C_{3-8}$ cycloalkyl, 4- to 7-membered heterocyclyl, phenyl, naphthyl, indenyl, indanyl, tetralinyl, or 8- to 11-membered heterobicyclyl;
provided that one hydrogen of $R^1$, $R^{1a}$, $R^2$, $R^3$, $R^{3a}$, $R^4$ and $R^{4a}$ is replaced by $A^{y1}$.

It is understood that in formula (h-x) L corresponds to the moiety linking $A^{y1}$ and D.

Another preferred prodrug linker is disclosed and can be obtained as described in PCT/EP2012/065748. Accordingly, a preferred prodrug linker-biologically active moiety reagent $A^{y1}$-L-D has the structure of formula (h-xi):

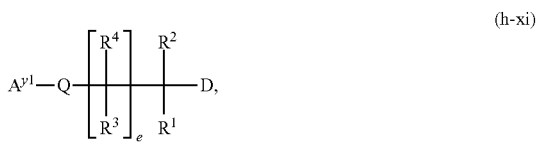

(h-xi)

wherein
$A^{y1}$ is a functional group as defined in step (e);
D is a biologically active moiety which is connected to the rest of the molecule via a carboxylic acid group (—(C═O)—OH) of the corresponding drug by forming a carboxylic ester linkage;
$R^1$ is selected from the group of unsubstituted alkyl; substituted alkyl; unsubstituted phenyl; substituted phenyl; unsubstituted naphthyl; substituted naphthyl; unsubstituted indenyl; substituted indenyl; unsubstituted indanyl; substituted indanyl; unsubstituted tetralinyl; substituted tetralinyl; unsubstituted $C_3$-10 cycloalkyl; substituted $C_3$-10 cycloalkyl; unsubstituted 4- to 7-membered heterocyclyl; substituted 4- to 7-membered heterocyclyl; unsubstituted 8- to 11-membered heterobicyclyl; and substituted 8- to 11-membered heterobicyclyl;

$R^2$ is selected from H, unsubstituted alkyl, and substituted alkyl $R^3$ and $R^4$ are independently selected from the group consisting of H, unsubstituted alkyl, and substituted alkyl;

e is 0 or 1;

optionally, $R^1$ and $R^3$ are joined together with the atoms to which they are attached to form a ring A;

A is selected from the group consisting of $C_{3-10}$ cycloalkyl; 4- to 7-membered aliphatic heterocyclyl; and 8- to 11-membered aliphatic heterobicyclyl, wherein A is unsubstituted or substituted;

Q is selected from the group comprising $C_{1-50}$ alkyl, $C_{2-50}$ alkenyl or $C_2$-50 alkinyl, which fragment is optionally interrupted by one or more group(s) selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4- to 7-membered heterocyclyl, phenyl or naphthyl.

It is understood that in formula (h-xi) L corresponds to the moiety linking $A^{y1}$ and D.

Another preferred prodrug linker is disclosed and can be obtained as described in EP12165516. Accordingly, a preferred prodrug linker-biologically active moiety reagent $A^{y1}$-L-D has the structure of formula (h-xii):

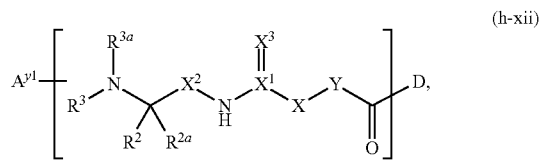

wherein $A^{y1}$ is a functional group as defined in step (e);

D is a biologically active moiety which is connected to the rest of the molecule via a hydroxyl group of the corresponding drug by forming an ester or carbamate linkage Y is —C($R^1$)($R^{1a}$)—; or —N(R')—;

X is —C($R^4$)($R^{4a}$)—; —N($R^4$)—; —O—; —C($R^4$)($R^{4a}$)—C($R^5$)($R^{5a}$)—; —C($R^4$)($R^{4a}$)—N($R^6$)—; —N($R^6$)—C($R^4$)($R^{4a}$)—; —C($R^4$)($R^{4a}$)—O—; —O—C($R^4$)($R^{4a}$)—; —C(O)—N($R^6$)—; or —N($R^6$)—C(O)—;

$X^1$ is

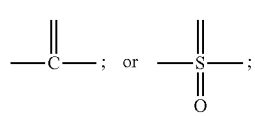

$X^2$ is —C($R^7$)($R^{7a}$)—; or —C($R^7$)($R^{7a}$)—C($R^8$)($R^{8a}$)—;
$X^3$ is =O; =S; or =N—CN;
$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, $R^{8a}$ are independently selected from the group consisting of H; $C_{1-6}$ alkyl, $C_{2-6}$ alkenyl, $C_{2-6}$ alkynyl; $C_{1-20}$ heteroalkyl and $Y_1$-T; and independently none, one or more of the pair(s) $R^{1a}/R^{4a}$, $R^{1a}/R^{5a}$, $R^{4a}/R^{5a}$, $R^{7a}/R^{8a}$ are absent and the corresponding carbon atoms to which they are attached form a cis double bond;

$Y^1$ is a chemical bond or $C_{1-6}$ alkyl, $C_{2-6}$ alkenyl, $C_{2-6}$ alkynyl;

T is selected from the group consisting of phenyl; naphthyl; indenyl; indanyl; tetralinyl; $C_{3-10}$ cycloalkyl; 4- to 7-membered heterocyclyl; or 8- to 11-membered heterobicyclyl, wherein T is optionally substituted with one or more $R^9$, which are the same or different;

$R^9$ is halogen; —CN; oxo (=O); —C(O)OH; —OH; —S(O)$_2$NH$_2$; —S(O)NH$_2$; —S(O)$_2$OH; —S(O)OH; —SH; —NH$_2$; —NO$_2$; $C_{1-6}$ alkyl, or $C_{1-10}$ heteroalkyl;

optionally, one or more of the pairs $R^1/R^{1a}$, $R^1/R^4$, $R^1/R^6$, $R^1/R^5$, $R^2/R^{2a}$, $R^2/R^3$, $R^4/R^{4a}$, $R^4/R^5$, $R^5/R^{5a}$, $R^7/R^{7a}$, $R^7/R^8$, $R^8/R^{8a}$ are joined together with the atom to which they are attached to form a ring T;

optionally, $R^3/R^{3a}$ are joined together with the nitrogen atom to which they are attached to form a 4- to 7-membered heterocycle;

provided that one hydrogen of $R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$ or $R^{8a}$ is replaced by $A^{y1}$.

It is understood that in formula (h-xii) L corresponds to the moiety linking $A^{y1}$ and D.

In a preferred embodiment, the prodrug linker-biologically active moiety reagent $A^{y1}$-L-D is of formula (h-i) or (h-ii).

In another preferred embodiment, the prodrug linker-biologically active moiety reagent $A^{y1}$-L-D is of formula (h-vi).

Any drug that comprises at least one functional group can be conjugated to a prodrug linker reagent to obtain a prodrug linker-biologically active moiety reagent $A^{y1}$-L-D. Such drug is selected from the group comprising polypeptides, proteins, and oligonucleotides. Preferably, the drug is a protein.

Preferably, D has a molecular weight ranging between 2 and 500 kDa, more preferably between 5 and 250 kDa, more preferably between 5 and 100 kDa and most preferably between 10 and 60 kDa.

In one embodiment the drug is a protein drug. Preferably, the drug is a protein drug that modulates the activity of one or more of the biological target(s) selected from basic fibroblast growth factors (bFGF), acidic fibroblast growth factors (aFGF), transforming growth factors alpha (TGFa), transforming growth factors beta (TGFβ), platelet-derived growth factor (PDGF), angiogenin, platelet-derived endothelial cell growth factor (PD-ECGF), interleukin-1 (IL-1) interleukin-8 (IL-8), interleukin-12, vascular endothelial growth factor (VEGF), angiopoietin-I, Del-I, follistatin, granulocyte colony-stimulating factor (G-CSF), hepatocyte growth factor (HGF), leptin, midkine, placental growth factor, pleiotrophin (PTN), progranulin, proliferin, tumor necrosis factor-alpha (TNF-alpha), angioarrestin, angiostatin (plasminogen fragment), antiangiogenic antithrombin III, cartilage-derived inhibitor (CDI), CDS9 complement fragment, endostatin (collagen XVIII fragment), fibronectin fragment, gro-beta, heparinases, heparin hexasaccharide fragment, human chorionic gonadotropin (hCG), interferon alpha/beta/gamma, interferon inducible protein (IP-IO), kringle S (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), retinoids, tetrahydrocortisol-S, thrombospondin-I (TSP-I), vasculostatin, and vasostatin (calreticulin fragment), prostaglandin, growth hormone, insulin-like growth factor-I (IGF-I), sphingosine-1-phosphate, factor D, RTP801, inhibitors of complement, including C1, C3 and C5, $\alpha_2$ adrenergic agonist, mTOR, ciliary neurotrophic factor (CNTF), brain-derived neurotrophic factor (BDNF), glial cell-derived neurotrophic factor (GDNF), lens epithelium derived growth factor (LEDGF), rod-derived cone viability factor (RdCVF), pigment epithelium-derived factor (PEDF).

If the drug is a protein it is preferably selected from the group consisting of ACTH, adenosine deaminase, agalsidase, albumin, alfa-1 antitrypsin (AAT), alfa-1 proteinase inhibitor (API), alglucosidase, alteplase, anistreplase, ancrod serine protease, antibodies (monoclonal or polyclonal and fragments or fusions), antithrombin III, antitrypsins, aprotinin, asparaginases, biphalin, bone-morphogenic proteins, calcitonin (salmon), collagenase, DNase, endorphins, enfuvirtide, enkephalins, erythropoietins, factor VIIa, factor VIII, factor VIIIa, factor IX, fibrinolysin, fusion proteins, follicle-stimulating hormones, granulocyte colony stimulating factor (G-CSF), galactosidase, glucagon, glucagon-like peptides like GLP-1, glucocerebrosidase, granulocyte macrophage colony stimulating factor (GM-CSF), chorionic gonadotropin (hCG), hemoglobins, hepatitis B vaccines, hirudin, hyaluronidases, idumonidase, immune globulins, influenza vaccines, interleukines (1 alfa, 1 beta, 2, 3, 4, 6, 10, 11, 12), IL-1 receptor antagonist (rhIL-1ra), insulins, interferons (alfa 2a, alfa 2b, alfa 2c, beta 1a, beta 1b, gamma 1a, gamma 1b), keratinocyte growth factor (KGF), lactase, leuprolide, levothyroxine, luteinizing hormone, lyme vaccine, natriuretic peptide, pancrelipase, papain, parathyroid hormone, PDGF, pepsin, phospholipase-activating protein (PLAP), platelet activating factor alcetylhydrolase (PAF-AH), prolactin, protein C, octreotide, secretin, sermorelin, superoxide dismutase (SOD), somatropins (growth hormone), somatostatin, streptokinase, sucrase, tetanus toxin fragment, tilactase, thrombins, thymosin, thyroid stimulating hormone, thyrothropin, transforming growth factors, tumor necrosis factor (TNF), TNF receptor-IgG Fc, tissue plasminogen activator (tPA), transferrin, TSH, urate oxidase and urokinase.

If the drug is an antibody, it may be a monoclonal or polyclonal antibody or a fragment or fusion thereof. Preferred antibody fragments are selected from the group comprising Fab (fragment, antigen-binding), F(ab)$_2$ fragments, Fc (fragment, crystallizable), pFc' fragment, Fv (fragment, variable), scFv (single-chain variable fragment), di-scFv/diabodies, bi-specific T-cell engager, CDRs (complementarity determining regions), single-domain antibodies (sdABs/Nanobodies), heavy chains ($\alpha$, $\delta$, $\epsilon$, $\gamma$, $\mu$) or heavy chain fragments, light chains ($\lambda$, $\kappa$) or light chain fragments, VH fragments (variable region of the heavy chain), VL fragments (variable region of the light chain), VHH fragments and VNAR fragments.

If the drug is an affinity scaffold protein it is preferably selected from the group comprising shark-derived affinity scaffold proteins, Kunitz domain-derived affinity scaffold proteins, centyrin-derived affinity scaffold proteins, ubiquitin-derived affinity scaffold proteins, lipocalin-derived affinity scaffold proteins, ankyrin-derived affinity scaffold proteins, versabodies (disulfide-rich affinity scaffold proteins), fibronectin-derived affinity scaffold proteins, cameloid-derived antibody fragments and affinity scaffold proteins, llama-derived antibody fragments and affinity scaffold proteins, transferrin-derived affinity scaffold proteins, and squash-type protease inhibitors with cysteine-knot scaffold-derived affinity scaffold proteins.

In another aspect, the present invention relates to a carrier-linked prodrug obtainable by a process for the preparation of a carrier-linked prodrug of the present invention.

Such carrier-linked prodrug releases drug molecules with a half-life ranging from 1 hour to twelve months, e.g. from 6 hours to twelve months, from twelve hours to eleven months, from one day to ten months, from three days to nine months, from six days to nine months, from one week to nine months, from two weeks to seven months, from three weeks to eight months, from four weeks to eight months, from six weeks to seven months, from eight weeks to seven months, from ten weeks to six months, from twelve weeks to six months or from sixteen weeks to five months.

Another aspect of the present invention is a pharmaceutical composition comprising the carrier-linked prodrugs of the present invention or a pharmaceutical salt thereof together with a pharmaceutically acceptable excipient.

Yet another aspect of the present invention is a carrier-linked prodrug of the present invention or a pharmaceutical composition comprising the carrier-linked prodrug of the present invention for use as a medicament.

Yet another aspect of the present invention is a method of treating, controlling, delaying or preventing in a mammalian patient, preferably in a human, in need of the treatment of one or more conditions comprising administering to said patient a therapeutically effective amount of the carrier-linked prodrug of the present invention or the pharmaceutical composition comprising the carrier-linked prodrug of the present invention or a pharmaceutically acceptable salt thereof.

EXAMPLES

Materials and Methods

Materials:

Amino 4-arm PEG5000 was obtained from JenKem Technology, Beijing, P. R. China. Cithrol™ DPHS (PEG-30 dipolyhydroxystearate) was obtained from Croda International Pic, Cowick Hall, United Kingdom. cis-1,4-cyclohexanedicaboxylic acid was obtained from TCI EUROPE N.V., Boerenveldseweg 6-Haven 1063, 2070 Zwijndrecht, Belgium.

Isopropylmalonic acid was obtained from ABCR GmbH & Co. KG, 76187 Karlsruhe, Germany.

Glutaric acid monobenzyl ester was obtained by IRIS Biotec GmbH, 95615 Marktredwitz, Germany.

N-(3-maleimidopropyl)-21-amino-4,7,10,13,16,19-hexaoxa-heneicosanoic acid pentafluorophenyl ester (maleimide-NH-PEG6-PFE) and N-(3-maleimidopropyl)-39-amino-4,7,10,13,16,19,22,25,28,31,34,37-dodecaoxa-nonatriacontanoic acid pentafluorophenyl ester (maleimide-NH-PEG12-PFE) was obtained from Biomatrik Inc., Jiaxing, P. R. China.

OxymaPure® (ethyl (hydroxyimino)cyanoacetate) and Fmoc-L-Asp(OtBu)-OH were purchased from Merck Biosciences GmbH, Schwalbach/Ts, Germany.

(5-methyl-2-oxo-1,3-dioxol-4-yl)-methyl 4-nitrophenyl carbonate was purchased from Chemzon Scientific Inc., Lachine, QC, Canada.

All other chemicals were from Sigma-ALDRICH Chemie GmbH, Taufkirchen, Germany.

Methods:

RP-HPLC was done on a 100×20 mm or 100×40 mm C18 ReproSil-Pur 300 ODS-3 5μ column (Dr. Maisch, Ammerbuch, Germany) connected to a Waters 600 or 2535 HPLC System and Waters 2487 or 2489 Absorbance detector, respectively. Linear gradients of solution A (0.1% TFA in H2O) and solution B (0.1% TFA in acetonitrile) were used. HPLC fractions containing product were combined and lyophilized.

Flash chromatography purifications were performed on an Isolera One system from Biotage AB, Sweden, using Biotage KP-Sil silica cartridges and n-heptane, ethyl acetate, and methanol as eluents. Products were detected at 254 nm. For products showing no absorbance above 240 nm fractions were screened by LC/MS.

Analytical ultra-performance LC (UPLC) was performed on a Waters Acquity system equipped with a Waters BEH300 C18 column (2.1×50 mm, 1.7 μm particle size) coupled to a LTQ Orbitrap Discovery mass spectrometer from Thermo Scientific.

HPLC-Electrospray ionization mass spectrometry (HPLC-ESI-MS) was performed on a Waters Acquity UPLC with an Acquity PDA detector coupled to a Thermo LTQ Orbitrap Discovery high resolution/high accuracy mass spectrometer equipped with a Waters ACQUITY UPLC BEH300 C18 RP column (2.1×50 mm, 300 A, 1.7 μm, flow: 0.25 mL/min; solvent A: UP-H$_2$0+0.04% TFA, solvent B: UP-Acetonitrile+0.05% TFA.

MS spectra of PEG products showed a series of $(CH_2CH_2O)_n$ moieties due to polydispersity of PEG staring materials. For easier interpretation only one single representative m/z signal is given in the examples.

Example 1

Synthesis of Backbone Reagent 1a, 1g, and 1h

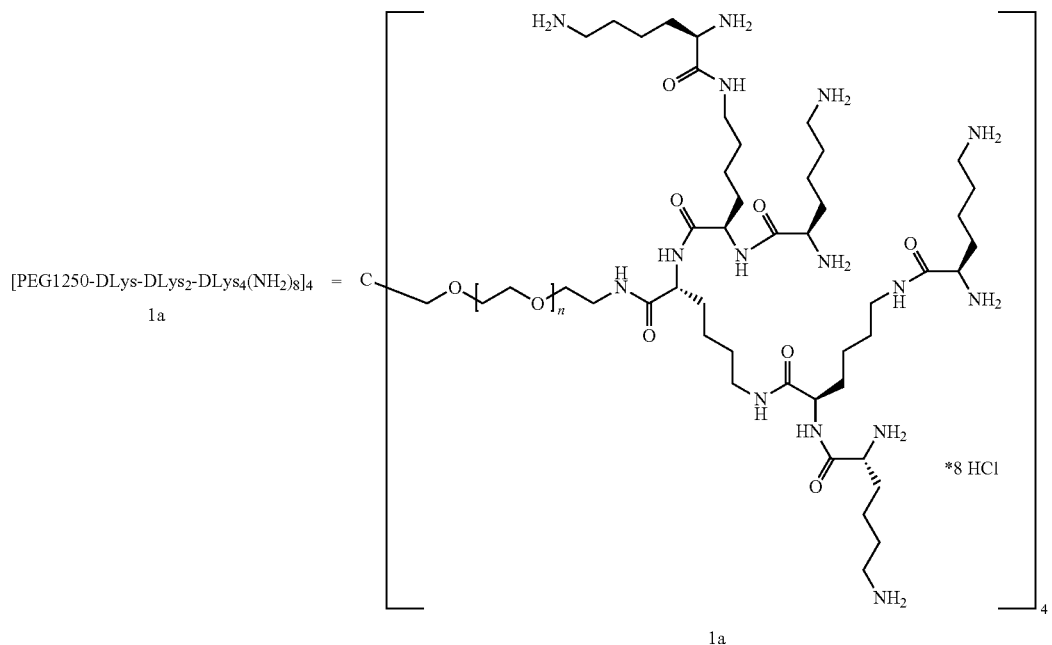

n~28

Backbone reagent 1a was synthesized as described in example 1 of WO 2011/012715 A1 except for the use of Boc-DLys(Boc)-OH instead of Boc-LLys(Boc)-OH.

MS: m/z 888.50=[M+10H$^+$]$^{10+}$ (calculated=888.54)

bis(pentafluorophenyl)carbonate (4.73 g, 12.0 mmol) were dissolved in 43 mL of DCM (anhydrous) and DIPEA (3.10 g, 24.0 mmol, 4.18 mL) was added at room temperature. After 10 min, 1,9-bis-boc-1,5,9-triazanonane (5.30 g, 16.0

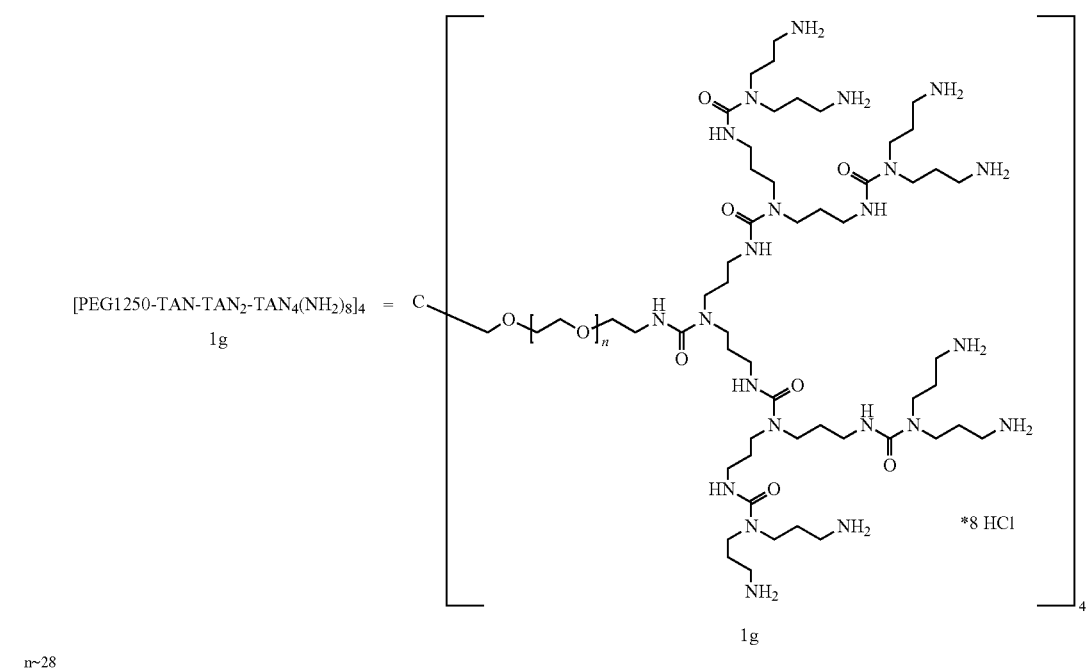

n~28

Backbone reagent 1g was synthesized from amino 4-arm PEG5000 1b according to the following scheme:

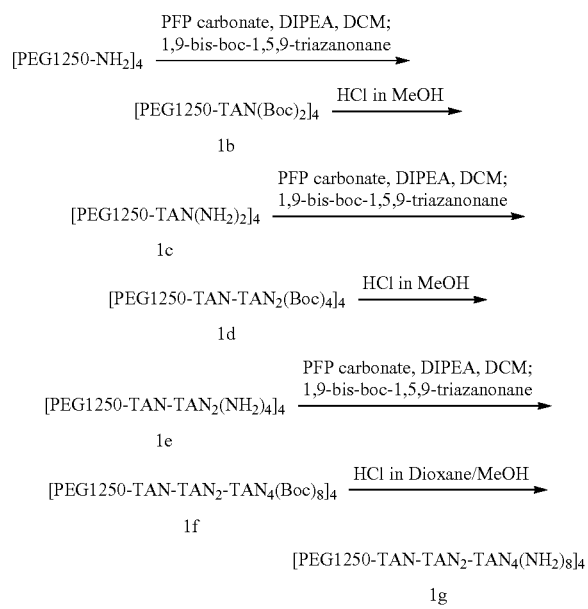

For synthesis of compound 1b, amino 4-arm PEG5000 (MW ca. 5350 g/mol, 10.7 g, 2.00 mmol, HCl salt) and mmol) was added and the mixture was stirred for 15 min. Then additional 1,9-bis-boc-1,5,9-triazanonane (0.33 g, 1.0 mmol) was added. After complete dissolution, the reaction mixture was filtered and the solvent was evaporated at room temperature.

The residue was dissolved in 40 mL iPrOH and diluted with 320 mL MTBE. The product was precipitated over night at −20° C. The precipitate was collected by filtration through a glass filter Por. 3, and washed with 200 mL of cooled MTBE (0° C.). The product was dried in vacuo over night.

Yield 11.1 g (83%) white solid 1b.

MS: m/z 1112.86=[M+6H]$^{6+}$ (calculated=1113.04).

For synthesis of compound 1c, the boc-protected compound 1b (11.1 g, 1.66 mmol) was dissolved in 40 mL of 3 M HCl in MeOH and stirred for 20 min at 45° C., then for 10 min at 55° C. For precipitation, 10 mL MeOH and 200 mL of MTBE were added and the mixture was stored for 16 h at −20° C. The precipitate was collected by filtration through a glass filter Por. 3 and washed with 200 mL of cooled MTBE (0° C.). The product was dried in vacuo over night.

Yield 9.14 g (89%) white powder 1c (HCl salt).

MS: m/z 979.45=[M+6H]$^{6+}$ (calculated=979.55).

For synthesis of compound 1d, compound 1c (9.06 g, 1.47 mmol, HCl salt) and bis(pentafluorophenyl)carbonate (6.95 g, 17.6 mmol) were dissolved in 50 mL of DCM (anhydrous) and DIPEA (4.56 g, 35.3 mmol, 6.15 mL) was added at room temperature. After 10 min, 1,9-bis-boc-1,5,9-triazanonane (7.80 g, 23.5 mmol) was added and the mixture was stirred for 15 min. Then additional 1,9-bis-boc-1,5,9-triazanonane (0.49 g, 1.5 mmol) was added. After complete dissolution, the solvent was evaporated at room temperature.

The residue was dissolved in 35 mL iPrOH at 40° C. and diluted with 200 mL MTBE. The product was precipitated over night at −20° C. The precipitate was collected by filtration through a glass filter Por. 3, and washed with 200 mL of cooled MTBE (0° C.). The product was dried in vacuo over night to give 1d as a white solid.

Yield 11.6 g (90%) white solid 1d.

MS: m/z 1248.08=$[M+7H]^{7+}$ (calculated=1248.27).

For synthesis of compound 1e, the boc-protected compound 1d (11.4 g, 1.31 mmol) was dissolved in 40 mL of 3 M HCl in MeOH and stirred for 20 min at 45° C., then for 10 min at 55° C. For precipitation, 10 mL MeOH and 200 mL of MTBE were added and the mixture was stored for 16 h at −20° C. The precipitate was collected by filtration through a glass filter Por. 3 and washed with 200 mL of cooled MTBE (0° C.). The product was dried in vacuo over night to give white powder 1e.

Yield 7.60 g (75%) white powder 1e (HCl salt).

MS: m/z 891.96=$[M+8H]^{8+}$ (calculated=892.13).

For synthesis of compound 1f, compound 1e (7.56 g, 0.980 mmol, HCl salt) and bis(pentafluorophenyl)carbonate (9.27 g, 23.0 mmol) were dissolved in 250 mL of DCM (anhydrous) and DIPEA (6.08 g, 47.0 mmol, 8.19 mL) was added at 35° C. After 10 min, 1,9-bis-boc-1,5,9-triazanonane (5.30 g, 16.0 mmol) was added and the mixture was stirred for 15 min. Then additional 1,9-bis-boc-1,5,9-triazanonane (0.33 g, 1.0 mmol) was added. After complete dissolution, the solvent was evaporated at room temperature.

The residue was dissolved in 250 mL iPrOH at 60° C. and diluted with 1350 mL MTBE. The product was precipitated over night at −20° C. The precipitate was collected by filtration through a glass filter Por. 3, and washed with 400 mL of cooled MTBE (0° C.). The product was dried in vacuo over night to give 1f as a glassy solid.

Yield 11.1 g (83%) glassy solid 1f.

MS: m/z 1312.01=$[M+10H]^{10+}$ (calculated=1312.21).

For synthesis of backbone reagent 1g, the boc-protected compound 1f (7.84 g, 0.610 mmol) was dissolved in 16 mL of MeOH at 37° C. and 55 mL of a precooled solution of 4 M HCl (4° C.) in dioxane was added at room temperature. The mixture was stirred without cooling for 20 min. After 20 min 110 mL of 3M HCl in MeOH was added. The solution was partitioned in 24 Falcon tubes (50 mL) and precipitated with by adding 40 mL cold MTBE (−20° C.) to each Falcon tube. After centrifugation at 3214 rcf for 1 min, the supernatant was decanted and the glassy solid was dissolved in 5 mL MeOH per Falcon tube and precipitated by adding 40 mL cold MTBE (−20° C.) to each Falcon tube again. The supernatant was discarded and the remaining solid was dried in vacuo over night.

Yield 5.74 g (87%) white glassy solid 1g (HCl salt).

MS: m/z 965.46=$[M+10H]^{10+}$ (calculated=965.45).

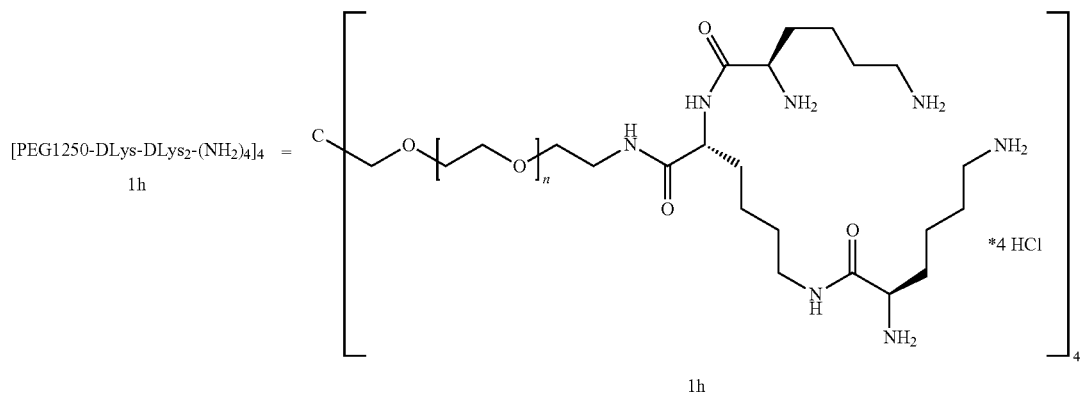

n~28

Backbone reagent 1 h was synthesized as described for compound 1e in example 1 of WO 2011/012715 A1 except for the use of Boc-DLys(Boc)-OH instead of Boc-LLys(Boc)-OH.

MS: m/z 848.52=$[M+8H]^{8+}$ (calculated=848.57)

Example 2

Synthesis of crosslinker reagents 2d, 2g, rac-2k, rac-2o, 2s, 2v, rac-2y, 2ac, 2ag, and 2ak Crosslinker reagent 2e was prepared from azelaic acid monobenzyl ester and PEG 10000 according to the following scheme:

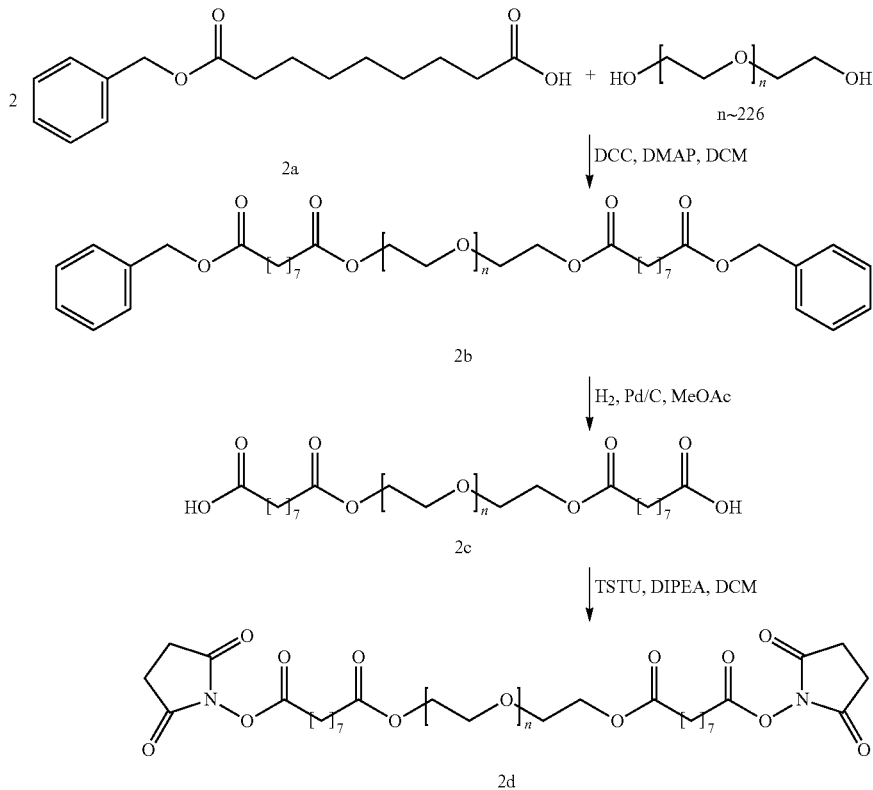

with an ice bath. A solution of DCC (2.89 g, 14.0 mmol) and DMAP (0.024 g, 0.020 mmol) in 32 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 65 mL dichloromethane and diluted with 308 mL MTBE at room temperature. The mixture was stored over night at −20° C. The precipitate was collected by filtration through a glass filter Por. 3, and washed with 250 mL of cooled MTBE (−20° C.).

The product was dried in vacuo over night.

Yield 40.8 g (97%) white powder 2b.

MS: m/z 835.50=$[M+14H]^{14+}$ (calculated=835.56).

For the synthesis of azelaic acid monobenzyl ester 2a, a mixture of azelaic acid (37.6 g, 200 mmol), benzyl alcohol (21.6 g, 200 mmol), p-toluenesulfonic acid (0.80 g, 4.2 mmol), and 240 mL toluene was refluxed for 7 h in a Dean-Stark apparatus. After cooling down, the solvent was evaporated and 300 mL sat. aqueous $NaHCO_3$ solution were added. This mixture was extracted with 3×200 mL MTBE. The combined organic phases were dried over $Na_2SO_4$ and the solvent was evaporated. The product was purified on 2×340 g silica using ethyl acetate/heptane (10:90→25:75) as eluent. The eluent was evaporated and the residue was dried in vacuo over night.

Yield 25.8 g (46%) colorless oil 2a.

MS: m/z 279.16=$[M+H]^+$ (calculated=279.16).

For synthesis of compound 2b, azelaic acid monobenzyl ester 2a (3.90 g, 14.0 mmol) and PEG 10000 (40.0 g, 4.00 mmol) were dissolved in 64 mL dichloromethane and cooled For synthesis of compound 2c, compound 2b (40.6 g, 3.86 mmol) was dissolved in methyl acetate (250 mL) and 203 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield 37.2 g (93%) glassy solid 2c.

MS: m/z 882.53=$[M+13H]^{13+}$ (calculated=882.51).

For synthesis of compound 2d, compound 2c (32.0 g, 3.10 mmol) and TSTU (3.73 g, 12.4 mmol) were dissolved in 150 mL dichloromethane at room temperature. Then DIPEA (1.60 g, 12.4 mmol) was added and the mixture was stirred for 1 h. The resulting suspension was filtered and the filtrate was diluted with 170 mL dichloromethane, washed with 140 mL of a solution of 750 g water/197 g NaCl/3 g NaOH. The organic phase was dried over MgSO₄ and the solvent was evaporated in vacuo.

The residue was dissolved in 200 mL toluene, diluted with 180 mL MTBE at room temperature and stored over night at −20° C. The precipitate was collected by filtration through a glass filter Por. 3, and washed with 100 mL of cooled MTBE (−20° C.). The product was dried in vacuo over night.

Yield 28.8 g (88%) white powder 2d.

MS: m/z 795.47=[M+15H]$^{15+}$ (calculated=795.54).

Crosslinker reagent 2g was prepared from azelaic acid monobenzyl ester and PEG6000 according to the following scheme:

ethanol (40 mL), then 400 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield 38.4 g (96%) glassy solid 2f.

MS: m/z 750.46=[M+9H]$^{9+}$ (calculated=750.56).

For synthesis of compound 2g, compound 2f (38.2 g, 6.02 mmol) and TSTU (7.25 g, mmol) were dissolved in 130 mL dichloromethane at room temperature. Then DIPEA (3.11 g, 24.1 mmol) was added and the mixture was stirred for 1 h.

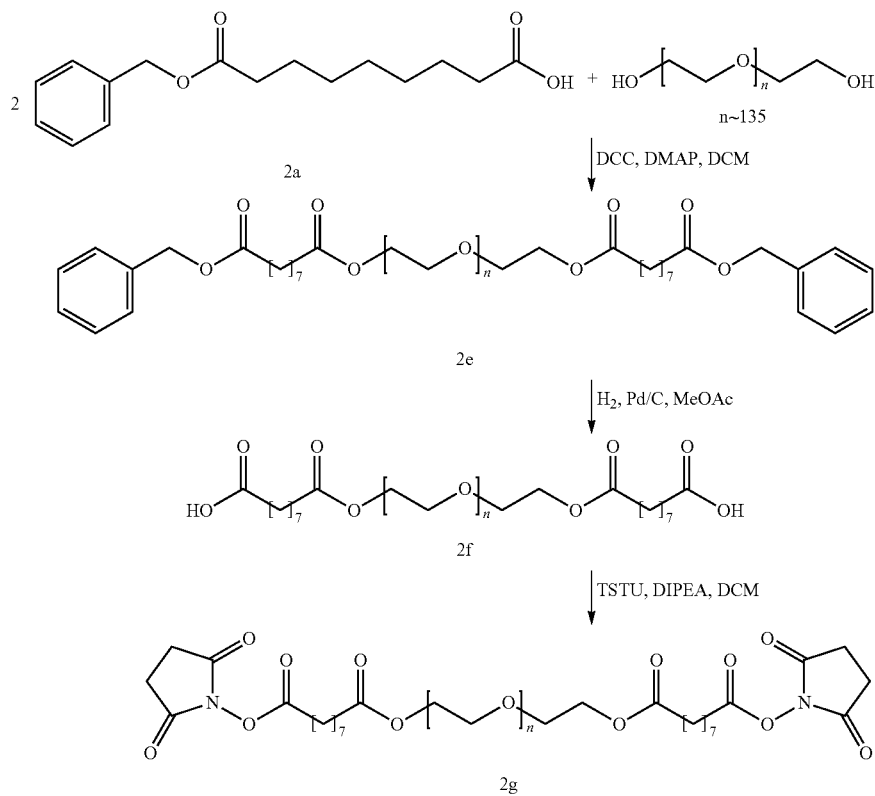

For synthesis of compound 2e, azelaic acid monobenzyl ester 2a (6.50 g, 23.3 mmol) and PEG 6000 (40.0 g, 6.67 mmol) were dissolved in 140 mL dichloromethane and cooled with an ice bath. A solution of DCC (4.81 g, 23.3 mmol) and DMAP (0.040 g, 0.33 mmol) in 40 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 70 mL dichloromethane and diluted with 300 mL MTBE at room temperature. The mixture was stored over night at −20° C. The precipitate was collected by filtration through a glass filter Por. 3, and washed with 500 mL of cooled MTBE (−20° C.).

The product was dried in vacuo over night.

Yield 41.2 g (95%) white powder 2e.

MS: m/z 833.75=[M+8H]$^{8+}$ (calculated=833.74).

For synthesis of compound 2f, compound 2e (41.2 g, 6.32 mmol) was dissolved in methyl acetate (238 mL) and The resulting suspension was filtered, the filtrate was diluted with 100 mL dichloromethane and washed with 200 mL of a solution of 750 g water/197 g NaCl/3 g NaOH. The organic phase was dried over MgSO₄ and the solvent was evaporated in vacuo.

The residue was dissolved in 210 mL toluene, diluted with 430 mL MTBE at room temperature and stored over night at −20° C. The precipitate was collected by filtration through a glass filter Por. 3, and washed with 450 mL of cooled MTBE (−20° C.). The product was dried in vacuo over night.

Yield 35.8 g (91%) white powder 2g.

MS: m/z 857.51=[M+8H]$^{8+}$ (calculated=857.51).

Crosslinker reagent 2k was prepared from isopropylmalonic acid monobenzyl ester and PEG10000 according to the following scheme:

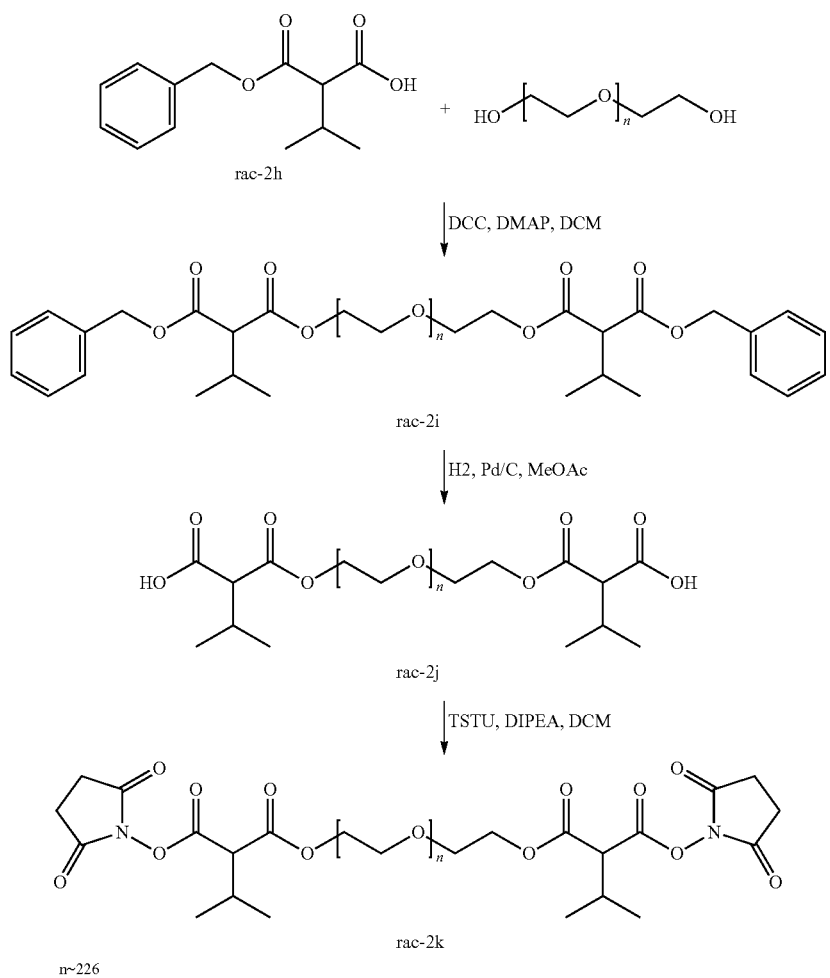

n~226

For the synthesis of isopropylmalonic acid monobenzyl ester rac-2h, isopropylmalonic acid (35.0 g, 239 mmol), benzyl alcohol (23.3 g, 216 mmol) and DMAP (1.46 g, 12.0 mmol) were dissolved in 100 mL acetonitrile. Mixture was cooled to 0° C. with an ice bath. A solution of DCC (49.4 g, 239 mmol) in 150 mL acetonitrile was added within 15 min at 0° C. The ice bath was removed and the reaction mixture was stirred over night at room temperature, then the solid was filtered off. The filtrate was evaporated at 40° C. in vacuo and the residue was dissolved in 300 mL MTBE. This solution was extracted with 2×300 mL sat. aqueous NaHCO₃ solution, then the combined aqueous phases were acidified to pH=1-3 using 6 N hydrochloric acid. The resulting emulsion was extracted with 2×300 mL MTBE and the solvent was evaporated. The combined organic phases were washed with 200 mL sat. aqueous NaCl and dried over MgSO₄. The product was purified on 340 g silica using ethyl acetate/heptane (10:90→20:80) as eluent. The eluent was evaporated and the residue was dried in vacuo over night.

Yield 9.62 g (17%) colorless oil rac-2h.

MS: m/z 237.11=[M+H]$^+$ (calculated=237.11).

For synthesis of compound rac-2i, isopropylmalonic acid monobenzyl ester rac-2h (945 mg, 4.00 mmol) and PEG 10000 (10.0 g, 4.00 mmol) were dissolved in 20 mL dichloromethane and cooled with an ice bath. A solution of DCC (825 mg, 4.00 mmol) and DMAP (6 mg, 0.05 mmol) in 10 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 20 mL dichloromethane and diluted with 150 mL MTBE at room temperature. The mixture was stored over night at −20° C. The precipitate was collected by filtration through a glass filter Por. 3, and washed with 500 mL of cooled MTBE (−20° C.).

The product was dried in vacuo over night.

Yield 9.63 g (92%) white powder rac-2i.

MS: m/z 742.50=[M+16H]$^{16+}$ (calculated=742.51).

For synthesis of compound rac-2j, compound rac-2i (3.38 g, 0.323 mmol) was dissolved in methyl acetate (100 mL) and 105 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield 3.25 g (98%) glassy solid rac-2j.

MS: m/z 731.25=[M+16H]$^{16+}$ (calculated=731.25).

For synthesis of compound rac-2k, compound rac-2j (3.10 g, 0.302 mmol) and TSTU (0.364 g, 1.21 mmol) were dissolved in 15 mL dichloromethane at room temperature. Then DIPEA (0.156 g, 1.21 mmol) was added and the mixture was stirred for 45 min. The resulting suspension was filtered and the filtrate was washed with 2×10 mL of a 0.5 M phosphate buffer pH=6.5. The organic phase was dried over MgSO$_4$ and the solvent was evaporated in vacuo. The residue was dissolved in 20 mL toluene, diluted with 10 mL MTBE at room temperature and stored over night at −20° C. The precipitate was collected by filtration through a glass filter Por. 3, and washed with 250 mL of cooled MTBE (−20° C.). The product was dried in vacuo over night.

Yield 2.66 g (84%) white powder rac-2k.

MS: m/z 743.37=[M+16H]$^{16+}$ (calculated=743.38).

Crosslinker reagent rac-2o was prepared from cis-1,4-cyclohexanedicarboxylic acid and PEG10000 according to the following scheme:

solution of DCC (49.4 g, 239 mmol) in 100 mL THF was added within 15 min at 0° C. The ice bath was removed and the reaction mixture was stirred over night at room temperature, then the solid was filtered off. The filtrate was evaporated at 40° C. and the residue was dissolved in 300 mL MTBE. This solution was extracted with 2×300 mL sat. aqueous NaHCO$_3$ solution, then the combined aqueous phases were acidified to pH=1-3 using 6 N hydrochloric acid. The resulting emulsion was extracted with 2×300 mL MTBE and the solvent was evaporated. The combined organic phases were washed with 200 mL sat. aqueous NaCl and dried over MgSO$_4$. The product was purified on 340 g silica using ethyl acetate/heptane (10:90→20:80) as eluent.

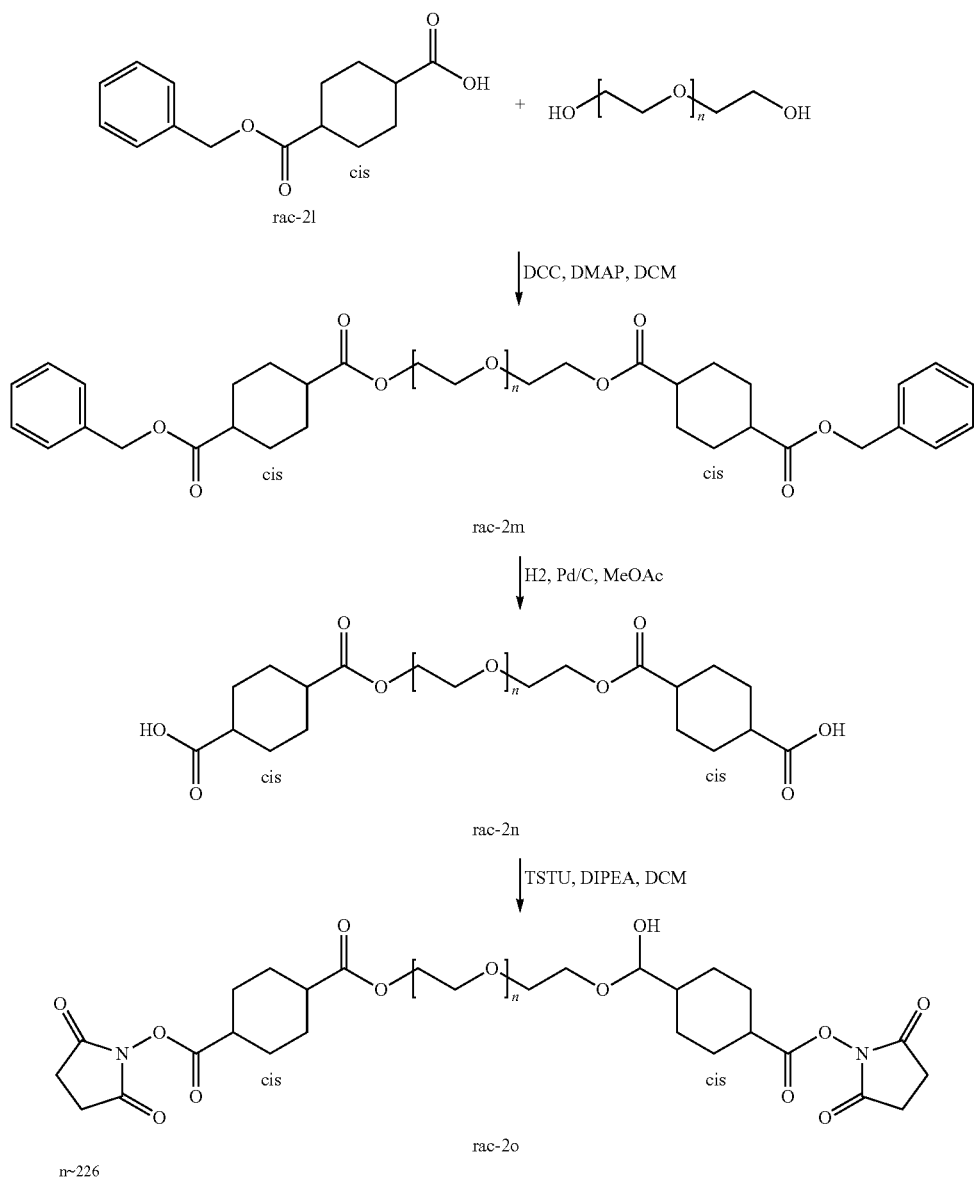

For the synthesis of cis-1,4-cyclohexanedicarboxylic acid monobenzyl ester rac-2l, cis-1,4-cyclohexanedicarboxylic acid (20.0 g, 116 mmol), benzyl alcohol (11.3 g, 105 mmol) and DMAP (710 mg, 5.81 mmol) were dissolved in 200 mL THF. Mixture was cooled to 0° C. with an ice bath. A The eluent was evaporated and the colorless oily residue crystallized during drying in vacuo over night.

Yield 4.82 g (16%) colorless crystals rac-2l.

MS: m/z 263.13=[M+H]$^+$ (calculated=263.13).

For synthesis of compound rac-2m, cis-1,4-cyclohexanedicarboxylic acid monobenzyl ester rac-2l (2.10 g, 8.00 mmol) and PEG 10000 (20.0 g, 10.0 mmol) were dissolved in 50 mL dichloromethane and cooled with an ice bath. A solution of DCC (1.65 g, 8.00 mmol) and DMAP (0.012 g, 0.10 mmol) in 25 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 55 mL dichloromethane and diluted with 300 mL MTBE at room temperature. The mixture was stored over night at −20° C. The precipitate was collected by filtration through a glass filter Por. 3, and washed with 250 mL of cooled MTBE (−20° C.).

filtered and the filtrate was washed with 2×10 mL of a 0.5 M phosphate buffer pH=6.5. The organic phase was dried over $MgSO_4$ and the solvent was evaporated in vacuo.

The residue was dissolved in 50 mL toluene, diluted with 25 mL MTBE at room temperature and stored over night at −20° C. The precipitate was collected by filtration through a glass filter Por. 3, and washed with 400 mL of cooled MTBE (−20° C.). The product was dried in vacuo over night.

Yield 7.62 g (84%) white powder rac-2o.

MS: m/z 702.60=$[M+16H]^{16+}$ (calculated=702.59).

Crosslinker reagent 2s was prepared from suberic acid monobenzyl ester and PEG10000 accordingly to the following scheme:

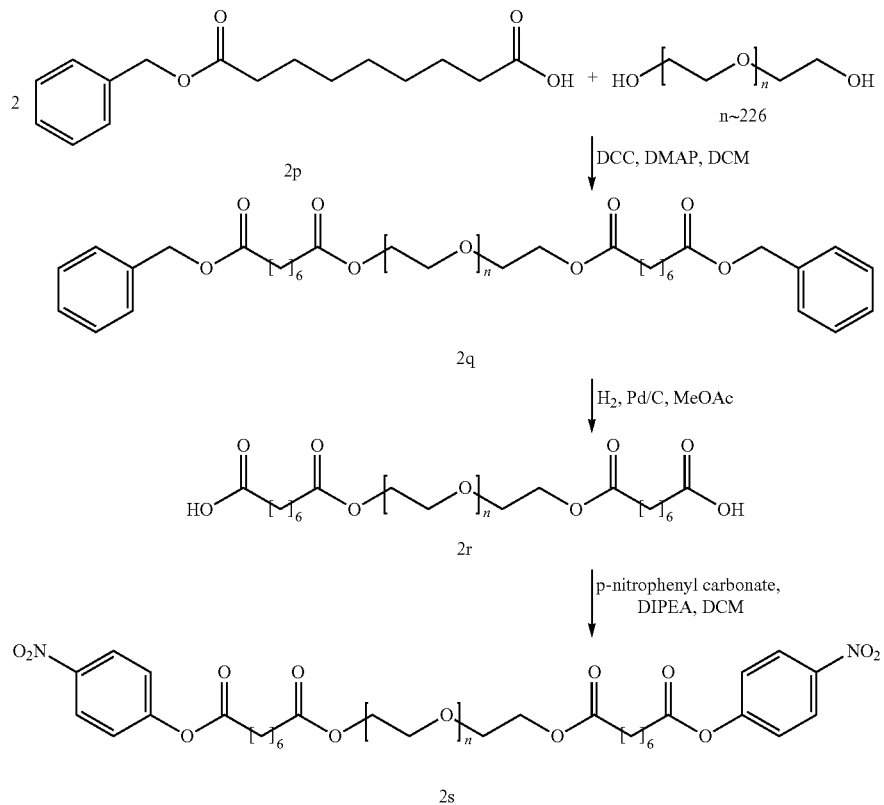

The product was dried in vacuo over night.

Yield 18.2 g (87%) white powder rac-2m.

MS: m/z 745.76=$[M+16H]^{16+}$ (calculated=745.77).

For synthesis of compound rac-2n, compound rac-2m (9.00 g, 0.857 mmol) was dissolved in methyl acetate (100 mL) and 157 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield 8.83 g (100%) glassy solid rac-2n.

MS: m/z 734.50=$[M+16H]^{16+}$ (calculated=734.50).

For synthesis of compound rac-2o, compound rac-2n (8.92 g, 0.864 mmol) and TSTU (1.04 g, 3.64 mmol) were dissolved in 35 mL dichloromethane at room temperature. Then DIPEA (0.447 g, 3.46 mmol) was added and the mixture was stirred for 45 min. The resulting suspension was Suberic acid monobenzyl ester 2p was synthesized from suberic acid and benzyl alcohol accordingly to azelaic acid monobenzyl ester 2a.

Compound 2q was synthesized accordingly to the PEG derivative 2b from suberic acid monobenzyl ester 2p and PEG 10000.

Compound 2r was synthesized accordingly to the PEG derivative 2c from compound 2q.

For synthesis of compound 2s, compound 2r (18.0 g, 1.74 mmol) and p-nitrophenyl carbonate (2.12 g, 6.76 mmol) were dissolved in 70 mL acetonitrile at RT. Then DIPEA (0.90 g, 6.76 mmol) in 1.0 mL dichloromethane was added and the mixture was stirred for 17 h. The mixture was diluted with 270 mL MTBE at RT and stored over night at −20° C. The precipitate was collected by filtration through a glass filter Por. 3, and washed with 200 mL of cooled MTBE (−20° C.). The product was dried in vacuo over night.

Yield 17.6 g (96%) pale yellow powder 2s.

MS: m/z 822.20=[M+14H]$^{14+}$ (calculated=822.25).

Crosslinker reagent 2v was prepared from suberic acid monobenzyl ester 2p and PEG6000 accordingly to the following scheme:

Then DIPEA (0.20 g, 1.52 mmol) in 0.14 mL dichloromethane was added and the mixture was stirred for 1 h. The mixture was diluted with 26 mL MTBE at room temperature and stored over night at −20° C. The precipitate was collected by filtration through a glass filter Por. 3, and

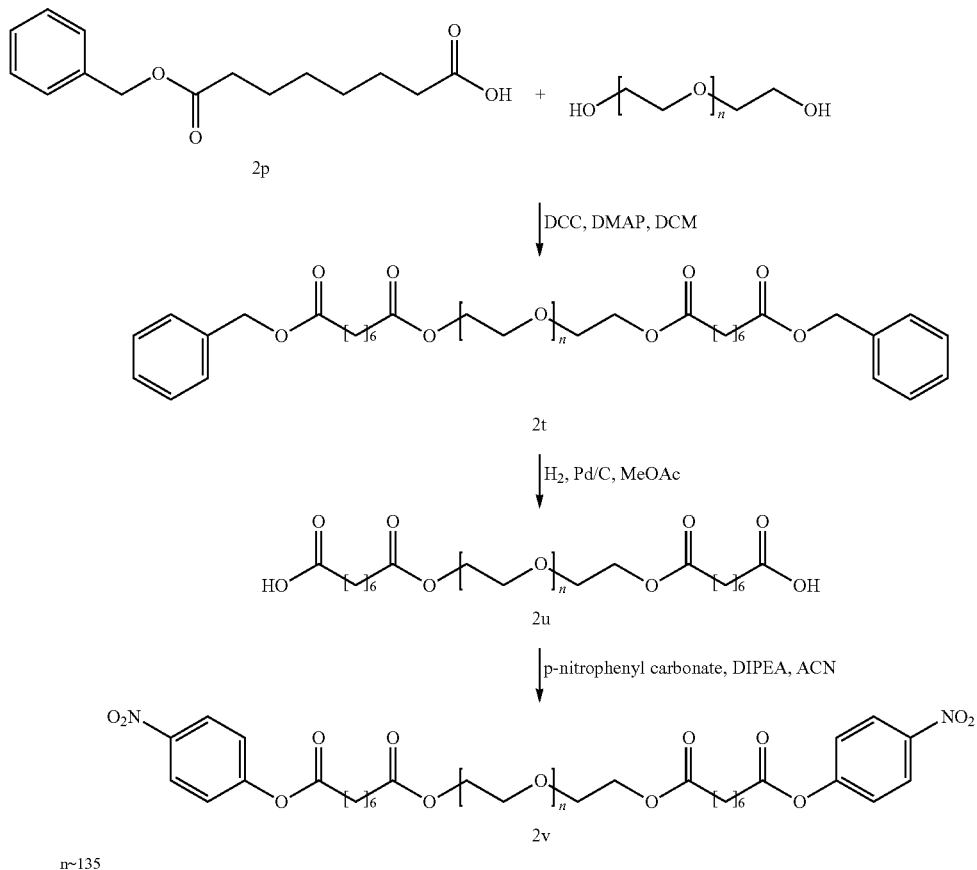

Compound 2t was synthesized accordingly to the PEG derivative 2b from suberic acid monobenzyl ester 2p and PEG6000.

Compound 2u was synthesized accordingly to the PEG derivative 2c from compound 2t.

For synthesis of compound 2v, compound 2u (2.40 g, 0.38 mmol) and p-nitrophenyl carbonate (4.61 g, 1.52 mmol) were dissolved in 6 mL acetonitrile at room temperature.

washed with 100 mL of cooled MTBE (−20° C.). The product was dried in vacuo over night.

Yield 2.37 g (95%) pale yellow powder 2v.

MS: m/z 774.34=[M+9H]$^{9+}$ (calculated=774.34).

Crosslinker reagent 2y was prepared from isopropylmalonic acid monobenzyl ester and PEG8000 according to the following scheme:

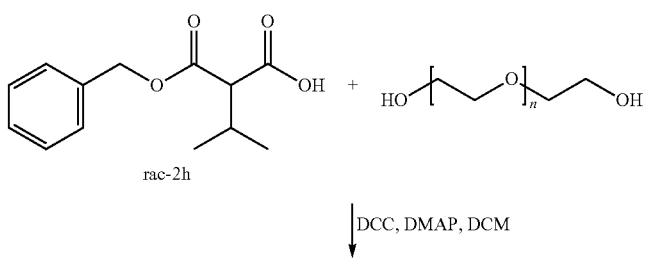

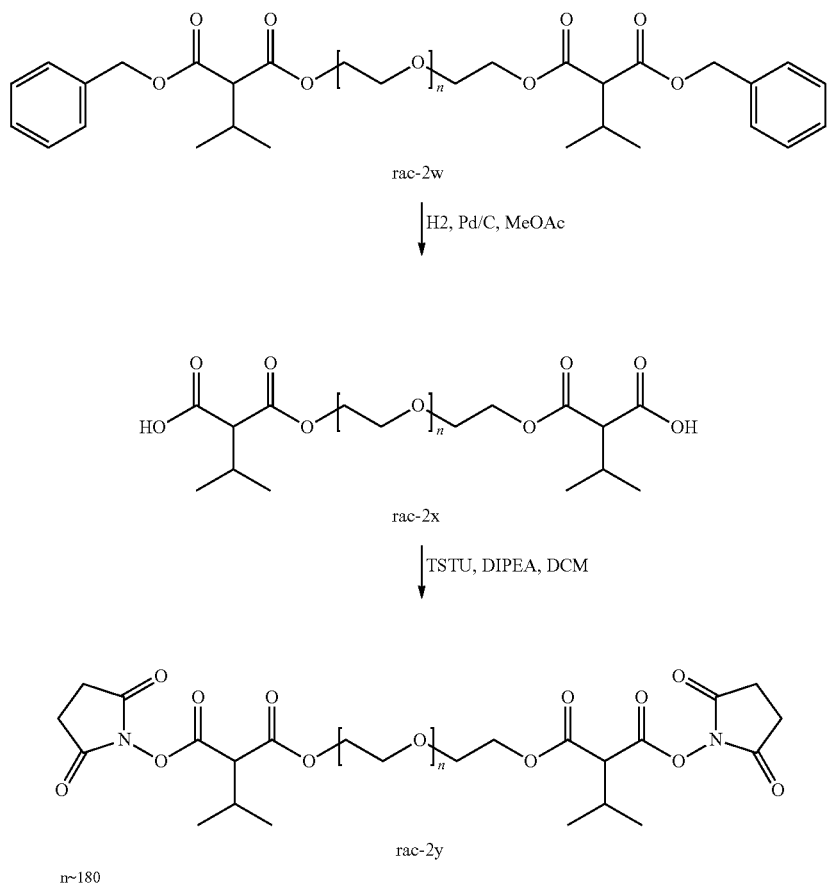

rac-2w rac-2x rac-2y n~180

For synthesis of compound rac-2w, isopropylmalonic acid monobenzyl ester rac-2h (2.25 g, 9.50 mmol) and PEG 8000 (19.0 g, 2.38 mmol) were dissolved in 100 mL dichloromethane and cooled with an ice bath. A solution of DCC (1.96 g, 9.50 mmol) and DMAP (14 mg, 0.12 mmol) in 10 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 40 mL dichloromethane and diluted with 270 mL MTBE at room temperature. The mixture was stored over night at −20° C. The precipitate was collected by filtration through a glass filter Por. 3, and washed with 500 mL of cooled MTBE (−20° C.).

The product was dried in vacuo over night.

Yield 18.5 g (92%) white powder rac-2w.

MS: m/z 737.43=[M+13H]$^{13+}$ (calculated=737.42).

For synthesis of compound rac-2x, compound rac-2w (18.4 g, 2.18 mmol) was dissolved in methyl acetate (160 mL) and 254 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield 17.7 g (98%) glassy solid rac-2x.

MS: m/z 723.51=[M+13H]$^{13+}$ (calculated=723.55).

For synthesis of compound rac-2y, compound rac-2x (13.6 g, 1.65 mmol) and TSTU (1.96 g, 6.60 mmol) were dissolved in 60 mL dichloromethane at room temperature. Then DIPEA (852 mg, 6.60 mmol) was added and the mixture was stirred for 45 min. The resulting suspension was filtered, the filtrate was diluted with 70 mL ethyl acetate and washed with 70 mL of a 0.5 M phosphate buffer pH=6.5. The organic phase was dried over MgSO$_4$ and the solvent was evaporated in vacuo. The residue was dissolved in 80 mL toluene, the remaining solid was filtered off and washed with 20 mL of toluene. The combined toluene fractions were diluted with 35 mL MTBE at room temperature and stored over night at −20° C. The precipitate was collected by filtration through a glass filter Por. 3, and washed with 600 mL of cooled MTBE (−20° C.). The product was dried in vacuo over night.

Yield 12.1 g (87%) white powder rac-2y.

MS: m/z 738.51=[M+13H]$^{13+}$ (calculated=738.49).

Crosslinker reagent 2ac was prepared from sebacic acid monobenzyl ester and PEG 10000 according to the following scheme:

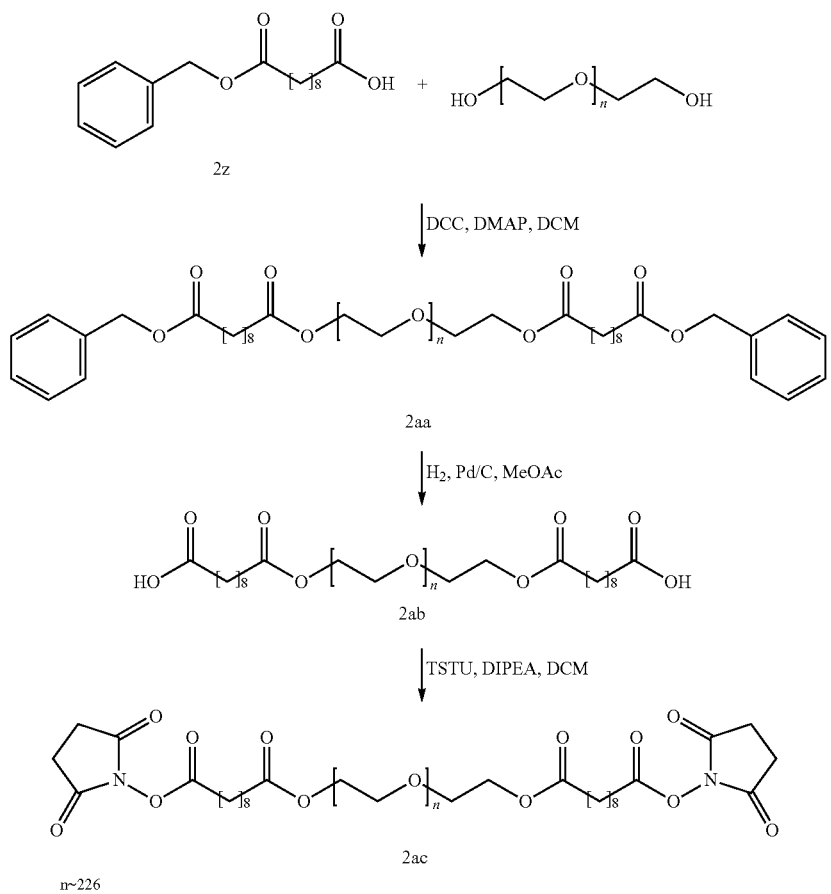

n~226

For the synthesis of sebacic acid monobenzyl ester 2z, a mixture of sebacic acid (20.2 g, 100 mmol), benzyl alcohol (10.8 g, 100 mmol), p-toluenesulfonic acid (0.40 g, 2.1 mmol), and 120 mL toluene was refluxed for 19 h in a Dean-Stark apparatus. After cooling down, the solvent was evaporated and 150 mL sat. aqueous $NaHCO_3$ solution were added. This mixture was extracted with 3×100 mL MTBE. The combined organic phases were dried over $Na_2SO_4$ and the solvent was evaporated. The product was purified on 340 g silica using ethyl acetate/heptane (10:90→25:75) as eluent. The eluent was evaporated and the residue was dried in vacuo over night.

Yield 13.4 g (46%) colorless oil 2z.

MS: m/z 293.16=$[M+H]^+$ (calculated=293.16).

For synthesis of compound 2aa, sebacic acid monobenzyl ester 2z (1.02 g, 3.50 mmol) and PEG 10000 (10.0 g, 1.00 mmol) were dissolved in 40 mL dichloromethane and cooled with an ice bath. A solution of DCC (722 mg, 3.5 mmol) and DMAP (6.1 mg, 0.05 mmol) in 12 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 12 mL dichloromethane and diluted with 45 mL MTBE at room temperature. The mixture was stored over night at −20° C. The precipitate was collected by filtration through a glass filter Por. 3, and washed with 250 mL of cooled MTBE (−20° C.).

The product was dried in vacuo over night.

Yield 9.92 g (94%) white powder 2aa.

MS: m/z 793.48=$[M+15H]^{15+}$ (calculated=793.56).

For synthesis of compound 2ab, compound 2aa (9.83 g, 0.93 mmol) was dissolved in methyl acetate (100 mL) and 123 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield 9.14 g (95%) glassy solid 2ab.

MS: m/z 840.51=$[M+14H]^{14+}$ (calculated=840.44).

For synthesis of compound 2ac, compound 2ab (9.00 g, 0.87 mmol) and TSTU (1.05 g, 3.47 mmol) were dissolved in 30 mL dichloromethane at room temperature. Then DIPEA (449 mg, 3.47 mmol) was added and the mixture was stirred for 1 h. The resulting suspension was filtered and the filtrate was diluted with 30 mL dichloromethane, washed with 60 mL of a solution of 750 g water/197 g NaCl/3 g NaOH. The organic phase was dried over $MgSO_4$ and the solvent was evaporated in vacuo.

The residue was dissolved in 45 mL toluene, diluted with 35 mL MTBE at room temperature and stored over night at −20° C. The precipitate was collected by filtration through a glass filter Por. 3, and washed with 350 mL of cooled MTBE (−20° C.). The product was dried in vacuo over night.

Yield 8.29 g (90%) white powder 2ac.

MS: m/z 794.47=$[M+15H]^{15+}$ (calculated=794.48).

Crosslinker reagent 2ag was prepared from undecanedioic acid monobenzyl ester and PEG10000 according to the following scheme:

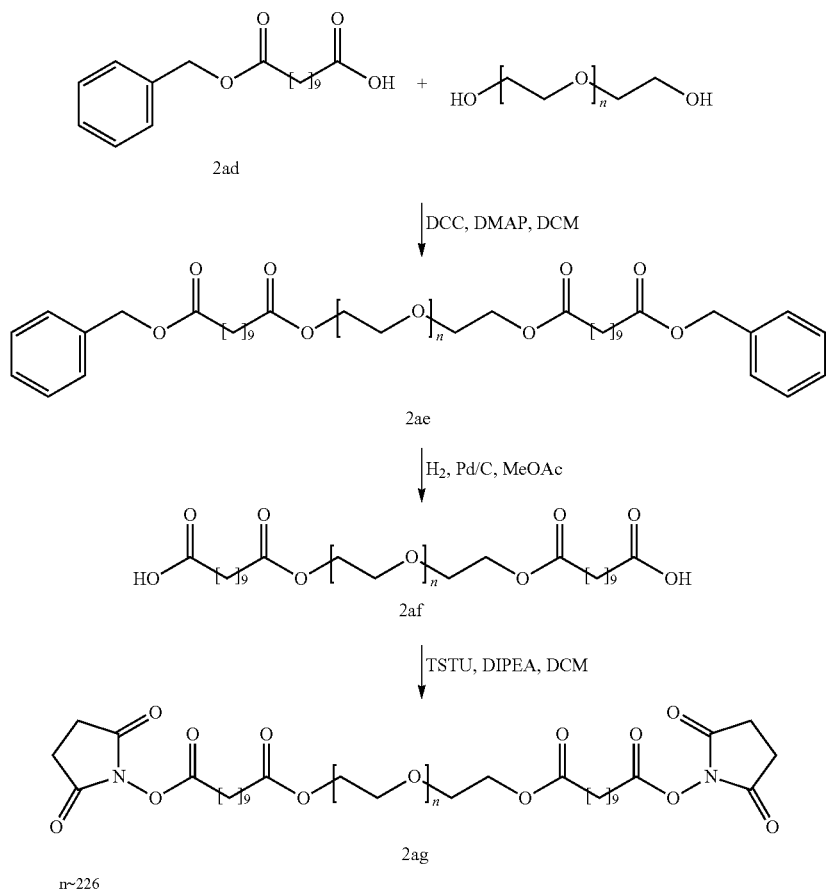

2ag n~226

For the synthesis of undecanedioic acid monobenzyl ester 2ad, a mixture of undecanedioic acid (21.6 g, 100 mmol), benzyl alcohol (10.8 g, 100 mmol), p-toluenesulfonic acid (0.40 g, 2.1 mmol), and 120 mL toluene was refluxed for 19 h in a Dean-Stark apparatus. After cooling down, the solvent was evaporated and 150 mL sat. aqueous $NaHCO_3$ solution were added. This mixture was extracted with 3×100 mL MTBE. The combined organic phases were dried over $Na_2SO_4$ and the solvent was evaporated. The product was purified on 340 g silica using ethyl acetate/heptane (10:90→25:75) as eluent. The eluent was evaporated and the residue was dried in vacuo over night.

Yield 14.8 g (48%) colorless oil 2ad.

MS: m/z 307.19=$[M+H]^+$ (calculated=307.19).

For synthesis of compound 2ae, undecanedioic acid monobenzyl ester 2ad (1.07 g, 3.50 mmol) and PEG 10000 (10.0 g, 1.00 mmol) were dissolved in 40 mL dichloromethane and cooled with an ice bath. A solution of DCC (722 mg, 3.5 mmol) and DMAP (6.1 mg, 0.05 mmol) in 12 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 13 mL dichloromethane and diluted with 43 mL MTBE at room temperature. The mixture was stored over night at -20° C. The precipitate was collected by filtration through a glass filter Por. 3, and washed with 250 mL of cooled MTBE (-20° C.).

The product was dried in vacuo over night.

Yield 10.0 g (95%) white powder 2ae.

MS: m/z 792.48=$[M+15H]^{15+}$ (calculated=792.49).

For synthesis of compound 2af compound 2ae (9.83 g, 0.93 mmol) was dissolved in methyl acetate (100 mL) and 103 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield 8.90 g (92%) glassy solid 2af.

MS: m/z 780.47=$[M+15H]^{15+}$ (calculated=780.47).

For synthesis of compound 2ag, compound 2af (8.75 g, 0.84 mmol) and TSTU (1.01 g, 3.37 mmol) were dissolved in 30 mL dichloromethane at room temperature. Then DIPEA (435 mg, 3.37 mmol) was added and the mixture was stirred for 1 h. The resulting suspension was filtered and the filtrate was diluted with 30 mL dichloromethane, washed with 60 mL of a solution of 750 g water/197 g NaCl/3 g NaOH. The organic phase was dried over $MgSO_4$ and the solvent was evaporated in vacuo.

The residue was dissolved in 38 mL toluene, diluted with 30 mL MTBE at room temperature and stored over night at -20° C. The precipitate was collected by filtration through a glass filter Por. 3, and washed with 350 mL of cooled MTBE (-20° C.). The product was dried in vacuo over night.

Yield 7.51 g (84%) white powder 2ag.

MS: m/z 793.48=$[M+14H]^{14+}$ (calculated=793.38).

Crosslinker reagent 2ak was prepared from glutaric acid monobenzyl ester and PEG 10000 according to the following scheme:

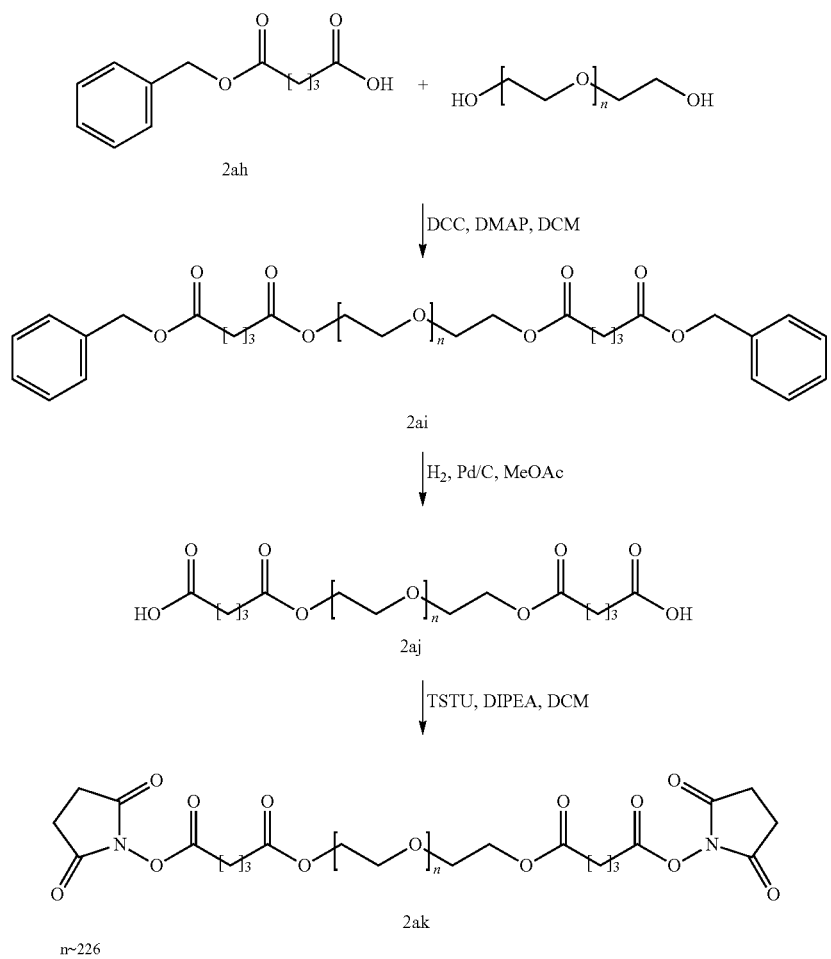

2ah

2ai

2aj

2ak n~226

For synthesis of compound 2ai, glutaric acid monobenzyl ester 2ah (1.95 g, 8.78 mmol) and PEG 10000 (25.1 g, 2.51 mmol) were dissolved in 70 mL dichloromethane and cooled with an ice bath. A solution of DCC (1.81 g, 8.78 mmol) and DMAP (15.3 mg, 0.13 mmol) in 18 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 70 mL dichloromethane and diluted with 360 mL MTBE at room temperature. The mixture was stored over night at −20° C. The precipitate was collected by filtration through a glass filter Por. 3, and washed with 500 mL of cooled MTBE (−20° C.).

The product was dried in vacuo over night.

Yield 24.9 g (95%) white powder 2ai.

MS: m/z 740.76=[M+16H]$^{16+}$ (calculated=740.76).

For synthesis of compound 2aj compound 2ai (24.9 g, 2.39 mmol) was dissolved in methyl acetate (220 mL) and 302 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield 24.3 g (99%) glassy solid 2aj.

MS: m/z 729.50=[M+16H]$^{16+}$ (calculated=729.49).

For synthesis of compound 2ak, compound 2aj (23.9 g, 2.33 mmol) and TSTU (2.81 g, 9.33 mmol) were dissolved in 100 mL dichloromethane at room temperature. Then DIPEA (1.21 g, 9.33 mmol) was added and the mixture was stirred for 1 h. The resulting suspension was filtered and the filtrate was diluted with 20 mL dichloromethane, washed with 120 mL of a solution of 750 g water/197 g NaCl/3 g NaOH. The organic phase was dried over MgSO$_4$ and the solvent was evaporated in vacuo.

The residue was dissolved in 125 mL toluene, diluted with 100 mL MTBE at room temperature and stored over night at −20° C. The precipitate was collected by filtration through a glass filter Por. 3, and washed with 650 mL of cooled MTBE (−20° C.). The product was dried in vacuo over night.

Yield 22.5 g (92%) white powder 2ak.

MS: m/z 741.63=[M+16H]$^{16+}$ (calculated=741.63).

Example 3

Preparation of Hydrogel Beads 3a, 3b, 3c, and 3d Containing Free Amino Groups

In a cylindrical 250 mL reactor with bottom outlet, diameter 60 min equipped with baffles, an emulsion of 218 mg Cithrol™ DPHS (PEG-30 dipolyhydroxystearate) in 100 mL undecane was stirred with an isojet stirrer, diameter 50 mm at 580 rpm, at ambient temperature. A solution of 250 mg 1a and 2205 mg 2d in 22.1 g DMSO was added and stirred for 10 min at RT to form a suspension. 1.1 mL TMEDA were added to effect polymerization. The mixture was stirred for 16 h. 1.7 mL of acetic acid were added and then after 10 min 100 mL of a 15w % solution of sodium chloride in water was added. After 10 min, the stirrer was stopped and phases were allowed to separate. After 2 h the aqueous phase containing the hydrogel was drained.

For bead size fractionation, the water-hydrogel suspension was diluted with 40 mL ethanol and wet-sieved on 125, 100, 75, 63, 50, 40, and 32 μm steel sieves using a Retsch AS200 control sieving machine for 15 min. Sieving amplitude was 1.5 mm, water flow 300 mL/min. Bead fractions that were retained on the 63 and 75 μm sieves were pooled and washed 3 times with 0.1% AcOH, 10 times with ethanol and dried for 16 h at 0.1 mbar to give 670 mg of 3a as a white powder.

Amino group content of the hydrogel was determined to be 0.145 mmol/g by conjugation of a fmoc-amino acid to the free amino groups on the hydrogel and subsequent fmoc-determination.

3b was prepared as described for 3a except for applying a stirrer speed of 560 rpm, the use of 350 mg 1a, 2548 mg 2g, 26.1 g DMSO, 257 mg Cithrol™ DPHS (PEG-30 dipolyhydroxystearate), 1.5 mL TMEDA, and 2.4 mL acetic acid, yielding 550 mg 3b as a white powder, free amino groups 0.120 mmol/g.

3c was prepared as described for 3a except for applying a stirrer speed of 560 rpm, the use of 250 mg 1a, 3019 mg rac-2k, 32.7 g DMSO, 290 mg Cithrol™ DPHS (PEG-30 dipolyhydroxystearate), 1.1 mL ml TMEDA, and 1.7 mL acetic acid, yielding 770 mg 3c as a white powder, free amino groups 0.126 mmol/g.

3d was prepared as described for 3a except for the use of 250 mg 1a, 2258 mg rac-2o, 22.6 g DMSO, 222 mg Cithrol™ DPHS (PEG-30 dipolyhydroxystearate), 1.1 mL ml TMEDA, and 1.7 mL acetic acid, yielding 186 mg 3d as a white powder, free amino groups 0.153 mmol/g.

3e was prepared as described for 3a except for the use of 250 mg 1a, 2168 mg rac-2y, 21.8 g DMSO, 215 mg Cithrol™ DPHS (PEG-30 dipolyhydroxystearate), 1.1 mL TMEDA, 1.7 mL acetic acid, yielding 710 mg 3e as a white powder, free amino groups 0.154 mmol/g.

3f was prepared as described for 3a except for applying a stirrer speed of 400 rpm, the use of 290 mg of the Backbone reagent that was described in example 1 of WO 2011/012715 A1 as 1g, 2281 mg 2v, 15.8 g DMSO, 290 mg Cithrol™ DPHS (PEG-30 dipolyhydroxystearate), 2.2 mL TMEDA, 3.3 mL acetic acid, sieving on steel sieves of 250, 180, 125, 90, and 63 μm, the product was collected on the 180 μm sieve. Workup was yielding 820 mg 3f as a pale yellow powder, free amino groups 0.108 mmol/g.

3g was prepared as described for 3a except for applying a stirrer speed of 500 rpm, the use of 300 mg of the Backbone reagent that was described in example 1 of WO 2011/012715 A1 as 1g, 2520 mg 2s, 32.4 g DMSO, 300 mg Cithrol™ DPHS (PEG-30 dipolyhydroxystearate), 2.2 mL TMEDA, 3.4 mL acetic acid, yielding 770 mg 3g as a pale yellow powder, free amino groups 0.175 mmol/g.

3h was prepared as described for 3a except for the use of 200 mg 1a, 1995 mg 2ac, 19.8 g DMSO, 195 mg Cithrol™ DPHS (PEG-30 dipolyhydroxystearate), 0.9 mL TMEDA, 1.4 mL acetic acid, yielding 650 mg 3h as a white powder, free amino groups 0.131 mmol/g.

3i was prepared as described for 3a except for the use of 150 mg 1a, 1591 mg 2ag, 15.7 g DMSO, 154 mg Cithrol™ DPHS (PEG-30 dipolyhydroxystearate), 0.7 mL TMEDA, 1.0 mL acetic acid, yielding 300 mg 3i as a white powder, free amino groups 0.123 mmol/g.

3j was prepared as described for 3a except for applying a stirrer speed of 570 rpm, the use of 360 mg 1h, 2567 mg 2ak, 26.3 g DMSO, 257 mg Cithrol™ DPHS (PEG-30 dipolyhydroxystearate), 2.2 mL TMEDA, 3.4 mL acetic acid, yielding 744 mg 3j as a white powder, free amino groups 0.097 mmol/g.

Example 4

Synthesis of Linker Reagent 4c

Linker reagent 4c was synthesized according to the following scheme:

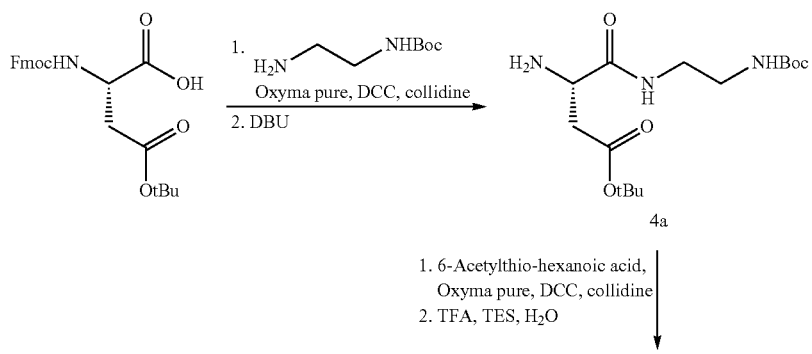

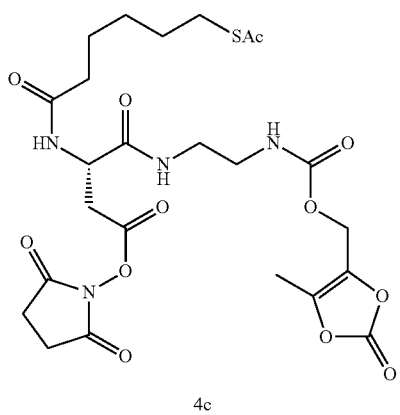

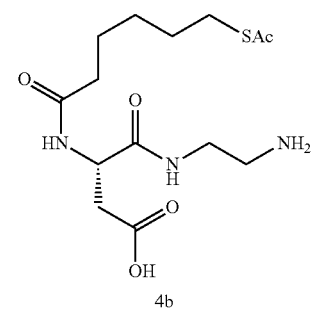

1. (5-Methyl-2-oxo-1,3-dioxol-4-yl)-methyl 4-nitrophenyl carbonate, DIPEA
2. NHS, DCC, DMAP

Synthesis of 4a

Fmoc-L-Asp(OtBu)-OH (1.00 g, 2.43 mmol) was dissolved with DCC (0.70 g, 3.33 mmol) in DCM (25 mL). OxymaPure® (ethyl (hydroxyimino)cyanoacetate) (0.51 g, 3.58 mmol) and collidine (0.50 mL, 3.58 mmol) were added in one portion and a solution of N-Boc-ethylenediamine (0.41 g, 2.56 mmol) in DCM (15 mL) was added slowly. After stirring the mixture for 90 min at RT the formed precipitate was filtered off and the filtrate washed with aqueous HCl (0.1 M, 50 mL). The aqueous layer was extracted with DCM (2×20 mL) and the combined organic fractions were washed with sat. aqueous NaHCO$_3$ (3×25 mL) and brine (1×50 mL), dried over Na$_2$SO$_4$, filtered and concentrated in vacuo. The crude solid was purified by flash chromatography. The intermediate N-boc-N'—(N-fmoc-4-tert.-butyl-L-aspartoyl)-ethylenediamine was obtained as white solid (0.98 g, 1.77 mmol, 73%).

MS: m/z 554.29=[M+H]$^+$, (calculated=554.29).

N-boc-N'—(N-fmoc-4-tert.-butyl-L-aspartoyl)-ethylenediamine (0.98 g, 1.77 mmol) was dissolved in THF (15 mL), DBU (0.31 mL) was added and the solution was stirred for 12 min at RT. The reaction was quenched with AcOH (0.5 ml), concentrated in vacuo and the residue purified by flash chromatography to give 4a (0.61 g, 1.77 mmol, 73% over 2 steps) as white solid.

MS: m/z 332.38=[M+H]$^+$, (calculated=332.22).

Synthesis of 4b

6-Acetylthiohexanoic acid (0.37 g, 1.95 mmol) was dissolved in DCM (19.5 mL) and OxymaPure® (ethyl (hydroxyimino)cyanoacetate) (0.35 g, 2.48 mmol) and DCC (0.40 g, 1.95 mmol) added in one portion. The solution was stirred for 30 min at RT, filtered, and the filtrate added to a solution of 4a (0.61 g, 1.77 mmol) in DCM (10.5 mL). DIPEA (0.46 mL, 2.66 mmol) was added to the solution and the reaction stirred for 2 h at RT. The solution was washed with aqueous H$_2$SO$_4$ (0.1 M, 2×30 mL), sat. aqueous NaHCO$_3$ (2×20 mL) and brine (1×20 mL). The organic layer was dried over Na$_2$SO$_4$, filtered and concentrated in vacuo. The crude material was purified by flash chromatography to give N-boc-N—(N-6-acetylthiohexyl-4-tert.-butyl-L-aspartoyl)-ethylenediamine (0.65 g, 1.30 mmol, 73% over 2 steps) as white solid.

MS: m/z 504.27=[M+H]$^+$, (calculated=504.28).

N-boc-N'—(N-6-Acetylthiohexyl-4-tert.-butyl-L-aspartoyl)-ethylenediamine (0.60 g, 1.18 mmol) was dissolved in TFA (5 mL) and TES (0.13 mL) and water (0.13 ml) were added. The mixture was stirred for 30 min at RT. TFA was removed in a stream of N$_2$, and crude 4b dissolved in H2O/ACN 1:1 and purified by RP-HPLC.

Yield: 0.39 g, 0.85 mmol (TFA salt), 72%.

MS: m/z 348.25=[M+H]$^+$, (calculated=348.16).

Synthesis of 4c 4b (TFA salt, 0.38 g, 0.80 mmol) was dissolved in DMF (5 mL) and (5-methyl-2-oxo-1,3-dioxol-4-yl)-methyl 4-nitrophenyl carbonate (0.26 g, 0.88 mmol) and DIPEA (0.28 mL, 1.6 mmol) were added. The resulting suspension was diluted with DCM (5 mL) and stirred for 3 h at RT. More DIPEA (0.28 mL 1.6 mmol) was added and stirring continued for 2 h. DCM was concentrated in vacuo, the residue diluted with H2O/ACN 3:1 and purified by RP-HPLC to give N-(5-methyl-2-oxo-1,3-dioxol-4-yl)-methyl-oxocarbonyl-N'—(N-6-acetylthiohexyl-L-aspartyl)-ethylenediamine (0.31 g, 0.62 mmol, 77%) as colorless oil.

MS: m/z 504.16=[M+H]$^+$, (calculated=504.17).

N-(5-methyl-2-oxo-1,3-dioxol-4-yl)-methyl oxocarbonyl-N'—(N-6-acetylthiohexyl-L-aspartyl)-ethylene-diamine (150 mg, 0.30 mmol) was dissolved in DCM (17.5 mL) and NHS (41 mg, 0.36 mmol), DCC (74 mg, 0.36 mmol) and DMAP (4 mg, 0.03 mmol) were added in one portion. The reaction was stirred for 1 h at RT and the resulting suspension filtered. The precipitate was washed with a small amount of DCM and the combined filtrates concentrated in vacuo. 4c was purified by RP-HPLC to give a colorless oil (144 mg, 0.24 mmol, 80%). MS: m/z 601.18=[M+H]$^+$, (calculated=601.18).

Example 5

Preparation of Maleimide Functionalized Hydrogel Beads 5a 259.3 mg of dry hydrogel beads 3a was incubated for 15 min in 10 mL 1% n-propylamine in NMP and subsequently washed two times with 1% n-propylamine in NMP and two times with 2% DIPEA in NMP. 171 mg of maleimide-NH-PEG12-PFE was dissolved in 1 mL NMP and added to the washed hydrogel beads 3a. The hydrogel suspension was incubated for 2 h at room temperature. Resulting maleimide functionalized hydrogel beads 5a were washed four times each with NMP, 20 mM succinate, 1 mM Na$_2$EDTA, 0.01% Tween® 20, pH 3.0, water, and with 0.1% acetic acid, 0.01% Tween® 20.

Preparation of Maleimide Functionalized Hydrogel Beads 5b 117.7 mg dry hydrogel beads 3a were swollen in 5 mL NMP and washed five times with NMP and five times with 2% DIPEA in NMP. 5 eq (56 mg) of maleimide-NH-PEG6-PFE (based on amine content of the hydrogel beads) were dissolved in 0.5 mL NMP and added to the washed hydrogel beads 5b. The hydrogel suspension was incubated for 2.5 h at room temperature. Resulting maleimide functionalized hydrogel beads were washed five times each with NMP and afterwards with 0.1% acetic acid, 0.01% Tween® 20.

Example 6

Synthesis of Transient Lucentis®-Linker-Hydrogel Prodrug 6c 4.6 mg Lucentis® (ranibizumab) (depicted in the scheme below as Lucentis®-NH$_2$) (460 μL of 10 mg/mL Lucentis® (ranibizumab) in 10 mM histidine, 10 wt % α,α-trehalose, 0.01% Tween® 20, pH 5.5) was buffer exchanged to 10 mM sodium phosphate, 2.7 mM potassium chloride, 140 mM sodium chloride, pH 7.4 and the concentration of Lucentis® (ranibizumab) was adjusted to 16.4 mg/mL. 6 mg of Linker reagent 4c was dissolved in 100 μL DMSO to yield a concentration of 100 mM. 1 molar equivalent of linker reagent 4c relative to the amount of Lucentis® (ranibizumab) was added to the Lucentis® (ranibizumab) solution. The reaction mixture was mixed carefully and incubated for 5 min at room temperature. Subsequently, 2 additional molar equivalents of linker reagent 4c were added to the Lucentis® (tanibizumab) solution in 1 molar equivalent steps and after addition of each equivalent the reaction mixture was incubated for 5 min at room temperature yielding a mixture of unmodified Lucentis 1z (ranibizumab) and the protected Lucentis®-linker monoconjugate 6a.

The pH of the reaction mixture was adjusted to pH 6.5 by addition of 1 M sodium citrate, pH 5.0 and Na$_2$EDTA was added to a final concentration of 5 mM. To remove the protecting groups of 6a 0.5 M NH$_2$OH (dissolved in 10 mM sodium citrate, 140 mM sodium chloride, 5 mM Na$_2$EDTA, pH 6.5) was added to a final concentration of 45 mM and the deprotection reaction was incubated at room temperature for 4 h yielding the Lucentis®-linker monoconjugate 6b. The mixture of Lucentis® (ranibizumab) and Lucentis®-linker monoconjugate 6b was buffer exchanged to 10 mM sodium phosphate, 2.7 mM potassium chloride, 140 mM sodium chloride, 5 mM Na$_2$EDTA, 0.01% Tween® 20, pH 6.5 and the overall concentration of the two Lucentis® (ranibizumab), species was adjusted to 11.8 mg/mL. The content of Lucentis®-linker monoconjugate 6b in the mixture was 20% as determined by ESI-MS.

4 mg of the Lucentis®/Lucentis-linker monoconjugate 6b mixture in 10 mM sodium phosphate, 2.7 mM potassium chloride, 140 mM sodium chloride, 5 mM Na$_2$EDTA, 0.01% Tween® 20, pH 6.5 were added to 1 mg of maleimide functionalized hydrogel beads 5a and incubated overnight at room temperature yielding transient Lucentis®-linker-hydrogel prodrug 6c.

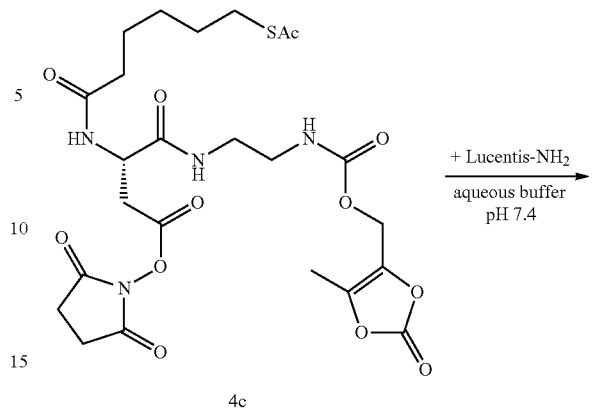

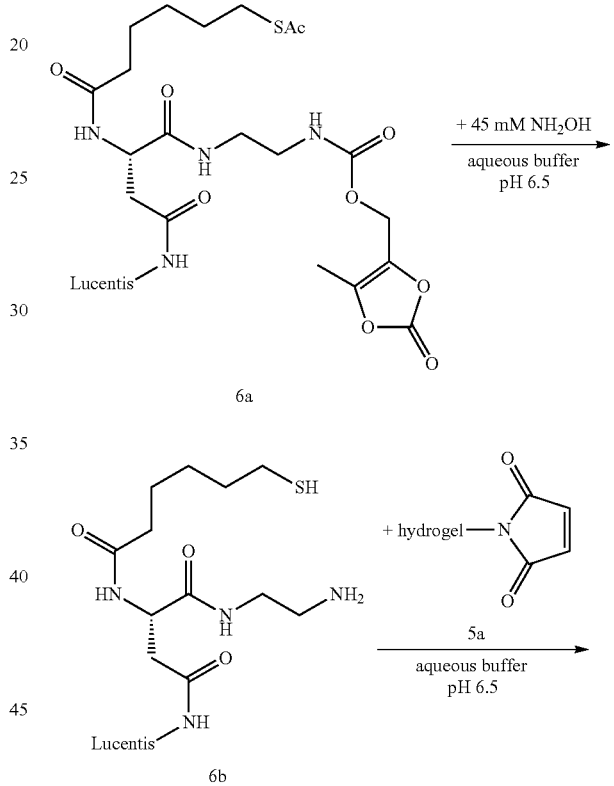

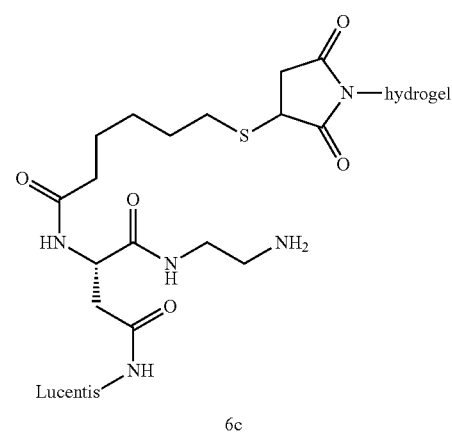

Example 7

In Vitro Release Kinetics—Determination of In Vitro Half-Life

Lucentis®-linker-hydrogel prodrug 6c (containing approximately 1 mg Lucentis® (ranibizumab)) was washed five times with 60 mM sodium phosphate, 3 mM $Na_2EDTA$, 0.01% Tween® 20, pH 7.4 and finally suspended in 1 mL of the aforementioned buffer. The suspension was incubated at 37° C. The buffer of the suspension was exchanged after different time intervals and analyzed by HPLC-SEC at 220 nm. Peaks corresponding to liberated Lucentis® (ranibizumab) were integrated and the total of liberated Lucentis® (ranibizumab) was plotted against total incubation time. Curve fitting software was applied to determine first-order cleavage rates.

Example 8

Preparation of Hydrogel Beads 8a and 8b Containing Free Amino Groups 8a was prepared as described for 3a except for the use of 400 mg [PEG1250-LLys-LLy-LLys$_4$(NH$_2$)$_8$]$_4$, 5082 mg 2s, 33.5 g DMSO, 400 mg Cithrol™ DPHS (PEG-30 dipolyhydroxystearate), 2.3 mL TMEDA, and 4.8 mL acetic acid, yielding 1460 mg 8a as a white powder, free amino groups 0.057 mmol/g.

8b was prepared as described for 3a except for the use of 290 mg [PEG1250-LLys-LLys$_2$-LLys$_4$(NH$_2$)$_8$]$_4$, 2281 mg 2v, 26.1 g DMSO, 257 mg Cithrol™ DPHS (PEG-30 dipolyhydroxystearate), 1.7 mL TMEDA, and 3.5 mL acetic acid, yielding 820 8b as a white powder, free amino groups 0.108 mmol/g.

8c was prepared as described for 3a except for the use of 250 mg [PEG1250-LLys-LLys$_2$-LLys$_4$(NH$_2$)$_8$]$_4$, 2168 mg rac-2y, 21.8 g DMSO, 215 mg Cithrol™ DPHS (PEG-30 dipolyhydroxystearate), 1.1 mL TMEDA, and 1.7 mL acetic acid, yielding 810 mg 8c as a white powder, free amino groups 0.154 mmol/g.

Example 9

Preparation of Biotin Conjugated Hydrogel 9a and 9b 11 mg of 8a were transferred to a syringe equipped with a filter frit. The hydrogel beads 8a were washed three times each with NMP and with $H_2O$/ACN/TFA (1/1/0.002; v/v/v), respectively. 1.14 mg biotinamidohexanoic acid N-hydroxysuccinimide ester (2.5 µmol) were dissolved in 250 µL $H_2O$/ACN/TFA (1/1/0.002; v/v/v), added to the washed hydrogel beads 8a and incubated for 5 min at room temperature under agitation (15 rpm). 50 µL of 0.5 M sodium phosphate, pH 7.4 were added and the reaction mixture was incubated for 60 min at room temperature under agitation (15 rpm). The resulting biotin conjugated hydrogel 9a was washed five times each with $H_2O$/ACN/TFA (1/1/0.002; v/v/v) and with 10 mM sodium phosphate, 2.7 mM potassium chloride, 140 mM sodium chloride, 10% ACN, pH 7.4, respectively.

9b was prepared according to 9a except that 11.3 mg of hydrogel beads 8b and 2.2 mg biotinamidohexanoic acid N-hydroxysuccinimide ester (4.8 µmol) have been used.

Example 10

Preparation of Streptavidin-Biotin Hydrogel 10a and 10b 6 mg streptavidin was dissolved in 10 mM sodium phosphate, 2.7 mM potassium chloride, 140 mM sodium chloride, 10% ACN, pH 7.4, added to biotin conjugated hydrogel 9a (prepared from 11 mg 8a) and incubated for 60 min at room temperature under agitation (15 rpm) yielding streptavidin-biotin hydrogel 10a. 10a was washed two times with 850 µL 10 mM sodium phosphate, 2.7 mM potassium chloride, 140 mM sodium chloride, 10% ACN, pH 7.4 and the wash fractions were combined. The streptavidin amount bound to the biotin conjugated hydrogel was quantified indirectly by photometric determination at 280 nm of the streptavidin concentration in the combined wash fractions and was found to be 2.6 mg.

10b was prepared according to 10a except that biotin conjugated hydrogel 9b (prepared from 11.3 mg 8b) and 8.1 mg streptavidin have been used. The streptavidin amount bound to the biotin conjugated hydrogel 9b was found to be 0.5 mg.

Example 11

Blocked Hydrogel Beads 11

Hydrogel beads were synthesized according to the procedure described in example 3c and functionalized with maleimide groups according to the procedure described in example 5b. Afterwards, 4 mL of the hydrogel suspension at 10 mg/mL were transferred into a 20 mL syringe equipped with a frit. The solvent was expelled and the hydrogel washed 10 times with 5 mL 10 mM histidine/10 wt % α,α-trehalose/0.01% Tween® 20/pH 5.5. The solvent was expelled and 5 mL 1 mM β-mercaptoethanol in 10 mM histidine/10 wt % α,α-trehalose/0.01% Tween® 20/pH 5.5 were drawn into the syringe. The resulting suspension was allowed to incubate at ambient temperature under gentle shaking for 5 min. The solvent was discarded and the hydrogel treated 9 additional times with 5 mL 1 mM β-mercaptoethanol in 10 mM histidine/10 wt % α,α-trehalose/0.01% Tween® 20/pH 5.5. The solvent was each time discarded. The hydrogel beads were then washed 10 times with each time 5 mL 10 mM histidine/10 wt % α,α-trehalose/0.01% Tween® 20/pH 5.5, the solvent was discarded each time. The hydrogel beads were then washed ten times with each time 5 mL PBS-T/pH 7.4, the solvent was discarded each time. Finally, fresh PBS-T/pH 7.4 was drawn into the syringe and the suspension transferred into a Falcon tube to give 11.

Abbreviations

Ac acetyl
ACN acetonitrile
AcOH acetic acid
Asp aspartate
Boc tert-butyloxycarbonyl
DBU 1,8-diazabicyclo (5.4.0)undec-7-ene
DCC dicyclohexylcarbodiimide
DCM dichloromethane
DIPEA diisopropylethylamine
DMAP dimethylaminopyridine
DMF dimethylformamide
DMSO dimethylsulfoxide Fmoc fluorenylmethyloxycarbonyl
HPLC high performance liquid chromatography
iPrOH isopropanol
Maleimide-NH-PEG6-PFE
  N-(3-maleimidopropyl)-21-amino-4,7,10,13,16,19-hexaoxa-heneicosanoic acid pentafluorophenyl ester
Maleimide-NH-PEG12-PFE
  N-(3-maleimidopropyl)-39-amino-4,7,10,13,16,19,22,25,28,31,34,37-dodecaoxa-nonatriacontanoic acid pentafluorophenyl ester
MeOAc methyl acetate
MeOH methanol
MS mass spectrometry
MTBE methyl-tert-butyl ether
NHS N-hydroxysuccinimide
OxymaPure® ethyl 2-cyano-2-(hydroxyimino)acetate
PEG polyethyleneglycol
RP-HPLC reversed phase-high performance liquid chromatography
RT room temperature
tBu tert.-butyl
TAN 1,5,9-triazanonane
TES triethylsilane
TFA trifluoroacetic acid
THF tetrahydrofurane
TMEDA N,N,N',N'-tetramethylethylene diamine
TSTU O—(N-succinimidyl)-N,N,N',N'-tetramethyluronium tetrafluoroborate

The invention claimed is:

1. A process for the preparation of a hydrogel comprising the steps of:
   (a) providing a mixture comprising:
     (a-i) at least one backbone reagent, wherein the at least one backbone reagent has a molecular weight ranging from 1 to 100 kDa, and comprises at least three amines (—NH$_2$ and/or —NH—);
     (a-ii) at least one crosslinker reagent, wherein the at least one crosslinker reagent has a molecular weight ranging from 6 to 40 kDa, the at least one crosslinker reagent comprising:
       (i) at least two carbonyloxy groups (—(C=O)—O— or —O—(C=O)—); and
       (ii) at least two activated functional end groups selected from the group consisting of activated ester groups, activated carbamate groups, activated carbonate groups and activated thiocarbonate groups;
       wherein the at least one crosslinker reagent is PEG-based comprising at least 70% PEG; and
     (a-iii) a first solvent and at least a second solvent, which second solvent is immiscible in the first solvent;
     wherein a weight ratio of the at least one backbone reagent to the at least one crosslinker reagent is in a range of from 1:99 to 99:1; and
   (b) polymerizing the mixture of step (a) in a suspension polymerization to a hydrogel.

2. The process of claim 1;
   wherein the mixture of step (a) further comprises a detergent.

3. The process of claim 2;
   wherein the detergent is PEG 30 dipolyhydroxystearate.

4. The process of claim 1;
   wherein the polymerization in step (b) is initiated by adding a base.

5. The process of claim 4;
   wherein the base comprises at least one compound selected from the group consisting of N,N,N',N'-tetramethylethylene diamine (TMEDA), 1,4-dimethylpiperazine, 4-methylmorpholine, 4-ethylmorpholine, 1,4-diazabicydo[2.2.2]octane, 1,1,4,7,10,10-hexamethyltriethylenetetramine, 1,4,7-trimethyl-1,4,7-triazacyclononane, tris[2-(dimethylamino)ethyl]amine, triethylamine, diisopropylethylamine (DIPEA), trimethylamine, N,N-dimethylethylamine, N,N,N',N'-tetramethyl-1,6-hexanediamine, N,N,N',N'',N''-pentamethyldiethylenetriamine, 1,8-diazabicyclo[5.4.0]undec-7-ene, 1,5-diazabicyclo[4.3.0]non-5-ene, and hexamethylenetetramine.

6. The process of claim 1;
   wherein the mixture of step (a) is an emulsion.

7. The process of claim 1;
   wherein the process further comprises the step of:
   (c) working-up the hydrogel.

8. The process of claim 1;
   wherein the at least one backbone reagent is selected from the group consisting of:
   a compound of formula (I):)

$$B(-(A^0)_{x1}\text{-}(SP)_{x2}\text{-}A^1\text{-}P\text{-}A^2\text{-}Hyp^1)_x \qquad (1);$$

wherein:
B is a branching core;
SP is a spacer moiety selected from the group consisting of C$_{1-6}$ alkyl, C$_{2-6}$ alkenyl and C$_{2-6}$ alkynyl;
P is a PEG-based polymeric chain comprising at least 80% PEG;
Hyp$^1$ is a moiety comprising an amine (—NH$_2$ and/or —NH—) or a polyamine comprising at least two amines (—NH$_2$ and/or —NH—);
x is an integer from 3 to 16;
x1 and x2 are independently of each other 0 or 1, provided that x1 is 0, if x2 is 0;
A$^0$, A$^1$, and A$^2$ are independently of each other selected from the group consisting of:

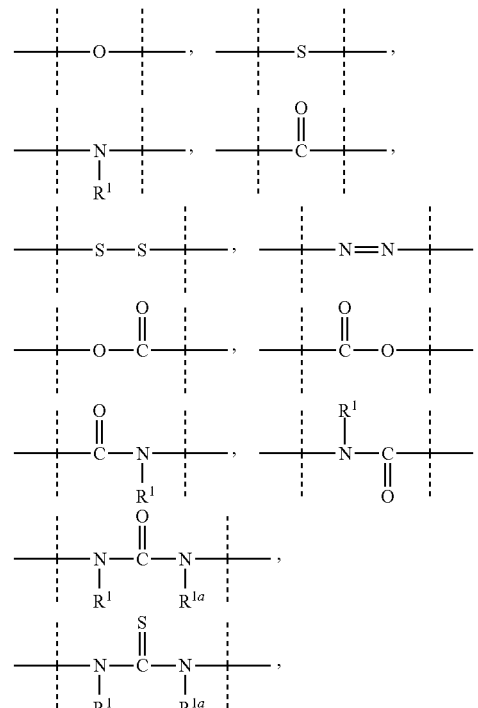

-continued

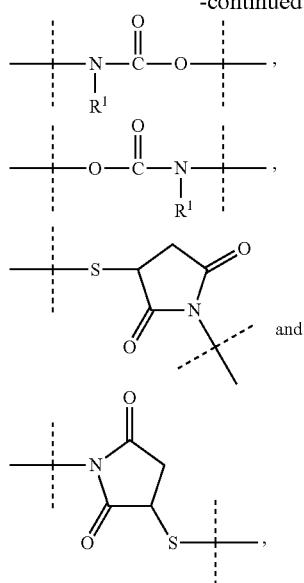

wherein $R^1$ and $R^{1a}$ are independently of each other selected from H and $C_1$ alkyl;

a compound of formula (II):

$$\text{Hyp}^2\text{-}A^3\text{-}P\text{-}A^4\text{-}\text{Hyp}^3 \quad \text{(II)}$$

wherein:
P is defined as above in the compound of formula (I);
$\text{Hyp}^2$ and $\text{Hyp}^3$ are independently of each other a polyamine comprising at least two amines (—$NH_2$ and/or —NH—); and
$A^3$ and $A^4$ are independently selected from the group consisting of:

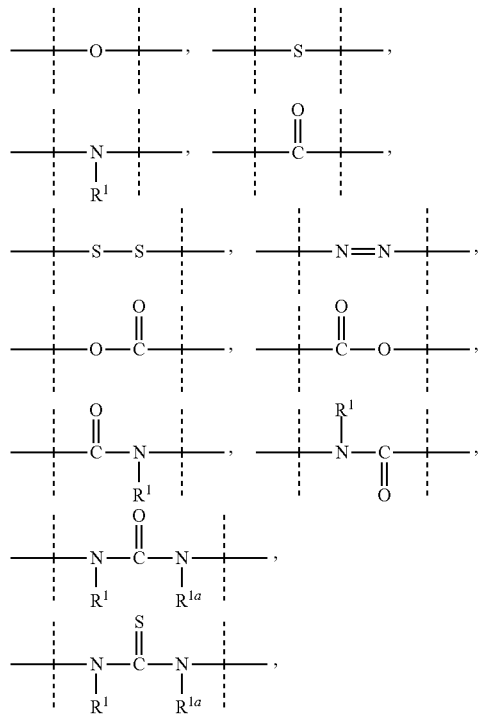

-continued

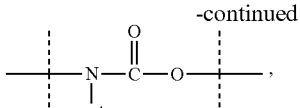
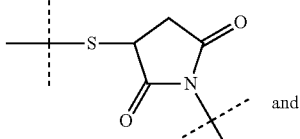
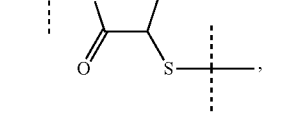

wherein $R^1$ and $R^{1a}$ are independently of each other selected from H and $C_{1-6}$ alkyl;

a compound of formula (III):

$$P^1\text{-}A^5\text{-}\text{Hyp}^4 \quad \text{(III)};$$

wherein
$P^1$ is a PEG-based polymeric chain comprising at least 80% PEG;
$\text{Hyp}^4$ is a polyamine comprising at least three amines (—$NH_2$ and/or —NH—); and
$A^5$ is selected from the group consisting of:

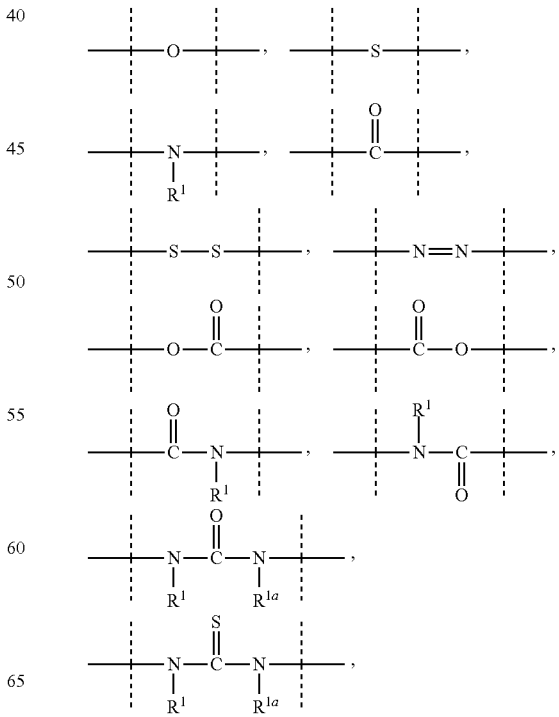

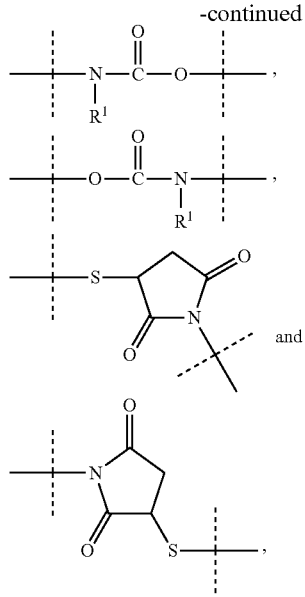

wherein R$^1$ and R$^{1a}$ are independently of each other selected from H and C$_{1-6}$ alkyl; and a compound of formula (IV):

$$T^1\text{-}A^6\text{-}Hyp^5 \qquad (IV);$$

wherein
Hyp$^5$ is a polyamine comprising at least three amines (—NH$_2$ and/or —NH), and
A$^6$ is selected from the group consisting of:

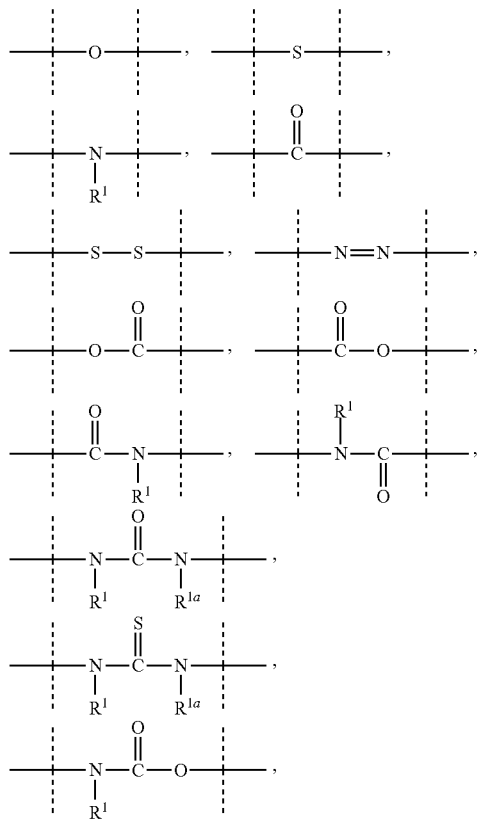

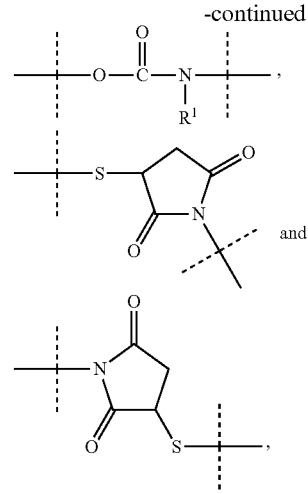

wherein R$^1$ and R$^{1a}$ are independently of each other selected from H and C$_{1-6}$ alkyl; and
T$^1$ is selected from the group consisting of C$_{1-50}$ alkyl, C$_{2-50}$ alkenyl or C$_{2-50}$ alkynyl, which fragment is optionally interrupted by one or more group(s) selected from the group consisting of —NH—, N(C$_{1-4}$ alkyl)-, —O—, —S—, —C(O)—, —C(O)NH—, —C(O)N(C$_{1-4}$ alkyl)-, —O—C(O)—, —S(O)—, —S(O)$_2$—, 4-membered to 7-membered heterocyclyl, phenyl, and naphthyl.

9. The process of claim 8;
wherein Hyp$^1$, Hyp$^2$, Hyp$^3$, Hyp$^4$, and Hyp$^5$ are selected from the group consisting of:
a moiety of formula (e-i):

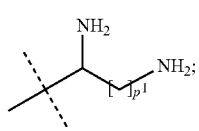

wherein:
p1 is an integer from 1 to 5; and
the dashed line indicates attachment to A$^2$ if the backbone reagent has a structure of formula (I), and to A$^3$ or A$^4$ if the backbone reagent has the structure of formula (H);

a moiety of formula (e-ii):

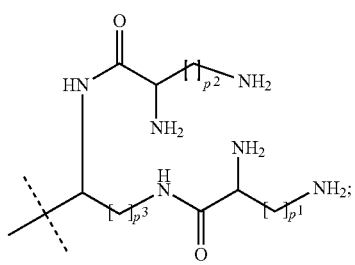

wherein:
p2, p3, and p4 are identical or different and each is independently of the others an integer from 1 to 5; and the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III), and to $A^6$ if the backbone reagent has a structure of formula (IV);

a moiety of formula (e-iii):

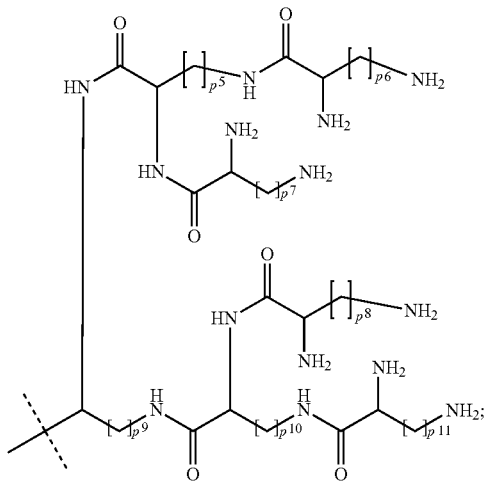

(e-iii)

wherein:
p5 to p11 are identical or different and each is independently of the others an integer from 1 to 5; and
the dashed line indicates attachment to $A^2$ if the backbone reagent is of formula (I), to $A^3$ or $A^4$ if the backbone reagent is of formula (II), to $A^5$ if the backbone reagent is of formula (III), and to $A^6$ if the backbone reagent is of formula (IV);

a moiety of formula (e-iv):

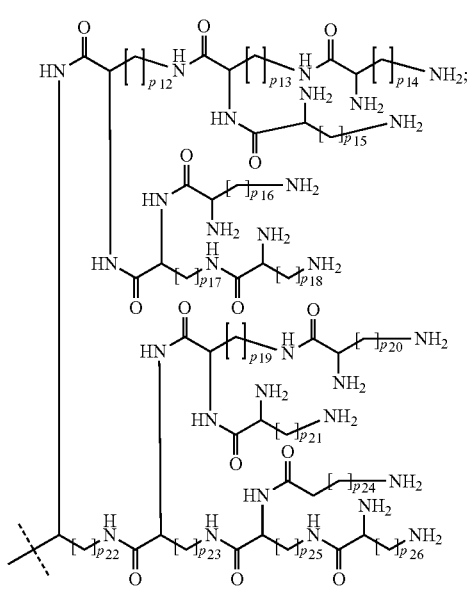

(e-iv)

wherein:
p12 to p26 are identical or different and each is independently of the others an integer from 1 to 5; and
the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III), and to $A^6$ if the backbone reagent has a structure of formula (IV);

a moiety of formula (e-v):

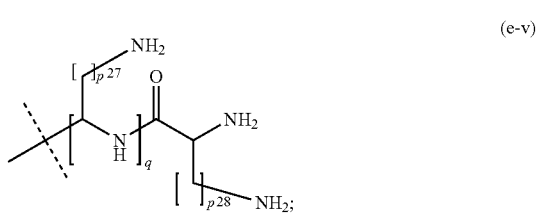

(e-v)

wherein:
p27 and p28 are identical or different and each is independently of the other an integer from 1 to 5;
q is an integer from 1 to 8; and
the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III), and to $A^6$ if the backbone reagent has a structure of formula (IV);

a moiety of formula (e-vi):

(e-vi)

wherein:
p29 and p30 are identical or different and each is independently of the other an integer from 2 to 5; and
the dashed line indicates attachment to $A^2$ if the backbone reagent has the structure of formula (I), to $A^3$ or $A^4$ if the backbone reagent has the structure of formula (II), to $A^5$ if the backbone reagent has the structure of formula (III), and to $A^6$ if the backbone reagent has the structure of formula (IV);

a moiety of formula (e-vii):

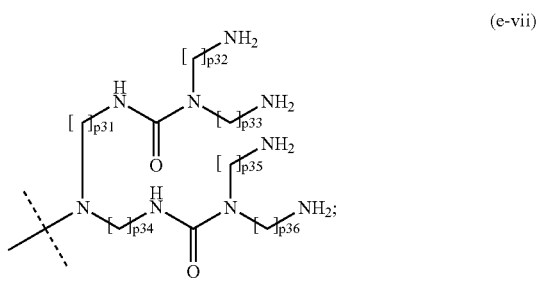

(e-vii)

wherein:

p31 to p36 are identical or different and each is independently of the others an integer from 2 to 5; and the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III), and to $A^6$ if the backbone reagent has a structure of formula (IV);

a moiety of formula (e-viii):

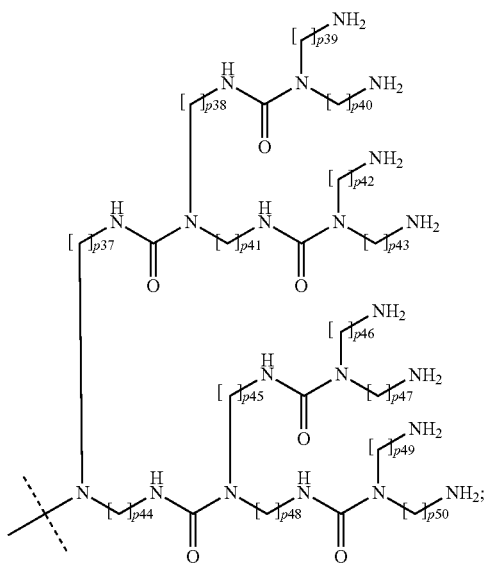

(e-viii)

wherein:

p37 to p50 are identical or different and each is independently of the others an integer from 2 to 5; and the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III), and to $A^6$ if the backbone reagent has a structure of formula (IV); and a moiety of formula (e-ix):

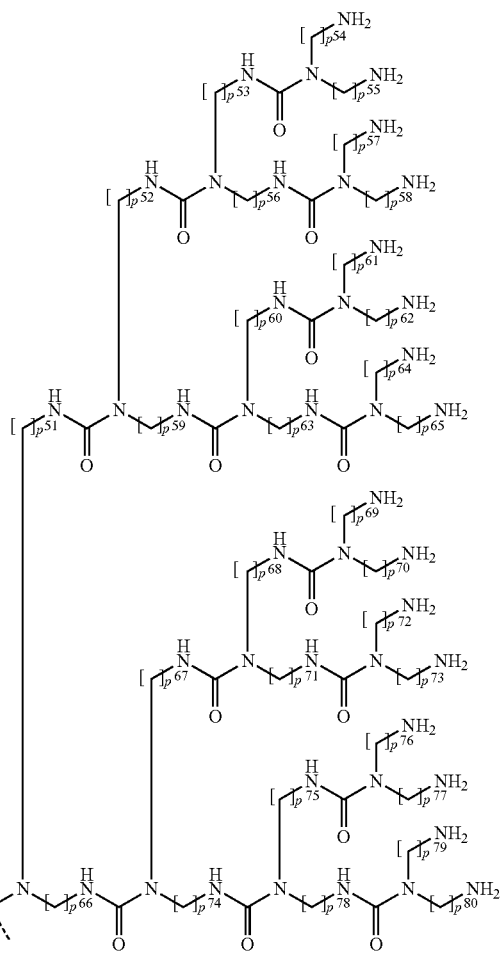

(e-ix)

wherein:

p51 to p80 are identical or different and each is independently of the others an integer from 2 to 5; and the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III), and to $A^6$ if the backbone reagent has a structure of formula (IV); and wherein the moieties (e-i) to (e-v) may at each chiral center be in either R-configuration or S-configuration, with all chiral centers of a moiety (e-i) to (e-v) being in the same configuration.

10. The process of claim 8;

wherein the backbone reagent is a compound of formula (I).

11. The process of any one of claim 8;

wherein the branching core B is selected from the following structures:

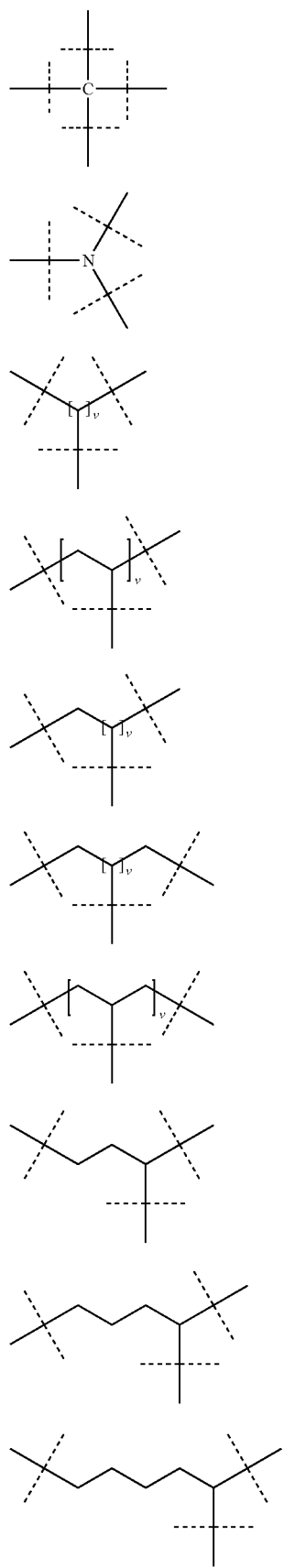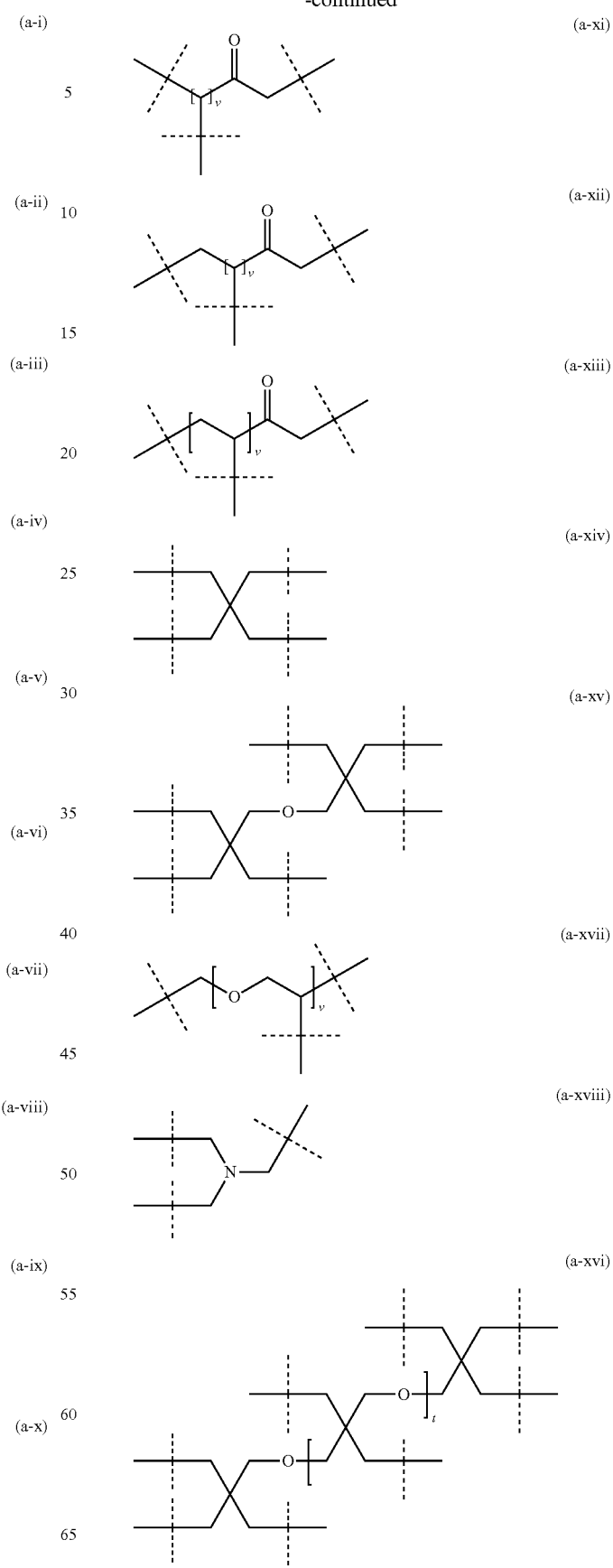

-continued (a-xix)

(a-xx)

(a-xxi)

(a-xxii)

(a-xxiii)

wherein:
 dashed lines indicate attachment to $A^0$ or, if x1 and x2 are both 0, to $A^1$,
 t is 1 or 2; and
 v is an integer from 1 to 14.

12. The process of claim 11;
wherein B is of formula (a-xiv).

13. The process of claim 8;
wherein $A^0$ is:

(structures shown) , or

14. The process of claim 8;
wherein x1 and x2 are 0.

15. The process of claim 8;
wherein P has the structure of formula (c-i):

(c-i)

wherein n ranges from 6 to 900.

16. The process of claim 9;
wherein the at least one backbone reagent is a compound of the formula (I); and
wherein the moiety -$A^2$-$Hyp^1$ is a moiety of the formula:

(structure with $E^1$)

wherein:
 the dashed line indicates attachment to P; and
 $E^1$ is $Hyp^1$, and is selected from formulas (e-i) to (e-ix).

17. The process of claim 1;
wherein the backbone reagent has the following formula:

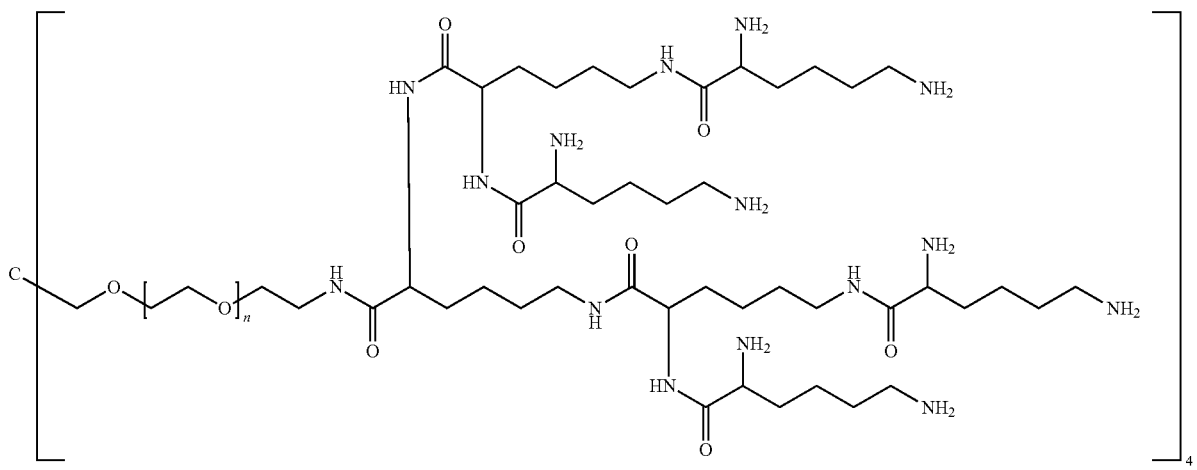

wherein:
  n ranges from 10 to 40.

18. The process of claim 17;
wherein n ranges from 20 to 30.

19. The process of claim 1;
wherein the backbone reagent is present in the form of its acidic salt.

20. The process of claim 1;
wherein the crosslinker reagent is a compound of formula (V-II):

$P^2$ is:

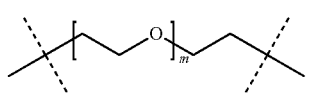

m ranges from 120 to 920;
r1 and r2, r7, r8 are independently 0 or 1;
r3 and r6 are independently an integer from 0 to 4;
r4 and r5 are independently an integer from 1 to 10;

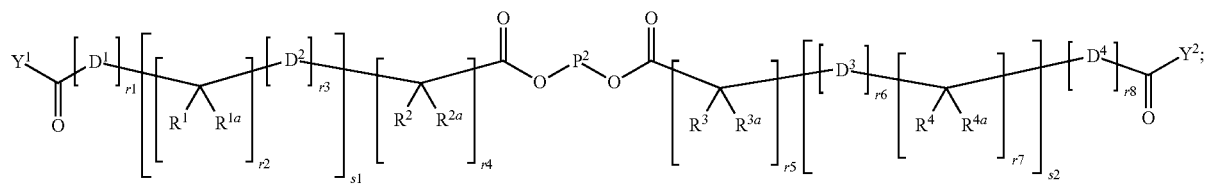

(V-II)

wherein:
  $D^1$, $D^2$, $D^3$ and $D^4$ are identical or different and each is independently of the others selected from the group consisting of O, $NR^5$, S, and $CR^5R^{5a}$;
wherein:
  $R^1$, $R^{1a}$, $R^2$, $R^2$, $R^3$, $R^{3a}$, $R^4$, $R^{4a}$, $R^5$, and $R^{5a}$ are identical or different and each is independently of the others selected from the group consisting of H and $C_1$ alkyl; or
  optionally, one or more of the pair(s) $R^1/R^{1a}$, $R^2/R^{2a}$, $R^3/R^{3a}$, $R^4/R^{4a}$, $R^1/R^2$, $R^3/R^4$, $R^{1a}/R^{2a}$, and $R^{3a}/R^{4a}$ form a chemical bond or are joined together with the atom to which they are attached to form a $C_{3-8}$ cycloalkyl or to form a ring A or are joined together with the atom to which they are attached to form a 4-membered to 7-membered heterocyclyl or 8-membered to 11-membered heterobicyclyl or adamantyl; and
wherein:
  A is selected from the group consisting of phenyl, naphthyl, indenyl, indanyl, and tetralinyl;

s1 and s2 are independently an integer from 1 to 6;
$Y^1$ and $Y^2$ are identical or different and each is independently of the other selected from formulas (f-i) to (f-vi):

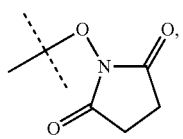
(f-i)

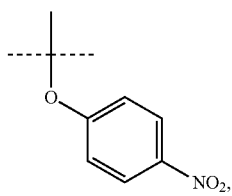
(f-ii)

-continued
(f-iii)
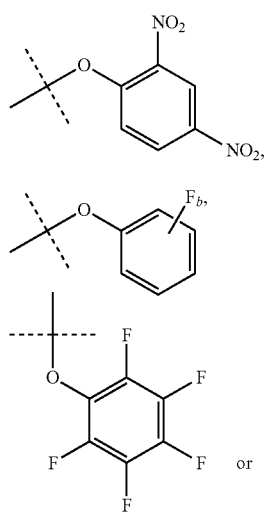
(f-iv)
(f-v)
(f-vi)
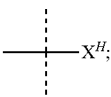
wherein:
the dashed lines indicate attachment to the rest of the molecule;
b is an integer from 1 to 4; and
$X^H$ is Cl, Br, I, or F.
21. The process of claim 1;
wherein the crosslinker reagent comprises a compound selected from the group consisting of formulas (V-1) to (V-54):
(V-1) (V-2)
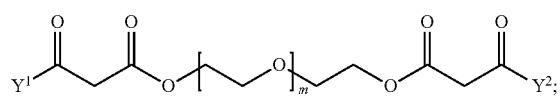
(V-3) (V-4)
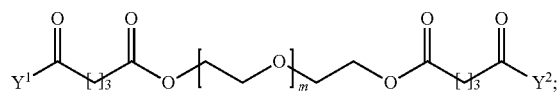 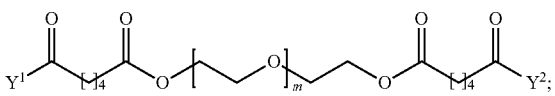
(V-5) (V-6)
(V-7) (V-8)
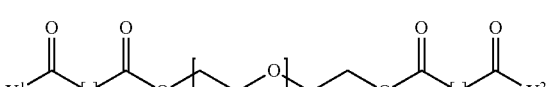
(V-9) (V-10)
(V-11) (V-12)
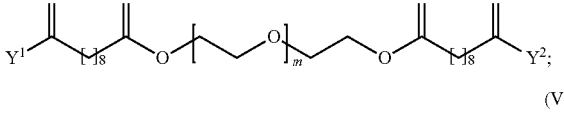
(V-13) (V-14)
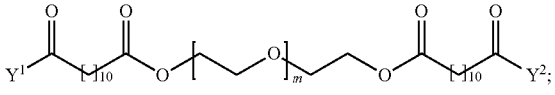
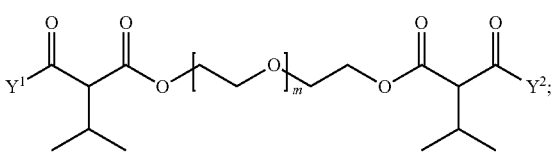

(V-15)
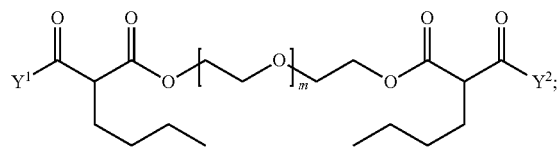
(V-16)
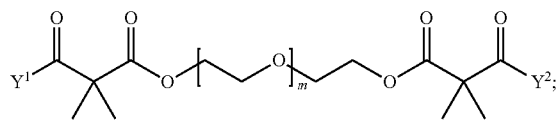
(V-17)
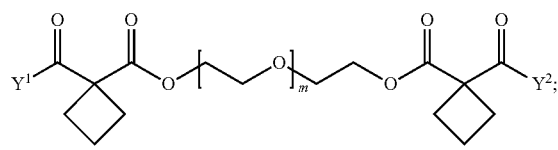
(V-18)
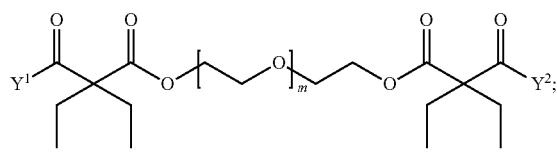
(V-19)
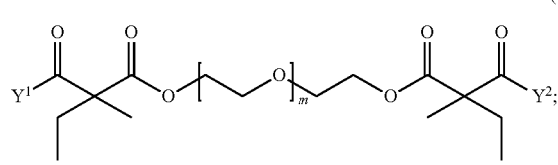
(V-20)
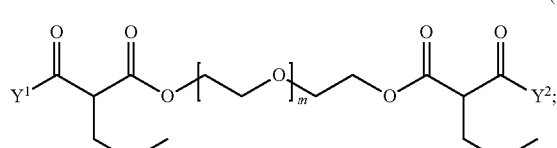
(V-21)
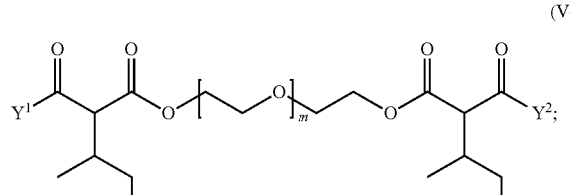
(V-22)
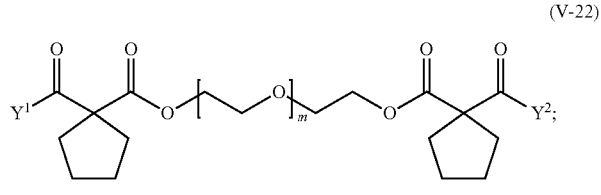
(V-23)
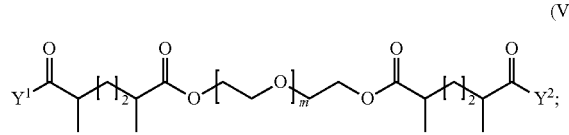
(V-24)
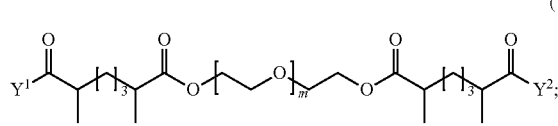
(V-25)
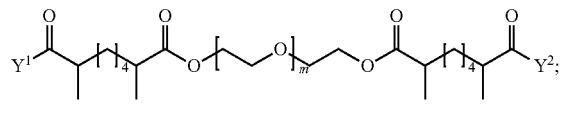
(V-26)
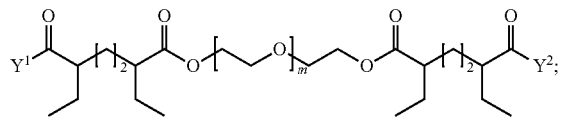
(V-27)
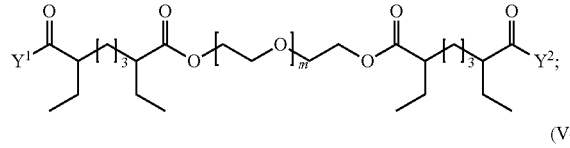
(V-28)
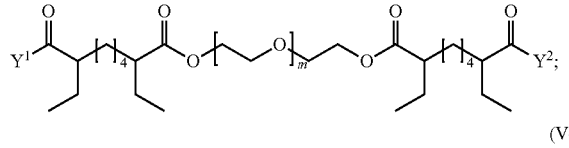
(V-29)
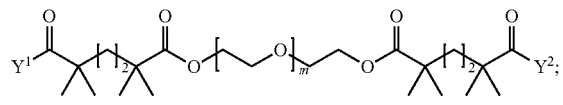
(V-30)
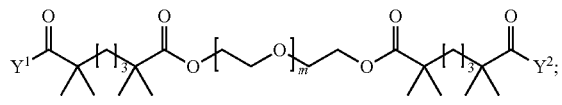
(V-31)
(V-32)
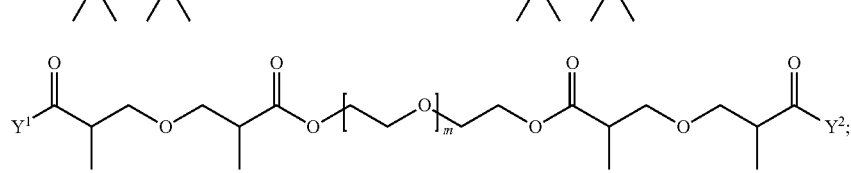

-continued

Structures (V-33) through (V-49) showing various diester compounds with Y¹ and Y² end groups connected through polyethylene glycol spacers $[OCH_2CH_2]_m$ and various cyclic (cyclopropane, cyclobutane, cyclopentane, cyclohexane, cycloheptane) or alkyl chain linkers, in both trans and cis configurations.

(V-50)

(V-51)

(V-52)

(V-53)

(V-54)

wherein:
each crosslinker reagent may be in the form of its racemic mixture, where applicable; and
m ranges from 120 to 920;
$Y^1$ and $Y^2$ are identical or different and each is independently of the other selected from formulas (f-i) to (f-vi):

(f-i)

(f-ii)

(f-iii)

(f-iv)

(f-v)

(f-vi)

wherein:
the dashed lines indicate attachment to the rest of the molecule;
b is 1, 2, 3, or 4; and
$X^H$ is Cl, Br, j, or F.

22. The process of claim 1;
wherein the hydrogel obtained from the polymerization is a shaped article.

23. The process of claim 22;
wherein the hydrogel is in the form of microparticular beads having a diameter of 1 to 500 micrometer.

24. A hydrogel obtained by the process of claim 1.

25. A process for the preparation of a hydrogel-spacer conjugate comprising the steps of:
preparing a hydrogel according to the method of claim 1; and
(d) reacting the hydrogel with a spacer reagent of the formula (VI) in the presence of a solvent to obtain a hydrogel-spacer conjugate;
where the formula (VI) is:

$$A^{x1}\text{-}S^0\text{-}A^{x2} \quad (VI);$$

wherein:
S⁰ is selected from the group consisting of $C_{1-50}$ alkyl, $C_{2-50}$ alkenyl, and $C_{2-50}$ alkynyl, which fragment is optionally interrupted by one or more group(s) selected from —NH—, —N($C_{1-4}$ alkyl)-, —O—, —S, —C(O)—, —C(O)NH, —C(O)N($C_{1-4}$ alkyl)-, —O—C(O)—, —S(O)—, —S(O)$_2$—, 4-membered to 7-membered heterocyclyl, phenyl, and naphthyl;
$A^{x1}$ is a functional group for reaction with an amine group of the hydrogel; and
$A^{x2}$ is a functional group.

26. The process of claim 25;
wherein $A^{x1}$ is selected from the group consisting of activated carboxylic acid, Cl—(C=O)—, N-hydroxysuccinimide-(C=O)—, ClSO$_2$—, $R^1$(C=O)—, I—, Br—, Cl—, SCN—, and CN—;
wherein:
$R^1$ is selected from the group consisting of H, $C_{1-6}$ alkyl, alkenyl, $C_{2-6}$ alkynyl, $C_{3-8}$ cycloalkyl, 4-membered to 7-membered heterocyclyl, 8-membered to 11-membered hetetobicyclyl, phenyl, naphthyl, indenyl, indanyl, and tetralinyl.

27. The process of claim 25;
wherein $A^{x2}$ is selected from the group consisting of -maleimide, —SH, —NH$_2$, —SeH, —N$_3$, —C≡CH, —CR$^1$=CR$^{1a}$R$^{1b}$, —OH, —(CH=X⁰)—R$^1$, —(C=O)—S—R$^1$, —(C=O)—H, —NH—NH$_2$, —O—NH$_2$, -Ar-X⁰, -Ar-Sn($R^1$)($R^{1a}$)($R^{1b}$),

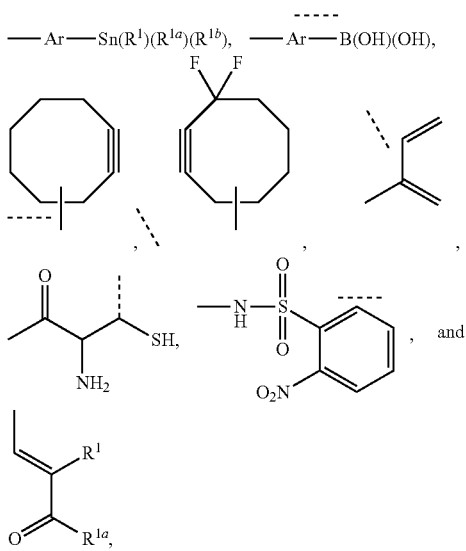

with optional protecting groups;
wherein:
X⁰ is —OH, —NR$^1$R$^{1a}$, —SH, or —SeH;
Ar is selected from the group consisting of phenyl, naphthyl, indenyl, indanyl, and tetralinyl; and
$R^1$, $R^{1a}$, $R^{1b}$ are independently of each other selected from the group consisting of H, $C_{1-8}$ alkyl, $C_{2-6}$ alkenyl, $C_{2-6}$ alkynyl, $C_{3-8}$ cycloalkyl, 4-membered to 7-membered heterocyclyl, 8-membered to 11-membered heterobicyclyl, phenyl, naphthyl, indenyl, indanyl, and tetralinyl.

28. A hydrogel-spacer conjugate obtained by the process of claim 26.

29. A process for the preparation of a carrier-linked prodrug comprising the step of:
preparing a hydrogel according to the method of claim 1; and
(e) reacting the hydrogel with a prodrug linker-biologically active moiety reagent of formula (VII) in the presence of a solvent, to obtain a carrier linked prodrug;
wherein the formula (VII) is:

$A^{y1}$-L-D           (VII);

wherein:
$A^{y1}$ is a functional group for reaction with an amine of the hydrogel;
L is a prodrug linker; and
D is a biologically active moiety.

30. A process for the preparation of a carrier-linked prodrug comprising the step of:
preparing a hydrogel according to the method of claim 1;
(d) reacting the hydrogel with a spacer reagent of the formula (VI) in the presence of a solvent to obtain a hydrogel-spacer conjugate; and
(e) reacting the hydrogel-spacer conjugate with a prodrug linker-biologically active moiety reagent of formula (VII) in the presence of a solvent, to obtain a carrier linked prodrug;
where the formulas (VI) and (VII) are:

$A^{x1}$-S⁰-$A^{x2}$           (VI); and $A^{y1}$-L-D           (VII);

wherein:
S⁰ is selected from the group consisting of $C_{1-50}$ alkyl, $C_{2-50}$ alkenyl, and $C_{2-50}$ alkynyl, which fragment is optionally interrupted by one or more group(s) selected from —NH—, —N($C_{1-4}$ alkyl)-, —O—, —S, —C(O)—, —C(O)NH, —C(O)N($C_{1-4}$ alkyl)-, —O—C(O)—, —S(O)—, —S(O)$_2$—, 4-membered to 7-membered heterocyclyl, phenyl, and naphthyl;
$A^{x1}$ is a functional group for reaction with an amine group of the hydrogel:
L is a prodrug linker;
D is a biologically active moiety; and
$A^{x2}$ and $A^{y1}$ are selected from the following:

| $A^{x2}$ | $A^{y1}$ |
|---|---|
| -maleimide | HS—, H$_2$N—, or HSe— |
| —SH, —NH$_2$, or —SeH | maleimide- |
| —N$_3$ | HC≡C—, |
| | 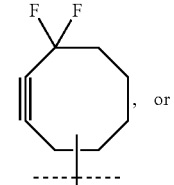, or |
| | 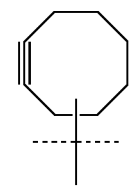 |

| $A^{x2}$ | $A^{y1}$ |
|---|---|
| —NH₂ or 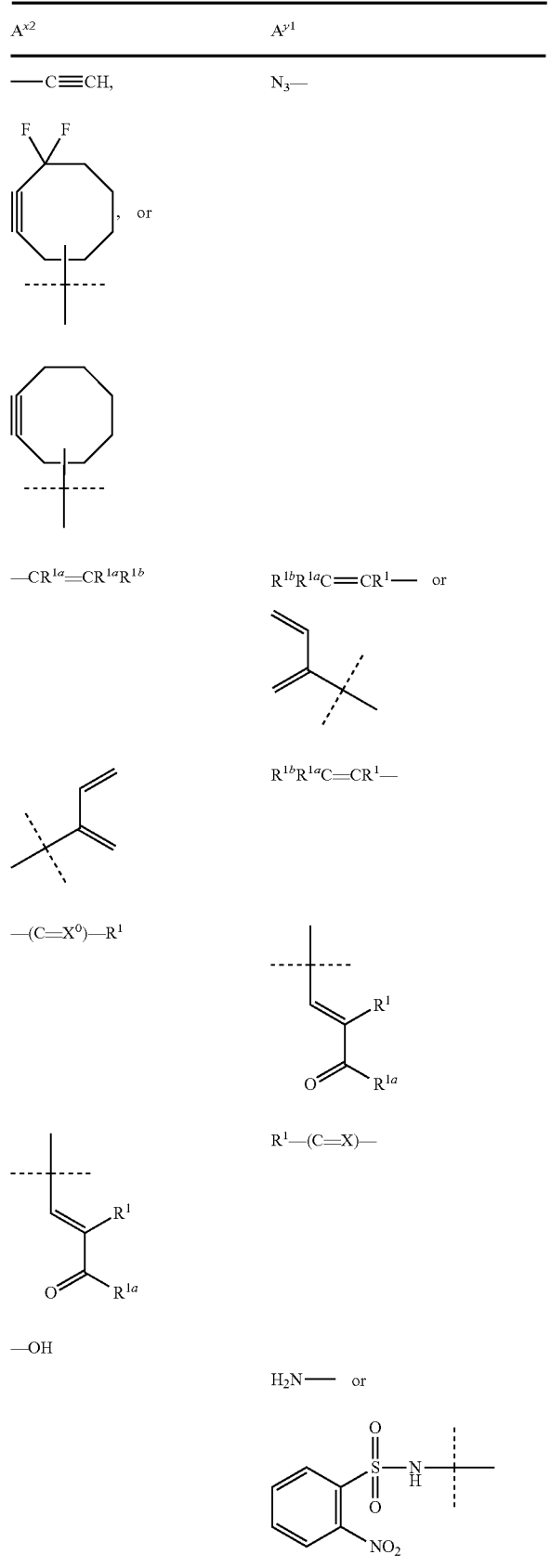 | HO— |
| —(C=O)—S—R¹ | |
| | 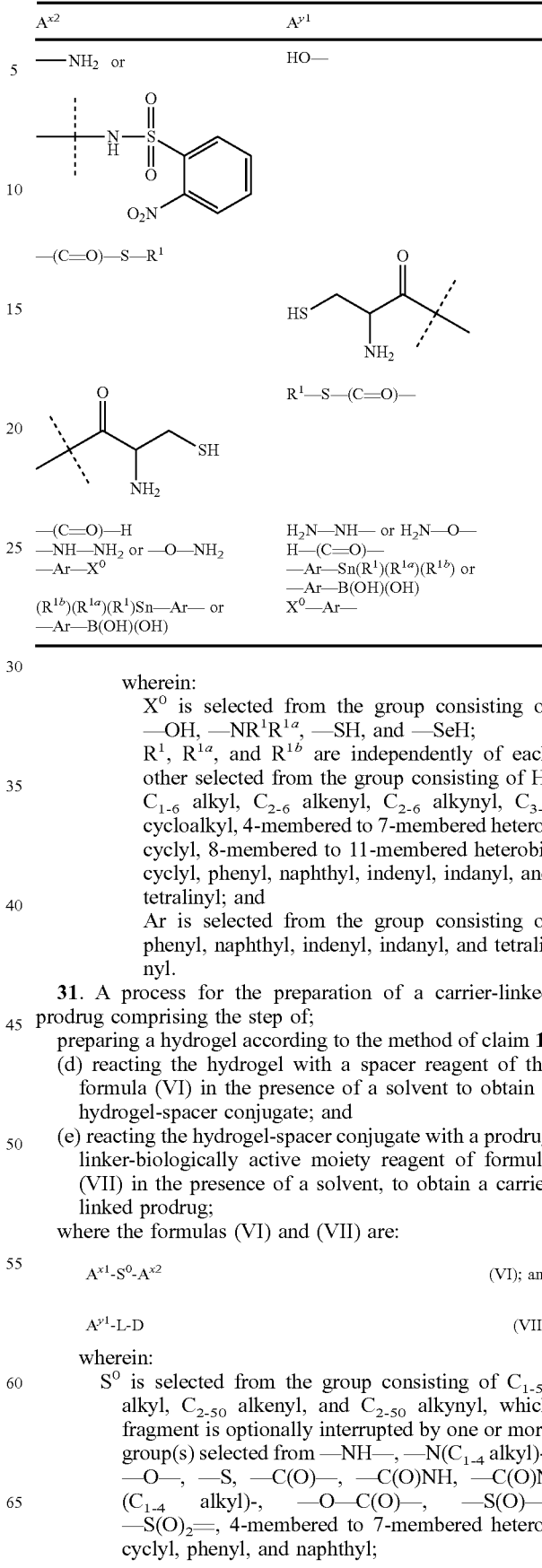 |
| | R¹—S—(C=O)— |
| —(C=O)—H<br>—NH—NH₂ or —O—NH₂<br>—Ar—X⁰ | H₂N—NH— or H₂N—O—<br>H—(C=O)—<br>—Ar—Sn(R¹)(R¹ᵃ)(R¹ᵇ) or<br>—Ar—B(OH)(OH) |
| (R¹ᵇ)(R¹ᵃ)(R¹)Sn—Ar— or<br>—Ar—B(OH)(OH) | X⁰—Ar— | wherein:
  $X^0$ is selected from the group consisting of —OH, —NR¹R¹ᵃ, —SH, and —SeH;
  $R^1$, $R^{1a}$, and $R^{1b}$ are independently of each other selected from the group consisting of H, $C_{1-6}$ alkyl, $C_{2-6}$ alkenyl, $C_{2-6}$ alkynyl, $C_{3-8}$ cycloalkyl, 4-membered to 7-membered heterocyclyl, 8-membered to 11-membered heterobicyclyl, phenyl, naphthyl, indenyl, indanyl, and tetralinyl; and
  Ar is selected from the group consisting of phenyl, naphthyl, indenyl, indanyl, and tetralinyl.

31. A process for the preparation of a carrier-linked prodrug comprising the step of;
  preparing a hydrogel according to the method of claim 1;
  (d) reacting the hydrogel with a spacer reagent of the formula (VI) in the presence of a solvent to obtain a hydrogel-spacer conjugate; and
  (e) reacting the hydrogel-spacer conjugate with a prodrug linker-biologically active moiety reagent of formula (VII) in the presence of a solvent, to obtain a carrier linked prodrug;
  where the formulas (VI) and (VII) are:

$A^{x1}$-$S^0$-$A^{x2}$  (VI); and $A^{y1}$-L-D  (VII);

wherein:
  $S^0$ is selected from the group consisting of $C_{1-50}$ alkyl, $C_{2-50}$ alkenyl, and $C_{2-50}$ alkynyl, which fragment is optionally interrupted by one or more group(s) selected from —NH—, —N($C_{1-4}$ alkyl)-, —O—, —S—, —C(O)—, —C(O)NH, —C(O)N($C_{1-4}$ alkyl)-, —O—C(O)—, —S(O)—, —S(O)₂=, 4-membered to 7-membered heterocyclyl, phenyl, and naphthyl;

$A^{x1}$ is a functional group for reaction with an amine group of the hydrogel;
L is a prodrug linker;
D is a biologically active moiety;
$A^{x2}$ is a thiol; and
$A^{y1}$ is of formula (VIIa)

$$T\text{-}PG^0\text{-}S— \qquad (VIIa);$$

wherein:
T is H or a tag moiety;
$PG^0$ is a sulfur-activating moiety; and
S is sulfur.

32. The process of claim 29;
wherein D has a molecular weight ranging between 2 and 500 kDa.

33. A carrier-linked prodrug obtained by the process for the preparation of a carrier-linked prodrug of claim 29.

34. A pharmaceutical composition comprising:
the carrier-linked prodrug of claim 33 or a pharmaceutical salt thereof; and
a pharmaceutically acceptable excipient.

35. A medicament comprising:
the carrier-linked prodrug of claim 33.

36. A medicament comprising:
the pharmaceutical composition of claim 34.

37. A process for the preparation of a carrier-linked prodrug comprising the step of:
preparing a hydrogel-spacer conjugate according to the method of claim 26; and
(e) reacting the hydrogel-spacer conjugate with a prodrug linker-biologically active moiety reagent of formula (VII) in the presence of a solvent, to obtain a carrier linked prodrug;
wherein the formula (VII) is:

$$A^{y1}\text{-}L\text{-}D \qquad (VII);$$

wherein:
$A^{y1}$ is a functional group for reaction with the functional group $A^{x2}$ of the hydrogel-spacer conjugate;
L is a prodrug linker; and
D is a biologically active moiety.

38. The process of claim 37;
wherein $A^{x2}$ and $A^{y1}$ are selected from the following:

| $A^{x2}$ | $A^{y1}$ |
|---|---|
| -maleimide | HS—, $H_2N$—, or HSe— |
| —SH, —$NH_2$, or —SeH | maleimide- |
| —$N_3$ | HC≡C—, |
| | difluorocyclooctyne group, or |
| | cyclooctyne group |
| —C≡CH, | $N_3$— |
| difluorocyclooctyne group, or | |
| cyclooctyne group | |
| —$CR^{1a}$=$CR^{1a}R^{1b}$ | $R^{1b}R^{1a}C$=$CR^1$— or |
| | diene group |
| | $R^{1b}R^{1a}C$=$CR^1$— |
| —(C=$X^0$)—$R^1$ | |
| | α,β-unsaturated carbonyl with $R^1$, $R^{1a}$ |
| | $R^1$—(C=X)— |
| α,β-unsaturated carbonyl with $R^1$, $R^{1a}$ | |
| —OH | $H_2N$— or |
| | 2-nitrobenzenesulfonamide group |
| —$NH_2$ or | HO— |
| 2-nitrobenzenesulfonamide group | |

-continued

| $A^{x2}$ | $A^{y1}$ |
|---|---|
| —(C=O)—S—$R^1$ | 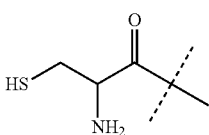 |
| 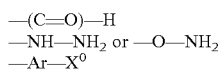 | $R^1$—S—(C=O)— |
| —(C=O)—H | $H_2N$—NH— or $H_2N$—O— |
| —NH—$NH_2$ or —O—$NH_2$ | H—(C=O)— |
| —Ar—$X^0$ | —Ar—Sn($R^1$)($R^{1a}$)($R^{1b}$) or —Ar—B(OH)(OH) |
| ($R^{1b}$)($R^{1a}$)($R^1$)Sn—Ar— or —Ar—B(OH)(OH) | $X^0$—Ar— | wherein:
 $X^0$ is selected from the group consisting of —OH, —$NR^1R^{1a}$, —SH, and —SeH;
 $R^1$, $R^{1a}$, and $R^{1b}$ are independently of each other selected from the group consisting of H, $C_{1-6}$ alkyl, $C_{1-6}$ alkenyl, $C_{2-6}$ alkynyl, $C_{3-8}$ cycloalkyl, 4-membered to 7-membered heterocyclyl, 8-membered to 11-membered heterobicyclyl, phenyl, naphthyl, indenyl, indanyl, and tetralinyl; and
 Ar is selected from the group consisting of phenyl, naphthyl, indenyl, indanyl, and tetralinyl.

39. The process of claim 37;
 wherein $A^{x2}$ is a thiol and $A^{y1}$ is of formula (VIIa);

$$T\text{-}PG^0\text{-}S— \qquad (VIIa);$$

wherein
 T is H or a tag moiety;
 $PG^0$ is a sulfur-activating moiety; and
 S is sulfur.

40. The process of claim 37;
 wherein D has a molecular weight ranging between 2 and 500 kDa.

41. A carrier-linked prodrug obtained by the process for the preparation of a carrier-linked prodrug of claim 37.

42. A pharmaceutical composition comprising:
 the carrier-linked prodrug of claim 41 or a pharmaceutical salt thereof; and
 a pharmaceutically acceptable excipient.

43. A medicament comprising:
 the carrier-linked prodrug of claim 41.

44. A medicament comprising:
 the pharmaceutical composition of claim 42.

* * * * *

UNITED STATES PATENT AND TRADEMARK OFFICE
CERTIFICATE OF CORRECTION

PATENT NO. : 9,855,340 B2
APPLICATION NO. : 14/434585
DATED : January 2, 2018
INVENTOR(S) : Rau et al.

It is certified that error appears in the above-identified patent and that said Letters Patent is hereby corrected as shown below:

In the Specification

At Column 7, Lines 10-15, the chemical structure:

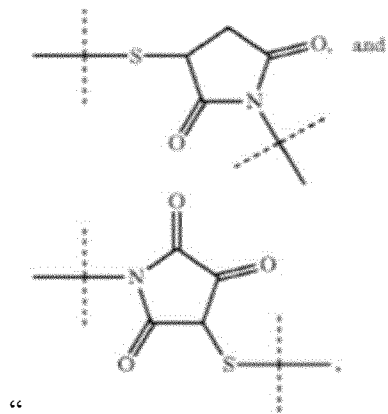

"                    "

Should be replaced with the Structure shown below:

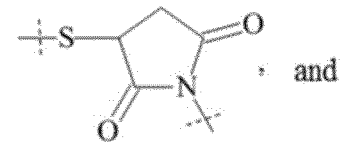

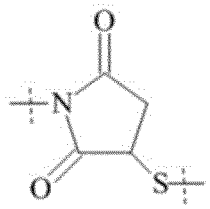

Signed and Sealed this
Eleventh Day of December, 2018

Andrei Iancu
*Director of the United States Patent and Trademark Office*

CERTIFICATE OF CORRECTION (continued)
U.S. Pat. No. 9,855,340 B2

At Column 9, Line 32:
The formula "≡N(O)-" should read "=N(O)-"

In the Claims

At Column 113, Claim 8, Line 26:
The term "$C_1$ alkyl-" should read "$C_{1-6}$ alkyl"

At Column 116, Claim 8, Line 27:
The term "N($C_{1-4}$ alkyl)-" should read "-N($C_{1-4}$ alkyl)-"

At Column 116, Claim 8, Line 28:
"-C(O)N(C, alkyl)-" should read "-C(O)N($C_{1-4}$ alkyl)-"

At Column 116, Claim 9, Line 48, Column 117, Claim 9, Line 4, Column 118, Claim 9, Line 49, and Column 119, Claim 9, Line 64:
Formula "(H)" should read formula "(II)"

At Column 116, Claim 9, Line 60, In the structure (e-ii):

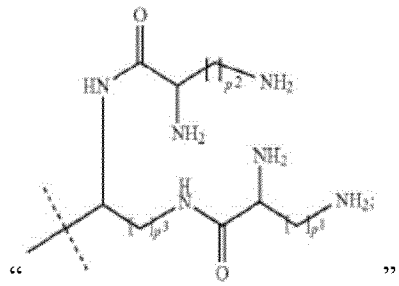
"         "

Should read as shown below:

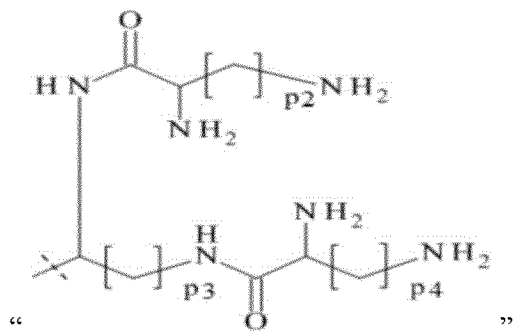
"         "

At Column 125, Claim 20, Line 52:
The second of the two terms "$R^2$" should read "$R^{2a}$"

At Column 125, Claim 20, Line 55:
The term "$C_1$ alkyl" should read "$C_{1-6}$ alkyl"

At Column 135, Claim 25, Line 6:
The terms "-S" and "-C(O)NH" should read "-S-" and "-C(O)NH-"

CERTIFICATE OF CORRECTION (continued)
U.S. Pat. No. 9,855,340 B2

At Column 135, Claim 27, Line 30-50, the chemical structures:

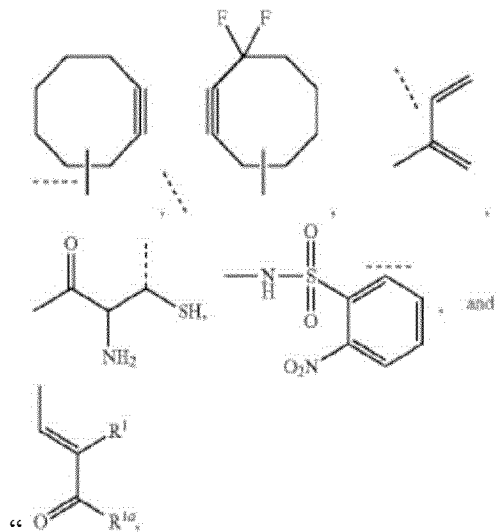

"

Please replace the chemical structure as shown below:

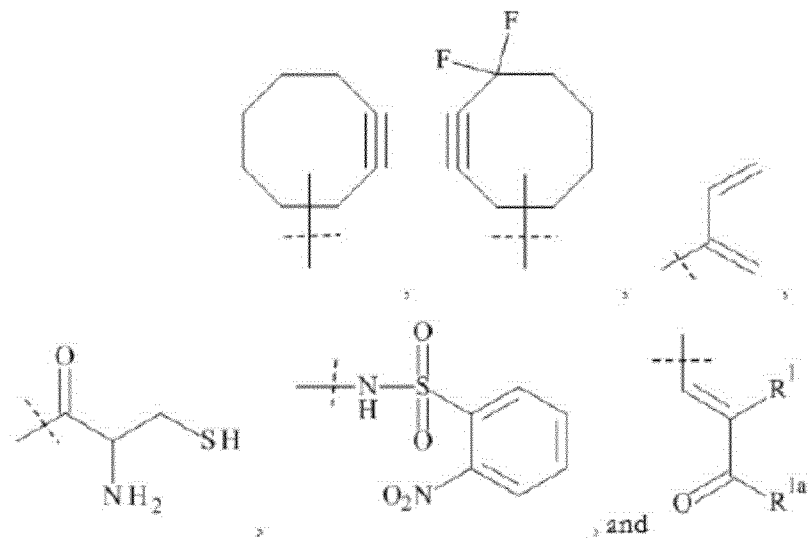

At Column 135, Claim 27, Line 60:
The term "$C_{1-8}$ alkyl" should read "$C_{1-6}$ alkyl"

At Column 136, Claim 30, Line 33:
The terms "-S" and "-C(O)NH" should read "-S-" and "-C(O)NH-"

At Column 138, Claim 31, Line 64:
The terms "-S" and "-C(O)NH" should read "-S-" and "-C(O)NH-"

At Column 138, Claim 31, Line 66:
The formula "-S(O)$_2$=" should read "-S(O)$_2$-"

CERTIFICATE OF CORRECTION (continued)
U.S. Pat. No. 9,855,340 B2

At Column 141, Claim 31, Line 28:
The expression "$C_{1-6}$ alkenyl" should read "$C_{2-6}$ alkenyl"